United States Patent
Graversen et al.

(10) Patent No.: US 6,897,039 B2
(45) Date of Patent: May 24, 2005

(54) APOLIPOPROTEIN ANALOGUES

(75) Inventors: Jonas Graversen, Åbyhøj (DK); Søren Moestrup, Aarhus (DK)

(73) Assignee: ProteoPharma Aps, Arhus (DK)

( * ) Notice: Subject to any disclaimer, the term of this patent is extended or adjusted under 35 U.S.C. 154(b) by 208 days.

(21) Appl. No.: 09/987,107

(22) Filed: Nov. 13, 2001

(65) Prior Publication Data

US 2002/0156007 A1 Oct. 24, 2002

Related U.S. Application Data

(60) Provisional application No. 60/264,022, filed on Jan. 26, 2001.

(30) Foreign Application Priority Data

Nov. 10, 2000 (DK) ......................... 2000 01682
Jan. 15, 2001 (DK) ......................... 2001 00057

(51) Int. Cl.[7] ............................. C12P 21/06
(52) U.S. Cl. ................................ 435/69.1
(58) Field of Search ................ 435/69.1; 514/2; 530/350, 387.1, 387.3

(56) References Cited

U.S. PATENT DOCUMENTS 5,408,038 A * 4/1995 Smith et al. ................. 530/359
5,876,968 A * 3/1999 Sirtori et al. ............... 435/69.7

FOREIGN PATENT DOCUMENTS

| WO | 8803166 | 5/1988 |
|----|---------|--------|
| WO | 9209893 | 6/1992 |
| WO | 9312143 | 6/1993 |
| WO | 9916459 | 4/1999 |

OTHER PUBLICATIONS

Sirtori et al, *Recombinant apolipoproteins for the treatment of vascular disease*, Atherosclerosis, vol. 142, pp. 29–40, Jan. 1999.

Kluft, et al., *Functional Analogy Between Lipoprotein(a) and Plasminogen in the Binding to the Kringle 4 Binding Protein, Tetranectin*, Biochemical and Biophysical Research Communications, vol. 161, No. 2, pp. 427–433, Jun. 15, 1989.

* cited by examiner

Primary Examiner—Jon Weber
Assistant Examiner—Sheridan K Snedden
(74) Attorney, Agent, or Firm—Iver P. Cooper

(57) ABSTRACT

The invention relates to a pharmaceutical composition comprising an apolipoprotein construct, to an apolipoprotein construct, a nucleic acid sequence encoding the apolipoprotein construct, a vector comprising the nucleic acid sequence, a method for producing the apolipoprotein construct, and a method of treatment comprising administering the apolipoprotein construct. The presented data document that the constructs according to the invention are capable of binding lipids, are capable of binding cubilin, which is a strong Apo AI receptor, stronger than native Apo A-I and that the plasma half life of the constructs is at least tripled compared to native Apo A-I. Together these data document that the constructs according to the invention are strong candidates for treatment of cardiovascular diseases.

54 Claims, 23 Drawing Sheets

Fig. 1

SQ SEQUENCE 267 AA; 30778 MW; 1A28B8366E620310 CRC64;

MKAAVLTLAV LFLTGSQARH FWQQDEPPQS PWDRVKDLAT VYVDVLKDSG RDYVSQFEGS

ALGKQLNLKL LDNWDSVTST FSKLREQLGP VTQEFWDNLE KETEGLRQEM SKDLEEVKAK

VQPYLDDFQK KWQEEMELYR QKVEPLRAEL QEGARQKLHE LQEKLSPLGE EMRDRARAHV

DALRTHLAPY SDELRQRLAA RLEALKENGG ARLAEYHAKA TEHLSTLSEK AKPALEDLRQ

GLLPVLESFK VSFLSALEEY TKKLNTQ

Fig. 2a.1

```
HUMAN           MKAAVLTLAVLFLTGSQARHFWQQDEPPQSPWDRVKDLATVYVDVLKDSGRDYVSQFEGS
Macaque         MKATVLTLAVLFLTGSQARHFWQQDEPPQTPWDRVKDLVTVYVEALKDSGKDYVSQFEGS
Bovine          MKAVVLTLAVLFLTGSQARHFWQQDDP-QSSWDRVKDFATVYVEAIKDSGRDYVAQFEAS
Pig             MKAVVLTLAVLFLTGSQARHFWQQDDP-QSPWDRVKDFATVYVDAIKDSGRDYVAQFEAS
Dog             MKAALLTLAVLFLTGSQARHFWQQDEP-QSPWDRVKDLATVYVDAVKDSGRDYVAQFEAS
Rabbit          MKAVVLTLAVLFLTGSQARHFWQRDEP-RSSWDKIKDFATVYVDTVKDSGREYVAQFEAS
Tree shreew     MKAVVLTLAVLFLTGSQARHFWQQDEP-QSSWDRVRDLANVYVDAVKESGREYVSQLEAS
Mouse           MKAVVLAVALVFLTGSQAWHVWQQDEP-QSQWDKVKDFANVYVDAVKDSGRDYVSQFESS
Rat             MKAAVLAVALVFLTGCQAWEFWQQDEP-QSQWDRVKDFATVYVDAVKDSGRDYVSQFESS
Eur. Hedgehog   ----------------------DEA-KSYWDQIKDMLTVYVDTAKDSGKDYLTSLDTS
Chicken         MRGVLVTLAVLFLTGTQARSFWQHDEP-QTPLDRIRDMVDVYLETVKASGKDAIAQFESS
Jap. quail      MRGVLVTLAVLFLTGTQARSFWQHDDP-QTPLDRIRDMLDVYLETVKASGKDAISQFESS
Domestic duck   MRVVVVTLALLFLTGTQARYFWQHDEP-QAPLDRLRDLVDVYLETVKASGKDAIAQFEAS
Rainbow trout   MKFLALALTILLAAGTQAFP-MQADAP--SQLEHVKAALSMYIAQVKLTAQRSIDLLDDT
Brown trout     MKFLALALTILLAAATQAVP-MQADAP--SQLEHVKVAMMEYMAQVKETGQRSIDLLDDT
Atl. salmon     MKFLVLALTILLAAGTQAFP-MQADAP--SQLEHVKAALNMYIAQVKLTAQRSIDLLDDT
Zebrafish       MKFVALALTLLLALGSQANL-FQADAP--TQLEHYKAAALVYLNQVKDQAEKALDNLDGT
Sea bream       MKFAALALALLLAVGSHAAS-MQADAP--SQLDHARAVLDVYLTQVKDMSLRAVNQLDDP
                                        *  . :  :: :    *:   *   .   : :: .

HUMAN           ALGKQLNLKLLDNWDSVTSTFSKLREQLGPVTQEFWDNLEKETEGLRQEMSKDLEEVKAK
Macaque         ALGKQLNLKLLDNWDSVTSTVSKLREQLGPVTQEFWDNLEKETEGLRQEMSKDLEEVKAK
Bovine          ALGKQLNLKLLDNWDTLASTLSKVREQLGPVTQEFWDNLEKETASLRQEMHKDLEEVKQK
Pig             ALGKHLNLKLLDNWDSLGSTFTKVREQLGPVTQEFWDNLEKETEALRQEMSKDLEEVKKK
Dog             ALGKQLNLKLLDNWDSLSSTVTKLREQIGPVTQEFWDNLEKETEVLRQEMSKDLEEVKQK
Rabbit          AFGKQLNLKLLDNWDSLSSTVSKLQEQLGPVTQEFWDNLEKETEGLREEMNKDLQEVRQK
Tree shreew     ALGKQLNLKLVDNWDTLGSTFQKVHEHLGPVAQEFWEKLEKETEELRREINKDLEDVRQK
Mouse           SLGQQLNLNLLENWDTLGSTVSQLQERLGPLTRDFWDNLEKETDWVRQEMNKDLEEVKQK
Rat             TLGKQLNLNLLDNWDTLGSTVGRLQEQLGPVTQEFWANLEKETDWLRNEMNKDLENVKQK
Eur. Hedgehog   ALGQQLNKKLADNWDTVSSALLKAREQMKPIAMEFWGNLEKDTEGLRQTVSKDLELVKEK
Chicken         AVGKQLDLKLADNLDTLSAAAAKLREDMAPYYKEVREMWLKDTEALRAELTKDLEEVKEK
Jap. quail      AVGKQLDLKLADNLDTLSAAAAKLREDMTPYYREVREMWLKDTEALRAELTKDLEEVKEK
Domestic duck   AVGKQLDLKLADNLDTLGAAAAKLREDMAPYYKEVREMWLKDTESLRAELTKDLEEVKEK
Rainbow trout   EY-KEYKMQLTQSLDNLQQYADATSQSLAPYSEAFGTQLTDATAAVRAEVMKDVEELRSQ
Brown trout     EF-KEYKVQLSQSLDNLQQYAQTTSQSLAPYSEAPGAQLTDAAAAVRAEVMKDVEDVRTQ
Atl. salmon     EY-KEYKMQLSQSLDNLQQFADSTSKSWPPTPRSS-APSCDATATVRAEVMKDVEDVRTQ
Zebrafish       DY-EQYKLQLSESLTKLQEYAQTTSQALTPYAETISTQLMENTKQLRERVMTDVEDLRSK
Sea bream       QY-AEFKTNLAQRIEEMYTQIKTLQGSVSPMTDSFYNTVMEVTKDTRESLNVDLEALKSS
                   ..:* :      :           *         . :   *  :   *:: :: .

HUMAN           VQPYLDDFQKKWQEEMELYRQKVEPLRAELQEGARQKLHELQEKLSPLGEEMRDRARAHV
Macaque         VQPYLDDFQKKWQEEMELYRQKVEPLRAELHEGTRQKLHELHEKLSPLGEEVRDRARAHV
Bovine          VQPYLDEFQKKWHEEVEIYRQKVAPLGEEFREGARQKVQELQDKLSPLAQELRDRARAHV
Pig             VQPYLDDFQNKWQEEMETYRQKMAPLGAEFREGARQKVQELQEKLSPLAEELRDRLRAHV
Dog             VQPYLDDFQKKWQEEVELYRQKVAPLGSELREGARQKLQELQEKLSPLAEELRDRARTHV
Rabbit          VQPYLDEFQKKWQEEVERYRQKVEPLGAELRESARQKLTELQEKLSPLAEELRDSARTHV
Tree shrew      TQPFLDEIQKKWQEDLERYRQKVEPLSAQLREGARQKLMELQEQVTPLGEDLRDSVRAYA
Mouse           VQPYLDEFQKKWKEDVELYRQKVEAPLGAELQESARQKLQELQGRLSPVAEEFRDRMRTHV
Rat             MQPHLDEFQEKWNEEVEAYRQKLEPLGTELHKNA----KEMQRHLKVVAEEFRDRMRVNA
Eur. Hedgehog   VQPYLDSFQKKVEEELELYRQKVAPLSAEWREQARQKAQELQQKAGELGQQHRDRVRTHV
Chicken         IRPFLDQFSAKWTEELEQYRQRLTPVAQELKELTKQKVELMQAKLTPVAEEARDRLRGHV
Jap. quail      IRPFLDQFSAKWTEEVEQYRQRLAPVAQELKDLTKQKVELMQAKLTPVAEEVRDRLREQV
Domestic duck   IRPFLDQFSAKWTEELEQYRQRLAPVAEELKELTKQKVELMQQKLTPVAEEARDRLRGHV
Rainbow trout   LEPKRAELKEVLDKHIDEYRKKLEPLIKEHIELRRTEMEAFRAKMEPIVEELRAKVAINV
Brown trout     LEPKRAELKEVLDKHIDEYRKKLEPLIKEIVEQRRTELEAFRVKMEPVVEEMRAKVSTNV
Atl. salmon     LEPKRAELTEVLNKHIDEYRKKLEPLIKQHIELRRTEMDAFRAKIDPVVEEMRAKVAVNV
Zebrafish       LEPHRAELYTALQKHIDEYREKLEPVFQEYSALNRQNAEQLRAKLEPLMDDIRKAFESNI
Sea bream       LAPQNEQLKQVIEKHLNDYRTLLTPIYNDYKTKHDEEMAALKTRLEPVMEELRTKIQANV
                 *   .:     :..:: ** : *:  :         :: :::    : ::  *
```

Fig. 2a.2

```
HUMAN           DALRTHLAPYSDELRQRLAARLEALKENGGARLAEYHAKATEHLSTLSEKAKPALEDLRQ
Macaque         DALRTHLAPYSDELRQRLAARLEALKENGGARLAEYHAKASEHLSTLSEKAKPALEDLRQ
Bovine          ETLRQQLAPYSDDLRQRLTARLEALKEGGG-SLAEYHAKASEQLKALGEKAKPVLEDLRQ
Pig             EALRQHVAPYSDDLRQRMAARFEALKEGGG-SLAEYQAKAQEQLKALGEKAKPALEDLRQ
Dog             DALRAQLAPYSDDLRERLAARLEALKEGGGASLAEYHARASEQLSALGEKARPALEDLRQ
Rabbit          DTLRTKLAPYSNELQQRLAARLESIKEGGGASLAEYQAKAREHLSVLSEKARPALEDLRQ
Tree shreew     DTLRTQLAPYSEQMRKTLGARLEAIKEGGSASLAEYHAKASEQLSALGEKAKPVLEDIHQ
Mouse           DSLRTQLAPHSEQMRESLAQRLAELKSNP--TLNEYHTRAKTHLKTLGEKARPALEDLRH
Rat             DALRAKFGLYSDQMRENLAQRLTEIRNHP--TLIEYHTKAGDHLRTLGEKAKPALDDLRH
Eur. Hedgehog   DALRTDLAPYGEEARKLLLQRLQDIKAKSG-DLAEYQTKLSEHLKSFGEKAQPTLQDLRH
Chicken         EELRKNLAPYSDELRQKLSQKLEEIREKGIPQASEYQAKVMEQLSNLREKMTPLVQEFRE
Jap. quail      EELRKNLAPYSSELRQKLSQKLEEIRERGIPQASEYQAKVVEQLSNLREKMTPLVQEFKE
Domestic duck   EELRKNLAPYSDELRQKLSQKLEEIREKGIPQAAEYQAKVVEQLSNLREKMTPLVQDFKE
Rainbow trout   EETKTKLMPIVEIVRAKLTERLEELRTLAAPYAEEYKEQMIKAVGEVREKVSPLSEDFKG
Brown trout     EETKAKLMPIVETVRAKLTERLEELRTLAAPYAEEYKEQMFKAVGEVREKVGPLTNDFKG
Atl. salmon     EETKTKLMPIVEIVRAKLTERLEELRTLAAPYAEEYKEQMFKAVGEVREKVAPLSEDFKA
Zebrafish       EETKSKVVPMVEAVRTKLTERLEDLRTMAAPYAEEYKEQLVKAVEEAREKIAPHTQDLQT
Sea bream       EETKAVLMPMVETVRTKVTERLESLREVVQPYVQEYKEQMKQMYDQA-QTVD--TDALRT
                 :   :  .  .   :   :  ::   ::       **: :          :.    : :

HUMAN           GLLPVLESFKVSFLSALEEYTKKLNTQ
Macaque         GLLPVLESFKVSFLSALEEYTKKLSTQ
Bovine          GLLPVLESLKVSILAAIDEASKKLNAQ
Pig             GLLPVLENLKVSILAAIDEASKKLNAQ
Dog             GLLPVLESFKVSLLAAIDEATKKLNAQ
Rabbit          GLLPVLESFKASVQNVLDEATKKLNTQ
Tree shreew     GLMPMWESFKTGVLNVIDEAAKKLTA-
Mouse           SLMPMLETLKTKAQSVIDKASETLTAQ
Rat             GLMPVLEAWKAKIMSMIDEAKKKLNA-
Eur. Hedgehog   GLEPLWEGIKAGAMSMLEELGKKLNSQ
Chicken         RLTPYAENLKNRLISFLDELQKSVA--
Jap. quail      RLTPYAENLKNRLIDLLDEVQKTMA--
Domestic duck   RLTPYAENLKTRFISLLDELQKTVA--
Rainbow trout   QVGPAAEQAKQKLLAFYETISQAMKA-
Brown trout     QVGPAAEQAKEKLMDFYETISQAMKA-
Atl. salmon     RWAPPPRRPSK--SSWLSTRPSARP--
Zebrafish       RMEPYMENVRTTFAQMYETIAKAIQA-
Sea bream       KITPLVEEIKVKMNAIFEIIAASVTKS
                        *        .    .
```

Fig. 2b

```
sp|P06727|APA4_HUMAN    MFLKAVVLTLALVAVAGARAEVSADQVATVMWDYFSQLSNNAKEAVEHLQKSELTQQLNA  60
sp|P33621|APA4_MACFA    MFLKAVVLTLALVAVTGARAEVSADQVATVMWDYFSQLSSNAKEAVEHLQKSELTQQLNA  60
sp|P06728|APA4_MOUSE    MFLKAAVLTLALVAITGTRAEVTSDQVANVVWDYFTQLSNNAKEAVEQFQKTDVTQQLST  60
sp|Q28758|APA4_PAPAN    ---------------GARAEVSADQVATVMWDYFSQLSSNAKEAVEHLQKSELTQQLNA  44
sp|O46409|APA4_PIG      MFLKAVVLSLALVAVTGARAEVNADQVATVMWDYFSQLGSNAKKAVEHLQKSELTQQLNT  60
sp|P02651|APA4_RAT      MFLKAVVLTVALVAITGTQAEVTSDQVANVMWDYFTQLSNNAKEAVEQLQKTDVTQQLNT  60
                                       *::***.:****.*:****:**..***:***::**:;:****.:

sp|P06727|APA4_HUMAN    LFQDKLGEVNTYAGDLQKKLVPFATELHERLAKDSEKLKEEIGKELEELRARLLPHANEV 120
sp|P33621|APA4_MACFA    LFQDKLGEVNTYAGDLQKKLVPFATELHERLAKDSEKLKEEIRKELEEVRARLLPHANEV 120
sp|P06728|APA4_MOUSE    LFQDKLGDASTYADGVHNKLVPFVVQLSGHLAKETERVKEEIKKELEDLRDRMMPHANKV 120
sp|Q28758|APA4_PAPAN    LFQDKLGEVNTYAGDLQKKLVPFATELHERLAKDSKKLKEEIRKELEEVRARLLPHANEV 104
sp|O46409|APA4_PIG      LFQDKLGEVNTYTEDLQKKLVPFATELHERLTKDSEKLKEEIRRELEELRARLLPHATEV 120
sp|P02651|APA4_RAT      LFQDKLGNINTYADDLQNKLVPFAVQLSGHLTKETERVREEIQKELEDLRANMMPHANKV 120
                        *****: .: .:::*****..:* :*:*::::::* :*:* .::***.:* sp|P06727|APA4_HUMAN    SQKIGDNLRELQQRLEPYADQLRTQVNTQAEQLRRQLTPYAQRMERVLRENADSLQASLR 180
sp|P33621|APA4_MACFA    SQKIGENVRELQQRLEPYTDQLRTQVNTQTEQLRRQLTPYAQRMERVLRENADSLQTSLR 180
sp|P06728|APA4_MOUSE    TQTFGENMQKLQEHLKPYAVDLQDQINTQTEMKLQLTPYIQRMQTTIKENVDNLHTSMM  180
sp|Q28758|APA4_PAPAN    SQKIGENVRELQQRLEPYTDQLRTQVNTQTEQLRRQLTPYAQRMERVLRENADSLQTSLR 164
sp|O46409|APA4_PIG      SQKIGDNVRELQQRLGPFTGGLRTQVVQQLQRQLKPYAERMESVLRQNIRNLEASVA    180
sp|P02651|APA4_RAT      SQMFGDNVQKLQEHLRPYATDLQAQINAQTQDMKRQLTPYIQRMQTTIQDNVENLQSSMV 180
                        :*  :*::*::**::* *::  *: *:*:*.::::: **.** :** ...:*  .*.:*:

sp|P06727|APA4_HUMAN    PHADELKAKIDQNVEELKGRLTPYADEFKVKIDQTVEELRRSLAPYAQDTQEKLNHQLEG 240
sp|P33621|APA4_MACFA    PHADQLKAKIDQNVEELKERLTPYADEFKVKIDQTVEELRRSLAPYAQDAQEKLNHQLEG 240
sp|P06728|APA4_MOUSE    PLATNLKDKFNRNMEELKGHLTPRANELKATIDQNLEDLRRSLAPLTVGVQEKLNHQMEG 240
sp|Q28758|APA4_PAPAN    PHADQLKAKIDQNVEELKGRLTPYADEFKVKIDQTVEELRRSLAPYAQDAQEKLNHQLEG 224
sp|O46409|APA4_PIG      PYADEFKAKIDQNVEELKGSLTPYAEELKAKIDQNVEELRRSLAPYAQDVQEKLNHQLEG 240
sp|P02651|APA4_RAT      PFANELKEKFNQNMEGLKGQLTPRANELKATIDQNLEDLRSRLAPLAEGVQEKLNHQMEG 240
                        * * ::* *:::*:* ** ***  *:*:*..***.:*:** *** : ..*******:**

sp|P06727|APA4_HUMAN    LTFQMKKNAEELKARISASAEELRQRLAPLAEDVRGNLKGNTEGLQKSLAELGGHLDQQV 300
sp|P33621|APA4_MACFA    LAFQMKKNAEELKARISASAEELRQRLAPLAEDMRGNLRGNTEGLQKSLAELGGHLDRHV 300
sp|P06728|APA4_MOUSE    LAFQMKKNAEELQTKVSAKIDQLQKNLAPLVEDVQSKVKGNTEGLQKSLEDLNRQLEQQV 300
sp|Q28758|APA4_PAPAN    LAFQMKKNAEELKARISASAEELRQRLAPLAEDMRGNLRGNTEGLQKSLAELGGHLDRHV 284
sp|O46409|APA4_PIG      LAFQMKKQAEELKAKISANADELRQRLVPVAENVHGHLKGNTEGLQKSLLELRSHLDQQV 300
sp|P02651|APA4_RAT      LAFQMKKNAEELQTKVSTNIDQLQKNLAPLVEDVQSKLKGNTEGLQKSLEDLNKQLDQQV 300
                        *:;***:**:::.*:: ..:*::.*.*::.*:;:.:::::********* :* :*::* sp|P06727|APA4_HUMAN    EEFRRRVEPYGENFNKALVQQMEQLRQKLGPHAGDVEGHLSFLEKDLRDKVNSFFSTFKE 360
sp|P33621|APA4_MACFA    EEFRLRVEPYGENFNKALVQQMEQLRQKLGPHAGDVEGHLSFLEKDLRDKVNSFFSTFKE 360
sp|P06728|APA4_MOUSE    EEFRRTVEPMGEMFNKALVQQLEQFRQQLGSGEVESHLSFLEKSLREKVNSFMSTLEK  360
sp|Q28758|APA4_PAPAN    EEFRLRVEPYGENFNKALVQQMEQLRQKLGPHAGDVEGHLSFLEKDLRDKVNSFFSTFKE 344
sp|O46409|APA4_PIG      EEFRLKVEPYGETFNKALVQQVEDLRQKLGPLAGDVEGHLSFLEKDLRDKVNTFFSTLKE 360
sp|P02651|APA4_RAT      EVFRRAVEPLGDKFNMALVQQMEKFRQQLGSDSGDVESHLSFLEKNLREKVSSFMSTLQK 360
                        * ** *** *: ** *****:*.:**:**. :*:**.*******.**:**.:*:**:::

sp|P06727|APA4_HUMAN    KESQDKTLSLPEL----EQQQEQQQ-------------------------EQ 383
sp|P33621|APA4_MACFA    KESQDNTLSLPEP----EQQREQQQEQQEQEQEQQQQQEQQQQQEQQREQQQEQQQEQ 416
sp|P06728|APA4_MOUSE    KGSPDQPQALPLPEQAQEQAQEQAQEQVQ------------------------- 389
sp|Q28758|APA4_PAPAN    KESQDNTLSLPEP----EQQQEQQQEQEQ-----QQEQQEEQQQQEQQ-------QEQEQ 388
sp|O46409|APA4_PIG      EASQGQSQALPAQ----EKAQ------------------------------- 377
sp|P02651|APA4_RAT      KGSPDQPLALPLP----EQVQEQVQEQVQ------------------------- 385
                        : * .:. :**       *: :

sp|P06727|APA4_HUMAN    QQEQVQMLAPLES 396
sp|P33621|APA4_MACFA    QQEQVQMLAPLES 429
sp|P06728|APA4_MOUSE    -------PKPLES 395
sp|Q28758|APA4_PAPAN    QQEQVQMLAPLES 401
sp|O46409|APA4_PIG      --------APLEG 382
sp|P02651|APA4_RAT      -------PKPLES 391
                               ***.
```

Fig. 3

Exon 1 — Trimer stabilising

Exon 2 — Tripple alpha helical coiled coil forming $E_1 P_2 P T Q K P K K I V N A K K D_{16} V_{17} V N T K M F E E L K S R L D T L A Q E V A L L K E Q Q A L Q T V C L_{51}$

Fig. 4

| Position | d e f g a b c d e f g | a b c d e f g | a b c d e f g a |
|---|---|---|---|
| Human tetranectin | V V N T K M F E E L K S R L D T L A Q E V A L L K E Q Q A L Q T V C L K |
| Murine tetranectin | L V S S K M F E E L K N R M D V L A Q E V A L L K E K Q A L Q T V C L K |
| Bovine cart. protein | R R V K E K D G D L K T Q V E K L W R E V N A L K E M Q A L Q T V C L R |
| Shark cart. protein | S K S G K G K D D L R N E I D K L W R E V N S L K E M Q A L Q T V C L K |
| Consensus | L  by L  E V  L K E  Q A L Q T V C L |

Fig. 5 pT7 H6UbiFx Apo A1 pBR328-(PvuII)-GATCTCGATCCCGCGAAATTAATACGACTCACTATAGGGAGACCACAACGTTTCCCTCTAGAAATAATTTTGTTTAACTTT
                                       T7 promoter
AAGAAGGAGATATACATATGGGATCGCATCACCATCACCATCACGGATCACAGATCTTTGTGAAGACCCTCACTGGCAAACCATCACCCTTG
              Nde I    M  G  S  H  H  H  H  H  H  G  S  Q  I  F  V  K  T  L  T  G  K  T  I  T  L
GAGGTCCAGCCCAGTGACACCATTGAAAATGTCAAAGCCAAAATTCAAGACAAGGAGGGTATCCCACCTGACCAGCGTCTGATATTTGCCG
 E  V  E  P  S  D  T  I  E  N  V  K  A  K  I  Q  D  K  E  G  I  P  P  D  Q  R  L  I  F  A
GCAAACAGCTGGAAGATGGACGTACTTTGTCTGACTACAATATTCAAAAGGAGTCTACTCTTCATCTTGTGTTGAGACTTCGTGGTGGATCCA
 G  K  Q  L  E  D  G  R  T  L  S  D  Y  N  I  Q  K  E  S  T  L  H  L  V  L  R  G  G  S
                                                                                  BamHI
TCGAGGGTAGGGGTGGAgatgaaccccccgcctgggatcgagtgaaggacctgccactgtgatgtactgtgatgtgctcaaagacagcggcagagac
 I E G R G D E P P Q S P W D R V K D L A T V V Y V D V L K D S G R D
tatgtgtcccagtttgaaggctccgcgcttgaccaggaagttctgggataacagcagcatcctcctgacaactggaacagacagaggcgtgacccactttcagcaagctg
 Y V S Q F E G S A L G K Q L N L K L L D N W D S V T S F S K L
cgcgaacagctcggccctgtgaccccagagttctgcagcgacttctggacgactttcagaagattccagacgtcttccacctggaagatgagcaaggatctgcggaggag
 R E Q L G P V T Q E F W D N L E K E T E G L R Q E M S K D L E E
gtgaaggccaaggtgcagcccctacctgaccgagaagctgcacgagctgcaagagaaagctgagccactgggcgaggagatgcgcgaccgcgcgcgcgcatgtg
 V K A K V Q P Y L D D F Q K K W Q E E M E L Y R Q K V E P L R A
gagctccaagagggccacgcatctgccccctacagcgagagctgcgccagcgtcgccagcgcttgaggcttcaaggagctctcaggagaacggcggccaga
 E L Q E G A R Q K L H E L Q E K L S P L G E E M R D R A R A H V
gacgcgctggcgcacgcatctgccccctacagcgagtaccttcagcgacagatcttgagcacgcatctgagcacctgagcacctacgagaccacggccgcaaggcctgctgccc
 D A L R T H L A P Y S D E L R Q R L A A R L E A L K E N G G A R
ctggccgagtactacacgccaaggccaccgagctcctgagcacgctccctgagcacctgagcacacgagctccgagcaggaaggccaaggcctcgagaccctccgcctgctgccc
 L A E Y H A K A T E H L S T L S E K A K P A L E D L R Q G L L P
gtgctggagagcttcaaggtcagctccgagcttcctgagcagtaccctccgaggagtacactaagaagctcaacaccagTAAGCATGCAAGCTTGAATTCCGATCC
 V L E S F K V S F L S A L E E Y T K K L N T Q STOP SphI HindIII EcoRI

GGCTGCTAACAAGCCCGAAAGGAAGCTGAGTTGGCTGCCTGCCACCGCTGAGCTGAGCAATAACTAGCATAACCCCTCTG

CCACCGCTGTGGGGCCTCTAAACGGGTCTTGAGGGGTTTTTGCTGAAAGGAGGAACTATATCCGAT-(EcoRV)-pBR328.

Fig. 6 pT7 H6ubiFx Cys-Apo A1

```
pBR328-(PvuII)-GATCTCGATCCCGCGAAATTAATACGATACACTATAGGAGACCACAACGGTTTCCCTCTAGAAATAATTTTGTTTAACTTT
                                        T7 promoter
AAGAAGGAGATATACATATGGGATCGCATCACCATCACCATCACGGATCTCTTTGTGAAGACCCTCACTGGCAAAACCATCACCCTTG
                  Nde I   M  G  S  H  H  H  H  H  H  G  S  Q  I  F  V  K  T  L  T  G  K  T  I  T  L
AGGTCGAGCCCAGTGACACCATTGAGAATGTCAAAGCCAAAATTCAAGACAAGGAGGGTATCCCACCTGACCAGCAGCGTCTGATATTTGCCG
 E  V  E  P  S  D  T  I  E  N  V  K  A  K  I  Q  D  K  E  G  I  P  P  D  Q  Q  R  L  I  F  A
GCAAACAGCTGGAAGATGGACGTACTTTGTCTGACTACAATATTCAAAAGGAGTCTACTCTTCATCTTGTGTTGAGACTTCGTGGTGGATCCA
 G  K  Q  L  E  D  G  R  T  L  S  D  Y  N  I  Q  K  E  S  T  L  H  L  V  L  R  L  R  G  G  S
                                                                                   BamHI
TCGAGGGGTAGGGGCTGCGATGTgatgaacccccccagagccctgggatcgagtgaaggaccctggccactgtgaagtgctcaaagacagcggcagagac
 I  E  G  R  G  G  C  D
tatgtcccagttcgaaggctccgccttgggaaaaacagctaaagctcccttgacaactgggacagcgtgacctccaccttcagcaagctg
 Y  V  S  Q  F  E  G  S  A  L  G  K  Q  L  N  L  K  L  L  D  N  W  D  S  V  T  S  T  F  S  K  L
cgcgaacagctcggcctgcccgtgactcaggagttctgaggagccagagggcctgagcaggagacagaggcctgaggcaggagatgagcaaggatctggaggag
 R  E  Q  L  G  P  V  T  Q  E  F  W  D  N  L  E  K  E  T  E  G  L  R  Q  E  M  S  K  D  L  E  E
gtgaaggccaaggtgcagccctacctggacgacttccagaagaagtggcaggaggagatggagctctaccgccagaaggtggagcgcgtgcgcgca
 V  K  A  K  V  Q  P  Y  L  D  D  F  Q  K  K  W  Q  E  E  M  E  L  Y  R  Q  K  V  E  P  L  R  A
gagctccaagagggcgcgcgccagaagctgcacgagctgcaagagaagctgagcccactgggcgagcccctggccgcgcgcctccaaggagaacgggcgccaga
 E  L  Q  E  G  A  R  Q  K  L  H  E  L  Q  E  K  L  S  P  L  G  E  E  M  R  D  R  A  R  A  H  V
gacgcgctgcgcacgcatctggcccccctacgaggagcatctgagcacgctgagcaccaccgccaagcccgcgagacctcgaggaccttcgccaaggcctgctgccc
 D  A  L  R  T  H  L  A  P  Y  S  D  E  L  R  Q  R  L  A  A  R  L  E  A  L  K  E  N  G  G  A  R
ctggccgagtaccacgccaaggccacggagcatctgagcacgctgagcgagaaggcaaagcccgcgcttgaggactgcgcgctggccgagggactgagggccctgcctgcgtgcca
 L  A  E  Y  H  A  K  A  T  E  H  L  S  T  L  S  E  K  A  K  P  A  L  E  D  L  R  Q  G  L  L  P
gtgctggagagcttcaaggtcagctttctgagcgctctcgaggagtacactaagaagctcaacacccagTAAGCATGCAAGCTTGAATTCCGATCC
 V  L  E  S  F  K  V  S  F  L  S  A  L  E  E  Y  T  K  K  L  N  T  Q  STOP SphI HindIII EcoRI
GGCTGCTAACAAAGCCCGAAAGGAAGCTGAGTTGGCTGCTGCCACCGCTGAGCTGAGCAATAACTAGCATAACCCCTCTG
CCACCGCTGTGGGGCCTCTAAACGGGTCTTGAGGGGTTTTTGCTGAAAGGAGGAACTATATCCGAT-(EcoRV)-pBR328.
```

Fig. 7 pT7H6 Trip-A-Apo A1 - Amp^R.

pBR328-(PvuII)-GATCTCGATCCGCGAAATTAATACGATACACTATAGGGAGACCACACGGTTTCCCTCTAGAAATAATTTGTTTAACTTTAAGAAGGAGAT
                                         T7 promoter
                                                                M  G  S  H  H  H  H  H  H  G  S  I  Q  G  R  S  P  G  T  E  P  P  T  Q  K  P  K  K  I  V  N  A  K  K
ATACATATGGGATCGCATCACCATCACCATCACGGATCCATCCAGGGTAGATCCTCCAGGGTACCGAGCCACCACCCAGAAGCCCAAGAAGATTGTAAATGCCAAGAAA
                             BamHI                Bgl II    Kpn I
 D  V  V  N  T  K  M  F  E  E  L  K  S  R  L  D  T  L  A  Q  E  V  A  L  L  K  E  Q  Q  A  L  Q  T  V  S  L
GATGTTGTGAACACAAAGATGTTTGAGGAGCTCAAGAGCCGTCTGGACACCCTGGCCCAGGAGGTGGCCCTGCTGAAGGAGCAGCAGGCCCTGCAGACGGTCTCCCTG
 K  G  S  D  E  P  P  Q  S  P  W  D  R  V  K  D  L  A  T  V  Y  V  D  V  L  K  D  S  G  R  D
AAGGGATCCgatgaaccccccagagcccctggagtcgagtgaaggaccctggccactgtgtacgtggatgtgctcaaagacagcggcagagac
 Y  V  S  Q  F  E  G  S  A  L  G  K  Q  L  N  L  K  L  L  D  N  W  D  S  V  T  S  T  F  S  K  L
tatgtgtcccagtttgaaggctccgccttgggcaaacagctaaacctgaaagtctcttgacaactgggacagcgtgacctccacttcagcaagctg
 R  E  Q  L  G  P  V  T  Q  E  F  W  D  N  L  E  K  E  T  E  G  L  R  Q  E  M  S  K  D  L  E  E
cgcgaacagctcggcccctgtgacccaggagttctgaccaggagttctgggataacctggagaaagagacagaggcctgagcgcaggagatgagcaaggatctggaggag
 V  K  A  K  V  Q  P  Y  L  D  D  F  Q  K  K  W  Q  E  E  M  E  L  Y  R  Q  K  V  E  P  L  R  A
gtgaaggccaaggtgcagccctacctggacgactttcagaaaagtggcaggaggagatggagctctacaggcagaaggtggagccgctgcgcgca
 E  L  Q  E  G  A  R  Q  K  L  H  E  L  Q  E  K  L  S  P  L  G  E  E  M  R  D  R  A  R  A  H  V
gagctccaagagggcgcgcgccagaagctgcacgagctgcaagagaagctgagccactgggcgaggagatgcgcgaccgcgcgcgcgcccatgtg
 D  A  L  R  T  H  L  A  P  Y  S  D  E  L  R  Q  R  L  A  A  R  L  E  A  L  K  E  N  G  G  A  R
gacgcgctgcgcacgcatctcgcccccatcccacggagagctgagcagccgctggccgcagcgcttggccgccagcctgaaggctctcaaggagaacggcggcgcaga
 L  A  E  Y  H  A  K  A  T  E  H  L  S  T  L  S  E  K  A  K  P  A  L  E  D  L  R  Q  G  L  L  P
ctggccgagtaccacgccaaggccacgagcatctgagcgacgcatcagcgagctctcaggagaaggccaagccgctcgaggacctgcgccaaggcctgctgccc
 V  L  E  S  F  K  V  S  F  L  S  A  L  E  E  Y  T  K  K  L  N  T  Q  STOP HindIII EcoRI
gtgctggagagcttcaaggtgtcagcttcctgagcgctctgaggagtacactaagaagctacactaagaagctacaacaccccagTAATAAGCTTGAATTCCGGCTGCTAA CAAAGCCCGAAAGGAAGCTGAGTTGGCTGCCTGCCACCGCTGAGCTGAGCAATAACTAGCATAACCCCTCTGCCACCCCTGTGGGCCCTCTAAACGGGTCTTGAGGGG
TTTTTGCTGAAAGGAGGAACTATATCCGAT-(EcoRV)-pBR328.

Fig. 8 pT7H6 Trip-A-Apo A1-del143 - Amp^R.

```
pBR328-(PvuII)-GATCTCGATCCCGCGAAATTAATACGATACACTATAGGGAGACCACAACGTTTCCCTCTAGAAATAATTTTGTTTAACTTTAAGAAGGAGAT
                                          T7 promoter
                  M  G  S  H  H  H  H  H  H  G  S  I  Q  G  R  S  P  G  T  E  P  P  P  T  Q  K  P  K  K  I  V  N  A  K  K
ATACATATGGGATCGCATCACCATCACCATCACGGATCGATCCAGGGTAGATCTCCTGGTACGGAGCCACCAACCCAGAAGCCCAAGAAGATTGTAAATGCCAAGAAA
                 BamHI                          BglII  KpnI
 D  V  V  N  T  K  M  F  E  E  L  K  S  R  L  D  T  L  A  Q  E  V  A  L  L  K  E  Q  Q  A  L  Q  T  V  S  L
GATGTTGTGAACACAAAGATGTTTGAGGAGCTCAAGAGCCGTCTGGACACCCTGGCCCAGGAGGTGGCCCTGCTCAAGGAGCAGCAGGCCCTGCAGACGGTCTCCCTG
AAGGGATCCctaaagctccctgacaactgggacagcgtgacctccaccttcagcaagctg
 K  G  S  L  K  L  L  D  N  W  D  S  V  T  S  T  F  S  K  L
cgcgaacagctcggcctgtgacccaggagttctgggataacctggaaaaggagacagagggctgaggcaggagatgagcaggatctggaggag
 R  E  Q  L  G  P  V  T  Q  E  F  W  D  N  L  E  K  E  T  E  G  L  R  Q  E  M  S  K  D  L  E  E
gtgaaggccaaggtgcagcccctacctggacgactccagaagaagtggcaggaggagatggcagagtgctctaccgccagaagtggagcccgctgcgcgca
 V  K  A  K  V  Q  P  Y  L  D  D  F  Q  K  K  W  Q  E  E  M  E  L  Y  R  Q  K  V  E  P  L  R  A
gagctccaagagggcgcgcgcccagaaactctgcacgagctgcacgagtgtgagaagctgagccccactgggcgaggagaagctgagccctgggcgagatgcgcgaccgcgcgcccatgtg
 E  L  Q  E  G  A  R  Q  K  L  H  E  L  Q  E  K  L  S  P  L  G  E  E  M  R  D  R  A  R  A  H  V
gacgcgctgcgcgtcacgcatctggcccccctacagcgagcctgcgcagcggctcgcggcccgcgaggagcccgagaacgcgcagagggcgcggccaga
 D  A  L  R  T  H  L  A  P  Y  S  D  E  L  R  Q  R  L  A  A  R  L  E  A  L  K  E  N  G  G  A  R
ctggccgagtaccacgccaaggccacggagcatctgagcacgtccagcgagaaggccaagccctcccgagagcctgctgccgccaaggcctgcctgccc
 L  A  E  Y  H  A  K  A  T  E  H  L  S  T  L  S  E  K  A  K  P  A  L  E  D  L  R  Q  G  L  L  P
gtgctggagagcttcaaggtcagctccgagcgctccgaggagtacactaaggaagctcaacacccagTAATAAGCTTGAATTCGATCCGGCTGCTAA
 V  L  E  S  F  K  V  S  F  L  S  A  L  E  E  Y  T  K  K  L  N  T  Q  STOP HindIII EcoRI
CAAAGCCCGAAAGGAAGCTGAGTTGGCTGCCTGCCACCGCTGCCACCGCTGAGCTGAGCAATAACTAGCATAACCCCTCTGCCACCCGTCTGTGGGCCTCTAAACGGGTCTTGAGGGG
TTTTTTGCTGAAAGGAGGAACTATATCCGAT-(EcoRV)-pBR328.
```

Fig. 9 pT7 H6Fx Cys-Apo A1 pBR328-(PvuII)-GATCTCGATCCCGCGAAATTAATACGACTCACTATAGGGAGACCACAACGGTTTCCCTCTAGAAATAATTTTGTTTAACTTTAAGAAGGAGATATA
                                T7 promoter

```
         M  G  S  H  H  H  H  H  H  G  S  I  E  G  R
CATATGGGATCGCATCACCATCACCATCACGGATCCATCGAGGGTAGG
Nde I                           Bam HI
```

```
GGTGGATGTgatgaaccccccagagcccctggatcgagtgaaggacctggccactgtgtacgtggatgtgctcaaagacagcggcagagac
 G  G  D  V  D  E  P  P  Q  S  P  W  D  R  V  K  D  L  A  T  V  Y  V  D  V  L  K  D  S  G  R  D
tatgtgtcccagtttgaaggctccgcgcttggaaaaacagctaaactcctcgacagcgtgacctccacctcagcaagctg
 Y  V  S  Q  F  E  G  S  A  L  G  K  Q  L  N  L  K  L  L  D  N  W  D  S  V  T  S  T  F  S  K  L
cgcgaacagctcggcccctgtgaccccaggagttctgggataacctggaaaaggagacagaggggctgaggcagaaggatgagcaaggatctggaggag
 R  E  Q  L  G  P  V  T  Q  E  F  W  D  N  L  E  K  E  T  E  G  L  R  Q  E  M  S  K  D  L  E  E
gtgaaggccaaggtgcagcccctaccctggacttccagagaagactggcagagctgcaggaaggccagaagcgtccagcagaaggtggagccgctgcgcgca
 V  K  A  K  V  Q  P  Y  L  D  D  F  Q  K  K  W  Q  E  E  M  E  L  Y  R  Q  K  V  E  P  L  R  A
gagctccaagagggcgcgcgcagaagctgcacgagcaggtgcaagagaagctctctcccagccttggcccgcgcgcgcgacccggcgcgccatgtg
 E  L  Q  E  G  A  R  Q  K  L  H  E  L  Q  E  K  L  S  P  L  G  E  E  M  R  D  R  A  R  A  H  V
gacgcgctgcgcacgcatctggcccccctacagccgagcatctgagcgaccgctcagcaagagacctcgagggcgcctgcgcc
 D  A  L  R  T  H  L  A  P  Y  S  D  E  L  R  Q  R  L  A  A  R  L  E  A  L  K  E  N  G  G  A  R
ctggccgagtaccacgccaaggccacggagcatcctgagcgtctcagcgagaaggccaaagcccaagccctccgccaaggctgcctgcctgccc
 L  A  E  Y  H  A  K  A  T  E  H  L  S  T  L  S  E  K  A  K  P  A  L  E  D  L  R  Q  G  L  L  P
gtgctggagagcttcaaggtcagtttcctgagcgctctgagggtaactaagaagtacactaagaagctcaacacccagTAAGCATGCAAGCTTGAATTCCGATCC
 V  L  E  S  F  K  V  S  F  L  S  A  L  E  E  Y  T  K  K  L  N  T  Q STOP SphI HindIII EcoRI
```

GGCTGCTAACAAAGCCCGAAAGGAAGCTGAGTTGGCTGCTGCCCTGAGCTGAGCAATAACTAGCATAACCCCTCTG
CCACCGCTGTGGGCCTCTAAACGGGTCTTGAGGGGTTTTTTGCTGAAAGGAGGAACTATATCCGAT-(EcoRV)-pBR328.

Fig. 10a pT7H6 Trip-A-Apo A1 K9A K15A - Amp^R.

```
pBR328-(PvuII)-GATCTCGATCCGCGAAATTAATACGATACACTATAGGAGACCACAACGGTTTCCCTCTAGAAATAATTTTGTTTAACTTTAAGAAGGAGAT
                                  T7 promoter
                          M  G  S  H  H  H  H  H  H  G  S  I  Q  G  R  S  P  G  T  E  P  P  T  Q  K  P  K  A  I  V  N  A  K  A
ATACATATGGGATCCATCATCACGATCATCACGGTAGATCTCCTGGTACCGAGCCCACCAACCCAGAAGCCCAAGGCGATTGTAAATGCCAAGGCA
                   Bam HI                    Bgl II     Kpn I
 D  V  V  N  T  K  M  F  E  E  L  K  S  R  L  D  T  L  A  Q  E  V  A  L  L  K  E  Q  Q  A  L  Q  T  V  S  L
GATGTTGTGAACACCAAAGATGTTTGAGGAGCTCAAGAGCCGTCTCGACACCCTGGCCCAGGAGGTGGCCCTGCTGAAGGAGCAGCAGGCCCTGCAGACGGTCTCCCTG
AAGGGATCCgatgaacccccccagagctggaagcctcggcagcccctgggatcgagtgaaggaccctggccactgtgtacgtggatgtgctcaaagacagcggcagagac
 K  G  S  D  E  P  P  Q  S  P  W  D  R  V  K  D  L  A  T  V  Y  V  D  V  L  K  D  S  G  R  D
tatgtgtcccagtttgaaggctccgcgcttggaccccaggagttctgaccaactgggacagcgtgacctccaccttcagcaagctg
 Y  V  S  Q  F  E  G  S  A  L  G  K  Q  L  N  L  K  L  L  D  N  W  D  S  V  T  S  T  F  S  K  L
cgcgaacagctcggcccctgtgaccaggagttctgaccccaggagtctgaggcagagatgagcaaggatctggaggatctgaggag
 R  E  Q  L  G  P  V  T  Q  E  F  W  D  N  L  E  K  E  T  E  G  L  R  Q  E  M  S  K  D  L  E  E
gtgaaggccaaggtgcagccgcggcagcccctacctggacgacttcctggaggacttcgccagaagaggtggagccgctgcgcgca
 V  K  A  K  V  Q  P  Y  L  D  D  F  Q  K  K  W  Q  E  E  M  E  L  Y  R  Q  K  V  E  P  L  R  A
gagctccaagagggcgcgcaggccaagctgcacgagctgcaagagaagctgagccccactgggcgaggagatgcgcgaccgcgcgcccatgtg
 E  L  Q  E  G  A  R  Q  K  L  H  E  L  Q  E  K  L  S  P  L  G  E  E  M  R  D  R  A  R  A  H  V
gacgcgctgcgcacgcatctctggcccccctacaccgagctgcgccagcgcctggccgcccgcctgaaggaggacctcgcgctgccgc
 D  A  L  R  T  H  L  A  P  Y  S  D  E  L  R  Q  R  L  A  A  R  L  E  A  L  K  E  N  G  G  A  R
ctgaccgagtacctacgccaaggccaccgagcatctgagcacgcagtgagtccctctggagagtgaacaccccaggccatataagctttgaattcgatccggctgccc
 L  A  E  Y  H  A  K  A  T  E  H  L  S  T  L  S  E  K  A  K  P  A  L  E  D  L  R  Q  G  L  L  P
gtgctggagagcttcaaggtcagtttcctgagcgctctcgaggagtacactaagagtcaacacccagTAATAAGCTTGAATTCGATCCGGCTGCTAA
 V  L  E  S  F  K  V  S  F  L  S  A  L  E  E  Y  T  K  K  L  N  T  Q  STOP HindIII EcoRI
CAAAGCCCGAAAGGAAGCTGAGTTGGCTGCCGCCACCGCTGAGCTGAGCAATAACTAGCATAACCCCTCTGCCACCGCTGTGGGGCCTCTAAACGGGTCTTGAGGGG
TTTTTGCTGAAGGAGGAACTATATCCGAT-(EcoRV)-pBR328.
```

Fig. 10b pT7H6 Trip-A-Fn-Apo A1 - Amp^R.

pBR328-(PvuII)-GATCTCGATCCCGCGAAATTAATACGATACACTATAGGGAGACCACAACGTTTCCCTCTAGAAATAATTTTGTTTAACTTTAAGAAGGAGAT
                                        T7 promoter
ATACATATGGATCGCATCACCATCACCATCACGGTAGTGGTAGTGATCAATCCAGGTAGATCTCCTGAGCCACCAGAAGCCCAAGAAGATTGTAAATGCC
         M  G  S  H  H  H  H  H  H  G  S  G  S  I  Q  G  R  S  P  G  T  E  P  P  T  Q  K  P  K  K  I  V  N  A
                                                                              Bgl II            Kpn I
KKDVVNTKMFEELKSRLDTLAQEVALLKEQQALQTVSL
aAGAAAGATGTTGTAACACAAAAGATGTTTGAGGAGCTCAAGAGCCGTCTGGACACCCTGGCCCAGGAGGTGGCCCTGCTCAAGGAGCAGCAGGCCCTGCAGACGGTCTCCCTG
BamHI
AAGGGATCCtcgggtcatgatgaacccccccagagcccctgggatcgagtgaaggaccctggccactgtgtggatgtgctcaaagacagcggcagagac
 K  G  S  s  g  h  D  E  P  P  Q  S  P  W  D  R  V  K  D  L  A  T  V  V  D  V  L  K  D  S  G  R  D
tatgtgtcccagtttgaaggctccgcttggaaaacagctaaagctcctgacaactgggacagcgtgacctccaccttcagcaagctg
 Y  V  S  Q  F  E  G  S  A  L  G  K  Q  L  N  L  K  L  L  D  N  W  D  S  V  T  S  T  F  S  K  L
cgcgaacagctcggcccctgtgaccaggagttctggacaatctgggaaaaggagacagagggctgaggcaggagatgagcaaggatctggaggag
 R  E  Q  L  G  P  V  T  Q  E  F  W  D  N  L  E  K  E  T  E  G  L  R  Q  E  M  S  K  D  L  E  E
gtgaaggccaaggtgcagcccctacctgacgactctccagaagaagtggcaggaggatggagctctaccgccagaaggtggagccgctgcgcgca
 V  K  A  K  V  Q  P  Y  L  D  D  F  Q  K  K  W  Q  E  E  M  E  L  Y  R  Q  K  V  E  P  L  R  A
gagctccaagagggcgcgcggtcaagagcgcacgcgccagaagctgcacgaggagaagctgagccccactgggcgaggaagatgcgcgaccgcgcgccatgtg
 E  L  Q  E  G  A  R  Q  K  L  H  E  L  Q  E  K  L  S  P  L  G  E  E  M  R  D  R  A  R  A  H  V
gacgcgctgcgcacgcatctggcccccatcctacagccgagctgcgccagcgctgcgcagaggctgccagcccgcgaggagaacggcggcgccaga
 D  A  L  R  T  H  L  A  P  Y  S  D  E  L  R  Q  R  L  A  A  R  L  E  A  L  K  E  N  G  G  A  R
ctggccgagtacgccaaggccaccgagcacctgagcacgcatctgagcgagctcagcgagcacgctcagcgagaagccccggcgctcgaggacctcgctgccc
 L  A  E  Y  H  A  K  A  T  E  H  L  S  T  L  S  E  K  A  K  P  A  L  E  D  L  R  Q  G  L  L  P
gtgctgagagcttcaaggtcagcttcctcgagcgctctcgagggtacaaccccagTAATAAGCTTGAATTCGATCCGGCTGCTAA
 V  L  E  S  F  K  V  S  F  L  S  A  L  E  E  Y  T  K  K  L  N  T  Q  STOP HindIII EcoRI
CAAAGCCCGAAAGGAAGCTGAGTTGGCTGCTGCCGCCACCGTGAGCTGAGCAATAACTAGCATAACCCCTCTGCCACCGTGTGGGCCTCTAAACGGGTCTTGAGGGC
TTTTTGCTGAAAGGAGGAACTATATCCGAT-(EcoRV)-pBR328.

Fig. 10c pT7H6 Trip-A-Fn-Apo A1-final - Amp^R.

```
pBR328-(PvuII)-GATCTCGATCCGCGAAATTAATACGATACACTATAGGGAGACCACAACGGTTTCCCTCTAGAAATAATTTTGTTTAACTTTAAGAAGGAGAT
                                    T7 promoter
                   M  G  S  H  H  H  H  H  H  G  S  G  S  I  Q  G  R  S  P  G  T  E  P  P  T  Q  K  P  K  I  V  N  A
ATACATATGGGATCGCATCACCATCACCATCACGGTAGTGGTAGTGGATCAATCAGGGTAGATCTCCTGGTACCGAGCCCAACCCAGAAGCCCAAGAAGATTGTAAATGCC
                                              Bgl II   Kpn I
  K  K  D  V  V  N  T  K  M  F  E  E  L  K  S  R  L  D  T  L  A  Q  E  V  A  L  L  K  E  Q  Q  A  L  Q  T  V  S  L
AAGAAAGATGTTGTGAACACAAAGATGTTTGAGGAGCTTAAGAGCCGTCTTGAGACACCTGGCCCAGGAGGTGGCCCTGCTGAAGGAGCAGCAGGCCCTGCAGACGGTCTCCCTG
 Bam HI
AAGGGAACCtcggtcaggatgaacccccccagagccctgggatcgagtggaccgtgtaaactaagctcctgacaactgggacagcgtgacctccaccttcagcaagctg
  K  G  T  s  g  g  D  E  P  P  P  Q  S  P  W  D  R  V  K  D  L  A  T  V  Y  V  D  V  L  K  D  S  G  R  D
tatgtgtcccagttcgaaggctccgcttggaaaacagctaaagctcctggacaactgggacagcgtgacctccaccttcagcaagctg
  Y  V  S  Q  F  E  G  S  A  L  G  K  Q  L  N  L  K  L  L  D  N  W  D  S  V  T  S  T  F  S  K  L
cgcgaacagctcggcccctgtgacccaggagttctgaccagaggcctggaacagcagaggatgagcaagatctggaggag
  R  E  Q  L  G  P  V  T  Q  E  F  W  D  N  L  E  K  E  T  E  G  L  R  Q  E  M  S  K  D  L  E  E
gtgaaggccaaggtgcagcccctacctggacgactctaccgccagaaggtggagctcctgctgcgcca
  V  K  A  K  V  Q  P  Y  L  D  D  F  Q  K  K  W  Q  E  E  M  E  L  Y  R  Q  K  V  E  P  L  R  A
gagctccaagagagggcgcgcagaagctgagccacctgggcgaggagatgcgagaccgcgcgcgcccatgtg
  E  L  Q  E  G  A  R  Q  K  L  H  E  L  Q  E  K  L  S  P  L  G  E  E  M  R  D  R  A  R  A  H  V
gacgcgctgcgcacgcatctggccccctacagcgacgagctgcgccagcgcttggccgcagcgccttgaggctctcaaggagaacggcggccaga
  D  A  L  R  T  H  L  A  P  Y  S  D  E  L  R  Q  R  L  A  A  R  L  E  A  L  K  E  N  G  G  A  R
ctggccgagtaccacgccaaggccatgcggacacgtcgagcacgtcagcgagaaggccaagcccgccctcgaggaccctccgccaaggcctgccc
  L  A  E  Y  H  A  K  A  T  E  H  L  S  T  L  S  E  K  A  K  P  A  L  E  D  L  R  Q  G  L  L  P
gtgctggagagcttcaaggtgcagctcagctcgagcgtctcgaggagtacactaagaagctcaacacccagTAATAAGCTTGAATTCCGATCCGGCTGCTAA
  V  L  E  S  F  K  V  S  F  L  S  A  L  E  E  Y  T  K  K  L  N  T  Q STOP HindIII EcoRI
CAAAGCCCGAAAGGAAGCTGAGTTGGCTGCCTGCCACCGGTTGGCTGAGCTGAGCAATAACTAGCATAACCCCTGCCACCGCTGTGGGGCCTCTAAACGGGTCTTGAGGGG
TTTTTGCTCAAGGAGGAACTATATCCGAT-(EcoRV)-pBR328.
```

Fig. 10d pT7H6 Trip-A-Fn-Apo A1 final K9AK15A - Amp^R.

```
pBR328-(PvuII)-GATCTCGATCCCGCGAAATTAATACGATACACTATAGGGAGACCACAACGGTTTCCCTCTAGAAATAATTTTGTTTAACTTTAAGAAGGAGAT
                                        T7 promoter
               M  G  S  H  H  H  H  H  H  G  S  G  S  I  Q  G  R  S  P  G  T  E  P  P  T  Q  K  P  K  A  I  V  N  A
ATACATATGGGATCGCATCACCATCACCATCACGGTAGTGGTAGTGGTAGTGATCAATCCAGGTAGATCTCCTGGTACCGACCCACCACCCAGAAGCCCAAGGCGATTGTAAATGCC
                                                                   BglII  KpnI
   K  A  D  V  V  N  T  K  M  F  E  E  L  K  S  R  L  D  T  L  A  Q  E  V  A  L  L  K  E  Q  Q  A  L  Q  T  V  S  L
AAGGCAGATGTTGTGAACACAAAGATGTTTGAAGAGCTCAAGAGCCGTCTGGACACCCTGGCCCAGGAGGTGGCCCTGCTGAAGGAGCAGCAGGCCCTGCAGACGGTCTCCCTG
    BamHI
AAGGGAACCtcgggtcaggatgaccccccagagccccttgggatcgagtgaaggaccctgccactgtgtacgtggatgtgctcaaagacagcggcagagac
   K  G  T  s  g  q  D  E  P  P  Q  S  P  W  D  R  V  K  D  L  A  T  V  Y  V  V  D  V  L  K  D  S  G  R  D
tatgtgtcccagtttgaaggctccgctttgggaaacagctaaactgaaactgaagctcgttgacaacagcgtgacctccaccttcagcaagctg
   Y  V  S  Q  F  E  G  S  A  L  G  K  Q  L  N  L  K  L  L  D  N  W  D  S  V  T  S  T  F  S  K  L
cgcgaacagctcggccctgtgaccaggagttctgggataacctgagtgggatataaccgtgaaaagagacagagggcctgaggcaggagcaagatgagctggaggag
   R  E  Q  L  G  P  V  T  Q  E  F  W  D  N  L  E  K  E  T  E  G  L  R  Q  E  M  S  K  D  L  E  E
gtgaaggccaaggtgcagcctacctggacgacttccagaagaagtggcaggaggatggagctctaccgccagaaggtggagccgctgcgggcca
   V  K  A  K  V  Q  P  Y  L  D  D  F  Q  K  K  W  Q  E  E  M  E  L  Y  R  Q  K  V  E  P  L  R  A
gagctccaagagaggcgcgcgcagcgcatcgaccccctacaccgagcgacgagctgcgcgccagcgcttggccgcgcctttggctctcaaggagaacggcggcgccaga
   E  L  Q  E  G  A  R  Q  K  L  H  E  L  Q  E  K  L  S  P  L  G  E  E  M  R  D  R  A  R  A  H  V
acggcctgccgcacgcatctgccccccctgaagccccaccgatctgagcagcatctgagcgcctcagcgagaaggccaagcccgcgctcgagaccctccgcgcctgccc
   D  A  L  R  T  H  L  A  P  Y  S  D  E  L  R  Q  R  L  A  A  R  L  E  A  L  K  E  N  G  G  A  R
ctggccgagtaccacgccaaggccacaggagcatctgagcgcgtcctgagggctaacactaagaagctcaacacccagTAATAAGCTTGAATTCCGATCCGGCTGCTAA
   L  A  E  Y  H  A  K  A  T  E  H  L  S  T  L  S  E  K  A  K  P  A  L  E  D  L  R  Q  G  L  L  P
gtgctggagagcttcaaggtcagttctgagctctctgaggagtacactaagaagctcaacacccagTAATAAGCTTGAATTCCGATCCGGCTGCTAA
   V  L  E  S  F  K  V  S  F  L  S  A  L  E  E  Y  T  K  K  L  N  T  Q  STOP HindIII EcoRI
CAAAGCCCGAAAGGAAGCTGAGCTGGCTGCCACCGCTGAGCTGAGCAATAACTAGCAATAACCCCTCTGCCACCGCTGTGGGGCCTCTAAACGGTCTTGAGGGG
TTTTTGCTGAAAGGAGGAACTATATCCGAT-(EcoRV)-pBR328.
```

Fig. 10e pT7H6 (GS)3 Trip-A-Tn-Apo A1 Amp^R.

Fig. 10f pT7H6 Trip-A-Tn-Apo A1-final - Amp^R.

```
pBR328-(PvuII)-GATCTCGATCCGGAAATTAATACGATACACTATAGGGAGACCACAACGGTTTCCCTCTAGAAATAATTTTGTTTAACTTTAAGAAGGAGAT
                                  T7 promoter
                    M  G  S  H  H  H  H  H  H  G  S  G  S  I  Q  G  R  S  P  G  T  E  P  P  T  Q  K  P  K  K  I  V  N  A
ATACATATGGGATCGCATCACCATCACCATCACGGTAGTGGTAGTGGATCAATCCAGGTAGATCTCCTGGTACCGAGCCACCAACCCAGAAGCCCAAGAAGATTGTAAATGCC
                                                            Bgl II   Kpn I
K  K  D  V  V  N  T  K  M  F  E  E  L  K  S  R  L  D  T  L  A  Q  E  V  A  L  L  K  E  Q  Q  A  L  Q  T  V  S  L
aAGAAAGATGTTGTGAACACAAAGATGTTTGAAGAGCTCAAGAGCCGTCTCGACACCCTGGCCCAGGAGGTGGCCCTGCTGAAGGAGCAGCAGGCCCTGCAGACGGTCTCCCTG
                                                Bam HI
AAGGGAACCAAGGTGCACATGAAGgaacccccccagagcccctgggaaggaccctgagtgaaggacctaaactcctgacaactgggacagcgtgacctccaccttcagcaagctg
K  G  T  K  V  H  M  K  D  E  P  P  Q  S  P  W  D  R  V  K  D  L  A  T  V  V  V  D  V  L  K  D  S  G
agagactatgtgtcccagtttgaaggctccgctggagtgctgaccgagttctgtgaccCaggagttctgacccaggagttctgggataaacctggaaaaggagacagagggctcgaggcctgaggcaggagcaagatctggaggag
R  D  Y  V  S  Q  F  E  G  S  A  L  G  K  Q  L  N  L  K  L  L  D  N  W  D  S  V  T  S  T  F  S  K  L
cgcgaacagctcggcctgacccaggagttctgggatacccaggagttctgggataaacctggaaaaggagacagagggctcgaggcctgaggcaggagcaagatctggaggag
R  E  Q  L  G  P  V  T  Q  E  F  W  D  N  L  E  K  E  T  E  G  L  R  Q  E  M  S  K  D  L  E  E
gtgaaggccaaggtgcagcccaggtacctggacgacttccagaagaagtggcaggaggatgggagctctaccgccagcaaggtggagccgctgcgcgca
V  K  A  K  V  Q  P  Y  L  D  D  F  Q  K  K  W  Q  E  E  M  E  L  Y  R  Q  K  V  E  P  L  R  A
gagctccaagagggcgcgcgacgcacacgactctgcccctacaggcggacggctgcccctaggcggcgccctcgcccgctccgagcctgctgccc
E  L  Q  E  G  A  R  Q  K  L  H  E  L  Q  E  K  L  S  P  L  G  E  E  M  R  D  R  A  R  A  H  V
gacgcgctgcgcacgcacgcatctgccccctacagcccctacagctcgcgcagccgtcgcagccgtgccctgaggctcctcaaggagaacggcggccaga
D  A  L  R  T  H  L  A  P  Y  S  D  E  L  R  Q  R  L  A  A  R  L  E  A  L  K  E  N  G  G  A  R
ctggccgagtaccgcaccgccaaggccatctgagcgcttcctgagcgtctccgagaagcctcagccgaggccacgcctcgagctccaaggcctgctgccc
L  A  E  Y  H  A  K  A  T  E  H  L  S  T  L  S  E  K  A  K  P  A  L  E  D  L  R  Q  G  L  L  P
gtgctggagagcttcaaggttcagctcgagtcgtgcctgccaccgctgagctgagcaataactagctacatacccctctgccaccgtgctctaaacggggtcttgagggg
V  L  E  S  F  K  V  S  F  L  S  A  L  E  E  Y  T  K  K  L  N  T  Q  STOP  HindIII  EcoRI
CAAAGCCCGAAAGGAAGCTGAGTTGGCTGCCTGCCACCGCTGAGCTGAGCAATAACTAGCTACATAACCCCTCTGCCACCGTGTGGGGCCTCTAAACGGGTCTTGAGGGG
TTTTTGCTGAAGAAGGAGGAACTATATCCGAT-(EcoRV)-pBR328.
```

Fig. 10g pT7H6 Trip-A-Tn-Apo A1 final K9AK15A- Amp^R.

```
pBR328-(PvuII)-GATCTCGATCCCGCGAAATTAATACGATACACTATAGGGAGACCACAACGTTTCCCTCTAGAAATAATTTGTTTAACTTTAAGAAGGAGAT
                                        T7 promoter
             M  G  S  H  H  H  H  H  H  G  S  G  S  G  S  I  Q  G  R  S  P  G  T  E  P  P  T  Q  K  P  K  A  I  V  N  A
ATACATATGGGATCGCATCACCATCACCATCACGGTAGTGGTAGTGGATCAATCCAGGGTAGATCTCCTGGTACCGAGCCACCAAGGACCCCAAGGCGATTGTAAATGCC
                                                        BglII   KpnI
  K  A  D  V  V  N  T  K  M  F  E  E  L  K  S  R  L  D  T  L  A  Q  E  V  A  L  L  K  E  Q  Q  A  L  Q  T  V  S  L
AAGGCAGATGTTGTGAACACAAAGATGTTTGAAGAGCTCAAGAGCCGTCTGGACACCCTGGCCCAGGAGGTGGCCCTGCTGAAGGAGCAGCAGGCCCTGCAGACGGTCTCCCTG
         BamHI
  K  G  T  K  V  H  M  K  D  E  P  P  Q  S  P  W  D  R  V  K  D  L  A  T  V  Y  V  D  V  L  K  D  S  G
AAGGGAACCAAGGTGCACATGAAGgaaccccccagagcccctgggatcgagtgaaggacctggccactgtgtacgtggatgtgctcaaagacagcggc
agagactatgtgtcccagtttgaaggctccgctttggagctccgctcagtttgaaggctccgctgcgcttgacaactgggacagcgtgacctccaccttcagcaagctg
 R  D  Y  V  S  Q  F  E  G  S  A  L  G  K  Q  L  N  L  K  L  L  D  N  W  D  S  V  T  S  T  F  S  K  L
cgcgaacagctctcggcctgtgaccagcggatttctgggaagttctggggaatctggaaaaggagacagaggcctgagggccaggagatgagcaaggatctggaggag
 R  E  Q  L  G  P  V  T  Q  E  F  W  D  N  L  E  K  E  T  E  G  L  R  Q  E  M  S  K  D  L  E  E
gtgaaggcaagtgtgcagccgcctacctggacgacttccagaagaagtgcaagagagctgcaagagatgcacactggagatgtgagctgatgtgagcgtgctgcgcgca
 V  K  A  K  V  Q  P  Y  L  D  D  F  Q  K  K  W  Q  E  E  M  E  L  Y  R  Q  K  V  E  P  L  R  A
gagctccaagagggcgcgcagaagcatctgcaccaagtgcaagctccctgccctgggcgagctggtgagatgagatgctggatgtgcgcgcgccatgtg
 E  L  Q  E  G  A  R  Q  K  L  H  E  L  Q  E  K  L  S  P  L  G  E  E  M  R  D  R  A  R  A  H  V
gacgcgctgcgcacatctgagcgacgccctacagcagtgctgcgcagcgctgctgtgcgcagcgctgctgcgcgcgcagcggatgctctcaaggagaacggcggccaga
 D  A  L  R  T  H  L  A  P  Y  S  D  E  L  R  Q  R  L  A  A  R  L  E  A  L  K  E  N  G  G  A  R
ctggccgagtacacagccaaggccacggccagcatctggcgcgagaccatgtgaggatgtgaagactgagagactgcaagaactccagcctgaaagcggctcgtgcgtgccc
 L  A  E  Y  H  A  K  A  T  E  H  L  S  T  L  S  E  K  A  K  P  A  L  E  D  L  R  Q  G  L  L  P
gtgctggagagcttcaaggtcagtttcctgagcgctctcgaggagtacactaagaagctcaacaccaccagTAATAAGCTTGAATTCGATCCGGCTGCTAA
 V  L  E  S  F  K  V  S  F  L  S  A  L  E  E  Y  T  K  K  L  N  T  Q  STOP  HindIII  EcoRI
CAAAGCCCGAAAAGGAAGAGCTGAGTTGGCTGCCTGCCACCGCTGAGCTGAGCAATAACTAGCATAACCCCCTCGCTGTGGGGGCCTCTAAACGGGTCTTGAGGGG
TTTTTTTGCTGAAGGAGGAACTATATCCGAT-(EcoRV)-pBR328.
```

Fig. 10h pT7H6 Hp-alpha-Apo A1 - Amp^R pBR328-(PvuII)-GATCTCGATCCCGCGAAATTAATACGATACACTATAGGGAGACCACAACGGTTCCCTCTAGAAATAATTTGTTTAACTTTAAGAAGGAGAT
                                        T7 promoter
ATACATATGGGATCGCATCACCATCACCATCACGGATCGATCCAGGGTAGAGGTgtgactcaggcaatgatgtcacggatatcgcagatgacggtgcccgaagcccccgag
         M  G  S  H  H  H  H  H  H  G  S  I  Q  G  R  G  V  D  S  G  N  D  V  T  D  I  A  D  D  G  C  P  K  P  P  E
atgcacatggctatgtggagcactcggttcgctaccagtgtaagaactactacaaactgcgcacagagagatggagtatacacctaaacaatgagaagcag
 I  A  H  G  Y  V  E  H  S  V  R  Y  Q  C  K  N  Y  Y  K  L  R  T  E  G  D  G  V  Y  T  L  N  N  E  K  Q
tggataaataaggctgttggagataaacttcctgaatgtgaagcagtagcgtggaagcccaaacccagtgcagAGATCC
 W  I  N  K  A  V  G  D  K  L  P  E  C  E  A  V  A  G  K  P  K  N  P  A  N  P  V  Q  R  S
gatgaaccccccagagcccctggatcgagtgaaggaccctggagtgtacgtggatgtgctcaaagacagcggcagagac
 D  E  P  P  Q  S  P  W  D  R  V  K  D  L  A  T  V  Y  V  D  V  L  K  D  S  G  R  D
tatgtgtccagtttgaaggctccgcttgggaaaacagctaaactccttgacaactgggacagcgtgacctccacctttcagcaagctg
 Y  V  S  Q  F  E  G  S  A  L  G  K  Q  L  N  L  K  L  L  D  N  W  D  S  V  T  S  T  F  S  K  L
cgcgaacagctcggcctgtgaccaggagttctgaccagcctgaggcaggagatgagcaaggatctggaggag
 R  E  Q  L  G  P  V  T  Q  E  F  W  D  N  L  E  K  E  T  E  G  L  R  Q  E  M  S  K  D  L  E  E
gtgaaggccaaggtgcagccctacctggacgacttccagagagctgtgcaggagaagtggcaggaggtggagctgcgcgca
 V  K  A  K  V  Q  P  Y  L  D  D  F  Q  K  K  W  Q  E  E  M  E  L  Y  R  Q  K  V  E  P  L  R  A
gagctccaagagggcgcgcccagagcgcaactgcatgagctgcagcttgagcagaagctcagcccgctgggcgaggagatgcgcgaccgcgcgcgccatgtg
 E  L  Q  E  G  A  R  Q  K  L  H  E  L  Q  E  K  L  S  P  L  G  E  E  M  R  D  R  A  R  A  H  V
gacgcgctgcgcacgcatctggcccctacagcgacgagctgcgccagcgcttggccgcgcctgcgcagccgcctcgaggagaacggcgcgccaga
 D  A  L  R  T  H  L  A  P  Y  S  D  E  L  R  Q  R  L  A  A  R  L  E  A  L  K  E  N  G  G  A  R
ctggccgagtaccacgccaaggccaccgagcatctgagcacgctcagcgagaagcccgagaaggccaagcctgagaagcttgagaactcgaggacctgcgccaaggcctgctgccc
 L  A  E  Y  H  A  K  A  T  E  H  L  S  T  L  S  E  K  A  K  P  A  L  E  D  L  R  Q  G  L  L  P
gtgctggagagcttcaaggtcagcttcctgagcgctctcgaggagtacactaagaagctcaacaccccagTAATAAGCTTGAATTCCGATCCGGCTGCTAA
 V  L  E  S  F  K  V  S  F  L  S  A  L  E  E  Y  T  K  K  L  N  T  Q  STOP  HindIII EcoRI
CAAAGCCCGAAAGAAGCTGAGTTGGCTGCTGCCTGAGCTGAGCAATAACTAGCATAACCCCTCTGCCACCGCTGTGGGGCCTCTAAACGGGTCTTGAGGGG
TTTTTTGCTGAAGGAGGAACTATATCCGAT-(EcoRV)-pBR328.

APOLIPOPROTEIN ANALOGUES

This application claims the benefit of provisional application 60/264,022 filed on Jan. 26, 2001.

The invention relates to a pharmaceutical composition comprising an apolipoprotein construct, to an apolipoprotein construct, a nucleic acid sequence encoding the apolipoprotein construct, a vector comprising the nucleic acid sequence, a method for producing the apolipoprotein construct, and a method of treatment comprising administering the apolipoprotein construct.

PRIOR ART

In the following, the term Apo A or apolipoprotein A will be used to designate any of the three apolipoproteins, Apolipoprotein AI, Apolipoprotein AII, or Apolipoprotein AIV.

Cardiovascular diseases caused by atherosclerosis in the vessels is the most frequent cause of death in the industrialised countries of the World. One of the pathogenic factors causing atherosclerosis is the deposition of cholesterol in the vessel walls leading to plaque formation and eventually to arterosclerosis and increased risk of infarction.

Apolipoprotein A-1 (apo-A-1) is the main component of plasma HDL (high density lipoprotein), which is negatively correlated to the presence of arterosclerosis. There is strong experimental evidence that this effect is caused by so-called reverse cholesterol transport from peripheral tissues to the liver. There is also experimental evidence that this reverse cholesterol transport can be stimulated in mammals by injection of apo-A-1.

Apolipoprotein A-1 is rapidly cleared from plasma. It is believed that Apo-A-1 is to a large extent removed from plasma by filtration in the kidneys without being broken down first (Braschi et al 1999, J Lipid Res, 40:522–532; Braschi et al 2000, Biochemistry, 39:5441–5449; Glass et al 1983, J Biol Chem 258:7161–7167). The short plasma half-life of apolipoprotein A is a constraint against using the protein in the treatment of atherosclerosis.

U.S. Pat. No. 5,876,968 (SIRTORI ET AL.) concerns substantially pure dimers of a variant of apo-A-1 called apolipoprotein A-1-Milano. Medicaments containing the dimer can be used for preventing thrombosis or they can be used as a prodrug for the monomer.

A specific feature of this particular variant of apo-A-I is its ability to form covalent dimers with itself. The authors speculated that the presence of Apo A-I-M may be responsible for a prolonged plasma half-life, but no conclusive data have been presented.

U.S. Pat. No. 5,643,757 (SHA-IL ET AL.) discloses a method for the production of pure, stable, mature and biologically active human apolipoprotein A-I in high yield.

U.S. Pat. No. 5,990,081 (AGELAND ET AL.) discloses a method for treatment of arterosclerosis or cardiovascular diseases by administering a therapeutically effective amount of apoliproprotein A or apolipoprotein E.

WO 96/37608 (RHONE-POULENC ROHRER ET AL.) describes human homologous dimers of apolipoprotein A-I variants comprising cystein in position 151. The presence of the cystein residue in the amino acid sequence allows the formation of dimers via disulphide bridges between the monomers. The reference furthermore discloses the corresponding nucleic acid sequences and vectors comprising these as well as pharmaceutical compositions comprising the variants and the use of these in gene therapy.

WO 90/12879 (Sirtori et al) and WO 94/13819 (Kabi Pharmacia) disclose methods for preparation of ApoA-I and ApoA-IM in yeast and E. coli respectively. The documents also disclose the use of ApoA-I and ApoA-IM as a medicament for the treatment of atherosclerosis and cardiovascular diseases.

In conclusion the prior art is mainly concerned with the use of native ApoA-I or ApoA-IM monomer or ApoA-IM dimer as medicaments for the treatment of vascular diseases, despite the known disadvantages of these proteins (mainly rapid clearance). The prior art does not suggest to modify ApoA-I in order to obtain constructs with increased ability to perform reverse cholesterol transport and/or with longer plasma half life. It is thus one object of the present invention to provide such ApoA constructs, which may be used for treatment and/or prevention of cardiovascular diseases.

SUMMARY

In a first aspect the invention relates to a pharmaceutical composition comprising an apolipoprotein construct having the general formula apo A-X, where apo A is an apolipoprotein A component selected from the group consisting of apolipoprotein AI, apolipoprotein AII, apolipoprotein AIV, an analogue or a variant thereof, and X is a heterologous moiety comprising at least one compound selected from the group consisting of an amino acid, a peptide, a protein, a carbohydrate, and a nucleic acid sequence, with the proviso that when the construct consists of exactly two identical, native apolipoproteins these are linked serially.

By the invention is provided a novel pharmaceutical composition. The prior art fails to teach an apoliprotein construct as defined in the present invention for inclusion in a pharmaceutical composition. The apolipoprotein constructs according to the present invention may broadly be looked upon as HDL analogues due to their ability to form complexes with cholesterol and other lipids and assist in the transportation of these compounds to the liver.

Throughout the invention the apolipoprotein component or part of the construct is referred to as apo A or apolipoprotein. In the following and in the claims, the heterologous moiety is referred to as component X of the construct. The apolipoprotein or analogue or variant thereof is linked covalently to the heterologous moiety.

The component X of the construct may be looked broadly upon as a heterologous moiety. In this context a heterologous moiety is any kind of moiety not being linked to apolipoprotein or analogue or variant or functional equivalent thereof under native conditions. The heterologous moiety may thus be a peptide or a protein or part of a peptide or protein from the same or from another species, or even a single amino acid. It may be a synthetic peptide. It may be of carbohydrate nature or of other polymeric and biocompatible nature such as polyols, nucleic acids sequences.

Functional equivalence to native apolipoprotein A-I, A-II or A-IV may conveniently be measured using a lipid binding assay. The ability of the construct to elicit substantially the same physiological response in a mammal may conveniently be measured by measurement of the ability to perform reverse cholesterol transport in a test organism such as rabbits or rodent such as mice.

The construct comprising apolipoprotein and a heterologous moiety is capable of performing reverse cholesterol transport as well as or even better than native apolipoproteins, despite the modification caused by the addition of a heterologous moiety. The plasma half-life of the construct is preferably increased compared to that of the wild-type apolipoprotein. The increased half-life can be due either to the increased size of the apolipoprotein construct, which may reduce the rate of filtration through the kidneys, it may be due to increased binding to HDL, or it may be due to reduced breakdown of the construct compared to native Apo A.

Preferably the plasma half-life is at least doubled or tripled, or at least quadrupled, or at least 10 doubled. Similarly, the binding affinity such as the lipid binding affinity, and/or the cholesterol binding affinity of the construct is preferably increased as compared to wild-type apolipoprotein. Preferably, the lipid binding affinity is increased by at least 5%, such as at least 10%, for example at least 15%, such as at least 20%, for example at least 25%, such as at least 30%, for example at least 40% such as at least 50%, for example at least 75%, such as at least 100%, such as at least 150%, for example at least 200%, such as at least 300%. Even in the cases where the lipid binding affinity of the constructs according to the invention is the same or lower than the lipid binding affinity of native apolipoprotein, the clinical effect may be enhanced due to increased plasma half life of the constructs according to the invention.

An increased plasma half-time and/or increased lipid binding affinity have profound implications for the use of the apolipoprotein constructs in the treatment of arterosclerosis. It is therefore expected that the clinical effect of the apolipoprotein constructs according to the invention is superior to the effect of wild-type apolipoproteins.

The invention also encompasses analogues or variants of the wild-type apoliproteins capable of eliciting substantially the same physiological response in a mammal.

The pharmaceutical composition may further comprise pharmaceutical acceptable excipients, adjuvants, additives, such as lipids, phospholipids, cholesterol, or triglycerides.

According to a second aspect of the invention, there is provided an apolipoprotein construct having the general formula
  apo A-X,
  where apo A is an apolipoprotein component selected from the group consisting of apolipoprotein AI, apolipoprotein AII, apolipoprotein AIV, an analogue or a variant thereof,
  and X is a heterologous moiety selected from the group consisting of an oligomerising module, and a terminally linked apolipoprotein.

According to a further aspect, there is provided a nucleotide sequence encoding an apolipoprotein construct as defined above. Preferably the nucleotide sequence is operably linked to a regulatory sequence for expression of the protein construct.

According to further aspects of the invention, there is provided a vector comprising the nucleotide sequence encoding the apolipoprotein construct and a transformed host cell comprising the nucleotide sequence as defined above.

The apolipoprotein construct according to the invention may be produced by different methods.

According to a first method a transformed host cell is cultured under conditions promoting the expression of a protein construct according to the invention encoded by DNA inserted into a construct, obtaining and recovering the protein construct and optionally further processing the protein construct.

This method is the preferred method when the whole construct is of polypeptide nature and thus can be encoded by one corresponding nucleic acid sequence.

According to a second method the apolipoprotein construct can be manufactured by chemically synthesising the heterologous moiety and subsequently linking it to the apolipoprotein or analogue obtaining an apolipoprotein construct, which is isolated and optionally processed further. This method is the preferred method, when the heterologous moiety is of non-peptide nature. However there may also be conditions under which it is preferred to synthesise the heterologous moiety chemically, when it is of polypeptide nature. Such conditions may be that the heterologous moiety is rather short such as below 20 amino acids.

According to a third method the apolipoprotein construct can be manufactured by culturing a transformed host cell under conditions promoting the expression of an apolipoprotein or an apolipoprotein analogue encoded by a nucleic acid fragment and subsequently covalently linking the apolipoprotein or apolipoprotein analogue to a heterologous moiety obtaining an apolipoprotein construct, isolating the resulting apolipoprotein construct and optionally further processing the construct.

Finally, the apolipoprotein construct may be produced by culturing a transformed host cell under conditions promoting the expression of a protein encoded by a nucleic acid fragment encoding an oligomerising module and subsequently linking said module to at least one apolipoprotein obtaining an apolipoprotein construct.

According to a further aspect of the invention there is provided a method for treating a patient having a condition related to cholesterol, phospholipids and triacylglycerides LDL and HDL disorders, and arteriosclerotic diseases comprising administering to the individual a pharmaceutical composition according to the invention.

The pharmaceutical composition may be administered intravenously, intraarterially, intramusculary, transdermally, pulmonary, subcutaneously, intradermally, intratechally, through the buccal-, anal-, vaginal-, conjunctival-, or intranasal tissue, or by inoculation into tissue, such as tumour tissue, or by an implant, or orally.

The apolipoprotein construct as defined above may also be used for gene therapy, wherein the DNA sequence encoding the apolipoprotein construct is used for transfection or infection of at least one cell population.

DETAILED DESCRIPTION OF THE INVENTION

In the following the invention will be described in detail with reference to the following figures.

FIG. 1 shows the amino acid sequence (SEQ ID NO:15) (in one letter code) of human apolipoprotein A-I.

FIG. 2A shows CLUSTAL W (1.74) multiple sequence alignment of apolipoprotein A-I using BLOSUM. The following sequences are aligned in the Figure:

Figure 11:
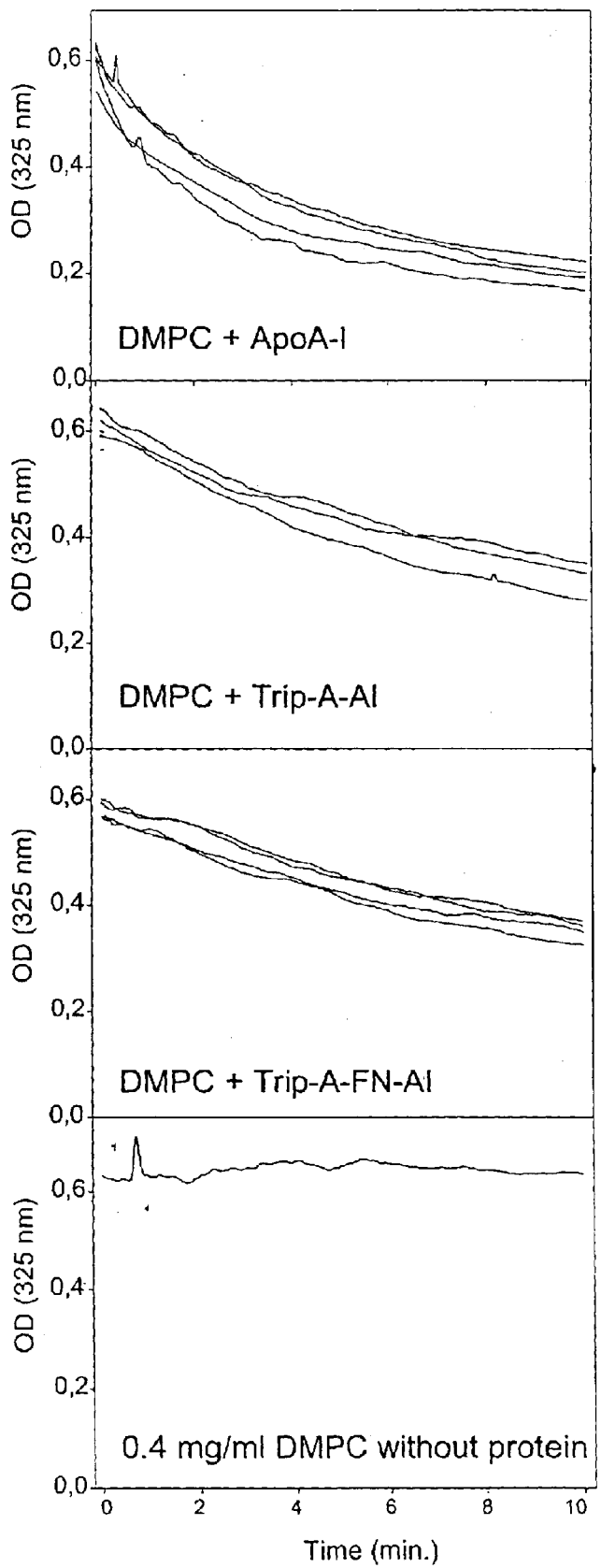

HUMAN sp|P02647|APA1_HUMAN Apolipoprotein A-I precursor (Apo-AI)—Homo sapiens (Human) (SEQ ID NO:15). Macaque sp|P15568|APA1_MACFA Apolipoprotein A-I precursor (Apo-AI)—Macaca fascicularis (Crab eating macaque) (SEQ ID NO:16).

Bovine sp|P15497|APA1_BOVIN Apolipoprotein A-I precursor (Apo-AI)—Bos taurus (Bovine) (SEQ ID NO:17).

Pig sp|P18648|APA1_PIG Apolipoprotein A-I precursor (Apo-AI)—Sus scrofa (Pig) (SEQ ID NO:18).

Dog sp|P02648|APA1_CANFA Apolipoprotein A-I precursor (Apo-AI)—Canis fainiliaris (Dog) (SEQ ID NO:19).

Rabbit sp|P09809|APA1_RABIT Apolipoprotein A-I precursor (Apo-AI)—Oryctolagus cuniculus (Rabbit) (SEQ ID NO:20).

Tree shreew sp|O18759|APA1_TUPGB Apolipoprotein A-I precursor (Apo-AI)—Tupaia glis belangeri (Common tree shrew) (SEQ ID NO:21).

Mouse sp|Q00623|APA1_MOUSE Apolipoprotein A-I precursor (Apo-AI)—Mus musculus (Mouse) (SEQ ID NO:22).

Rat sp|P04639|APA1_RAT Apolipoprotein A-I precursor (Apo-AI)—Rattus norvegicus (Rat) (SEQ ID NO:23).

Eur. Hedgehog tr|Q9TS49 APOLIPOPROTEIN A-I, APOA-I=CHOLESTEROL TRANSPORTER—Erinaceus europaeus (Western European hedgehog) (SEQ ID NO:24).

Chicken sp|P08250|APA1_CHICK Apolipoprotein A-I precursor (Apo-AI)—Gallus gallus (Chicken) (SEQ ID NO:25).

Jap. quail sp|P32918|APA1_COTJA Apolipoprotein A-I precursor (Apo-AI)—Coturriix coturnix japonica (Japanese quail) (SEQ ID NO:26).

Domestic duck sp|O42296|APA1_ANAPL Apolipoprotein A-I precursor (Apo-AI)—Anas platyrhynchos (Domestic duck) (SEQ ID NO:27).

Rainbow trout sp|O57523|AP11_ONCMY Apolipoprotein A-I-1 precursor (APOA-I-1)—Oncorhynchus mykiss (Rainbow trout) (Salmo gairdneri) (SEQ ID NO:28).

Brown trout sp|Q91488|APA1_SALTR Apolipoprotein A-I precursor (Apo-AI)—Salmo trutta (Brown trout) (SEQ ID NO:29).

Atl. salmon sp|P27007|APA1_SALSA Apolipoprotein A-I precursor (Apo-AI)—Salmo salar (Atlantic salmon) (SEQ ID NO:30).

Zebrafish sp|O42363|APA1_BPARE Apolipoprotein A-I precursor (Apo-AI)—Brachydanio rerio (Zebrafish) (Zebra danio) (SEQ ID NO:31).

Sea bream sp|O42175|APA1_SPAAU Apolipoprotein A-I precursor (Apo-AI)—Sparus aurata (Gilthead sea bream) (SEQ ID NO:32).

FIG. 2B shows aligned amino acid sequences (in one letter code) for human (SEQ ID NO:33), macaque (SEQ ID NO:34), mouse (SEQ ID NO:35), baboon (SEQ ID NO:36), pig (SEQ ID NO:37), and rat (SEQ ID NO:38) apolipoprotein A-IV.

FIG. 3: Amino acid sequence of the amino terminal region of tetranectin (SEQ ID NO 12). Amino acid sequence (in one letter code) from EI to L51 of tetranectin. Exon 1 comprises residues EI to D16 and exon 2 residues V17 to V49, respectively. The alpha helix extends beyond L51 to K52 which is the C-terminal amino acid residue in the alpha helix.

FIG. 4 shows an alignment of the amino acid sequences of the trimerising structural element of the tetranectin protein family. Amino acid sequences (one letter code) corresponding to residue V17 to K52 comprising exon 2 and the first three residues of exon 3 of human tetranectin (SEQ ID NO:39); murine tetranectin (SEQ ID NO:40) (Sørensen et al., Gene, 152: 243–245, 1995); tetranectin homologous protein isolated from reefshark cartilage (SEQ ID NO:42) (Neame and Boynton, 1992, 1996); and tetranectin homologous protein isolated from bovine cartilage (SEQ ID NO:41) (Neame and Boynton, database accession number PATCHX:u22298) Residues at a and d positions in the heptad repeats are listed in boldface. The listed consensus sequence of the tetranectin protein family trimerising structural element comprise the residues present at a and d positions in the heptad repeats shown in the figure in addition to the other conserved residues of the region. "hy" denotes an aliphatic hydrophobic residue.

FIG. 5 shows the pT7 H6UbiFx Apo A-I plasmid (SEQ ID NO:43) and its corresponding amino acid sequence (SEQ ID NO:44). The expressed and processed polypeptide consists of amino acids no 25–267 from human Apo A-I (SEQ ID NO 1) and gly-gly linked N-terminally thereto.

FIG. 6 shows the pT7 H6UbiFx Cys-Apo A-I plasmid (SEQ ID NO:45) and its corresponding amino acid sequence (SEQ ID NO:46). The expressed and processed polypeptide consists of a N-terminal cystein residue and the amino acids no 25–267 from human Apo A-I (SEQ ID NO 2) and gly-gly linked N-terminally thereto.

FIG. 7 shows the pT7H6 Trip-A-Apo A-I—Amp$^R$ plasmid (SEQ ID NO:47) and its corresponding amino acid sequence (SEQ ID NO:48). The expressed and processed polypeptide (SEQ ID NO 3) consists of the tetranectin trimerising structural element (TTSE), a linking sequence, and amino acids no 25–267 from human Apo A-I.

FIG. 8 shows the pT7H6 Trip-A-Apo A-I-del 43—Amp$^R$ plasmid (SEQ ID NO:49) and its corresponding amino acid sequence (SEQ ID NO:50). The expressed and processed polypeptide (SEQ ID NO 4) consists of the TTSE, a linking sequence, and amino acids no 68–267 from human Apo A-I.

FIG. 9 shows the pT7H6FXCysApoAI plasmid (SEQ ID NO:51) and its corresponding amino acid sequence (SEQ ID NO:52). The expressed and processed polypeptide consists of a N-terminal cystein residue and the amino acids no 25–267 from human Apo A-I (SEQ ID NO 2) and gly-gly linked N-terminally thereto.

Figure 10E:
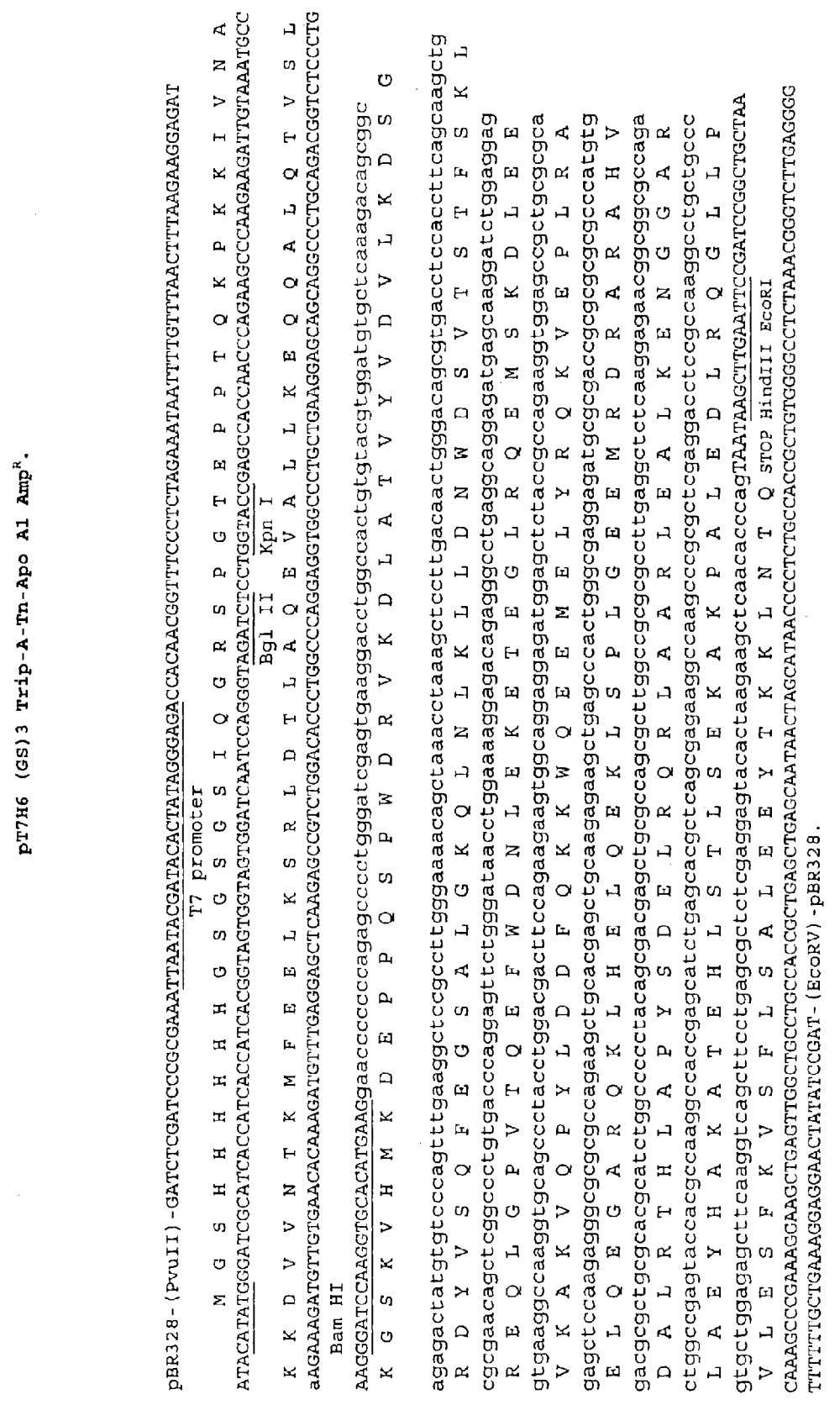

FIGS. 10A to G shows illustrative examples of lasmids (SEQ ID NOs:53, 55, 57, 59, 61, 63 and 65, respectiveiy) and corresponding amino acid sequences (SEQ ID NOs:54, 56, 58, 60, 62, 64 and 66, respectively) for apolipoprotein constructs according to the present invention.

FIG. 10A: pT7H6-Trip-A-Apo AI K9A K15A: Corresponds to pT7H6-Trip-A-Apo AI but two lysine residues in the trimerisation region has been mutated to remove the heparin affinity. The mature protein product is called Trip-A-AI K9A,K15A (SEQ ID NO 5).

FIG. 10B: pT7H6 Trip-A-FN-Apo AI: Corresponds to pT7H6-Trip-A-Apo AI, however, bases encoding the amino acid sequence SGH has been inserted after the Trip A sequence and before the apo AI sequence. The mature protein product is named Trip-A-FN-AI (SEQ ID NO 6).

FIG. 10C: pT7H6 Trip-A-FN-Apo AI-final: Corresponds to pT7H6 Trip-A-FN-Apo AI, however, the BamHI site of pT7H6 Trip-A-FN-Apo AI has been removed and the inserted three amino acid sequence changed, so that the amino acid sequence between the tetranectin derived trimerisation sequence and apo AI has been changed from GSSGH to GTSGQ. The five amino acid sequence corresponds to a sequence in the linker region of fibronectin. The mature protein product is named Trip-A-FN-AI-final (SEQ ID NO 7).

FIG. 10D: pT7H6 Trip-A-FN-Apo AI-final K9AK15A: Corresponds to pT7H6-Trip-A-FN-Apo AI-final but two lysine residues in the trimerisation region has been mutated to remove the heparin affinity. The mature protein product is called Trip-A-FN-AI-final-K9A,K15A (SEQ ID NO 8).

FIG. 10E: pT7H6 Trip-A-TN-Apo AI: Corresponds to pT7H6-Trip-A-Apo AI, however, bases encoding the amino acid sequence KVHMK has been inserted after the Trip A sequence and before the apo AI sequence. The mature protein product is named Trip-A-TN-AI (SEQ ID NO 9).

FIG. 10F: pT7H6 Trip-A-TN-Apo AI-final: Corresponds to pT7H6 Trip-A-TN-Apo AI, however, the BamHI site of pT7H6 Trip-A-TN-Apo AI has been removed so that the amino acid sequence between the tetranectin derived trimerisation sequence and apo AI has been changed from GSKVHMK to GTKVHMK. The seven amino acid sequence corresponds to the sequence of tetranectin following the trimerisation domain. The mature protein product is named Trip-A-TN-AI-final (SEQ ID NO 10).

FIG. 10G: pT7H6 Trip-A-TN-Apo AI-final K9AK15A: Corresponds to pT7H6-Trip-A-TN-Apo AI-final but two lysine residues in the trimerisation region has been mutated to remove the heparin affinity. The mature protein product is called Trip-A-TN-AI-final-K9A,K15A (SEQ ID NO 11).

FIG. 10H: pT7H6Fx-Hp(alpha)-ApoAI. The plasmid (SEQ ID NO:67) codes for the fusion protein (SEQ ID NO:68) between Hp(alpha) and ApoAi. The mature protein product is called Hp(alpha)-ApoAI (SEQ ID NO 14).

FIG. 11 shows the result of binding of ApoA-I, TripA-ApoA-I, and TripA-FN-ApoA-I to DMPC in the assay described in Example 6.

Figure 12:
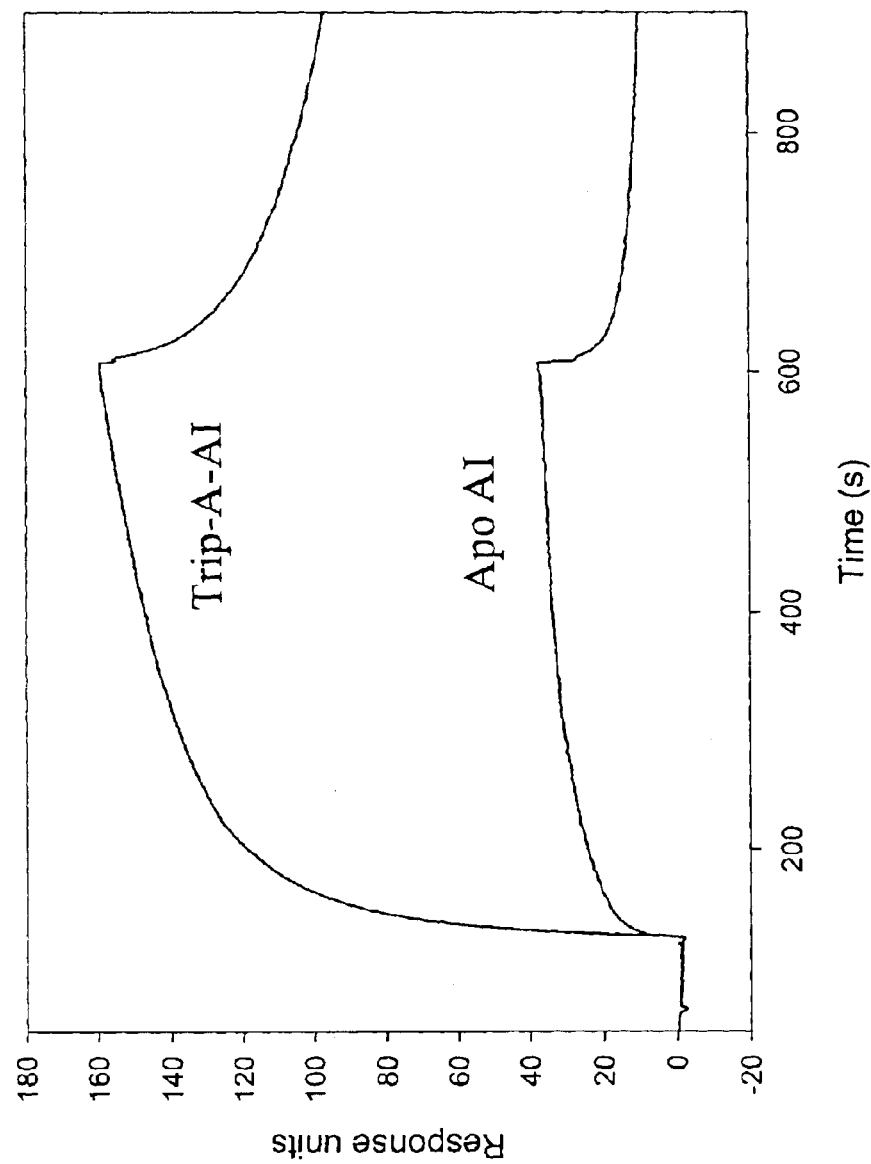

FIG. 12 shows binding of ApoA-I and TripA-ApoA-I to immobilised cubilin as described in Example 7.

Figure 13:
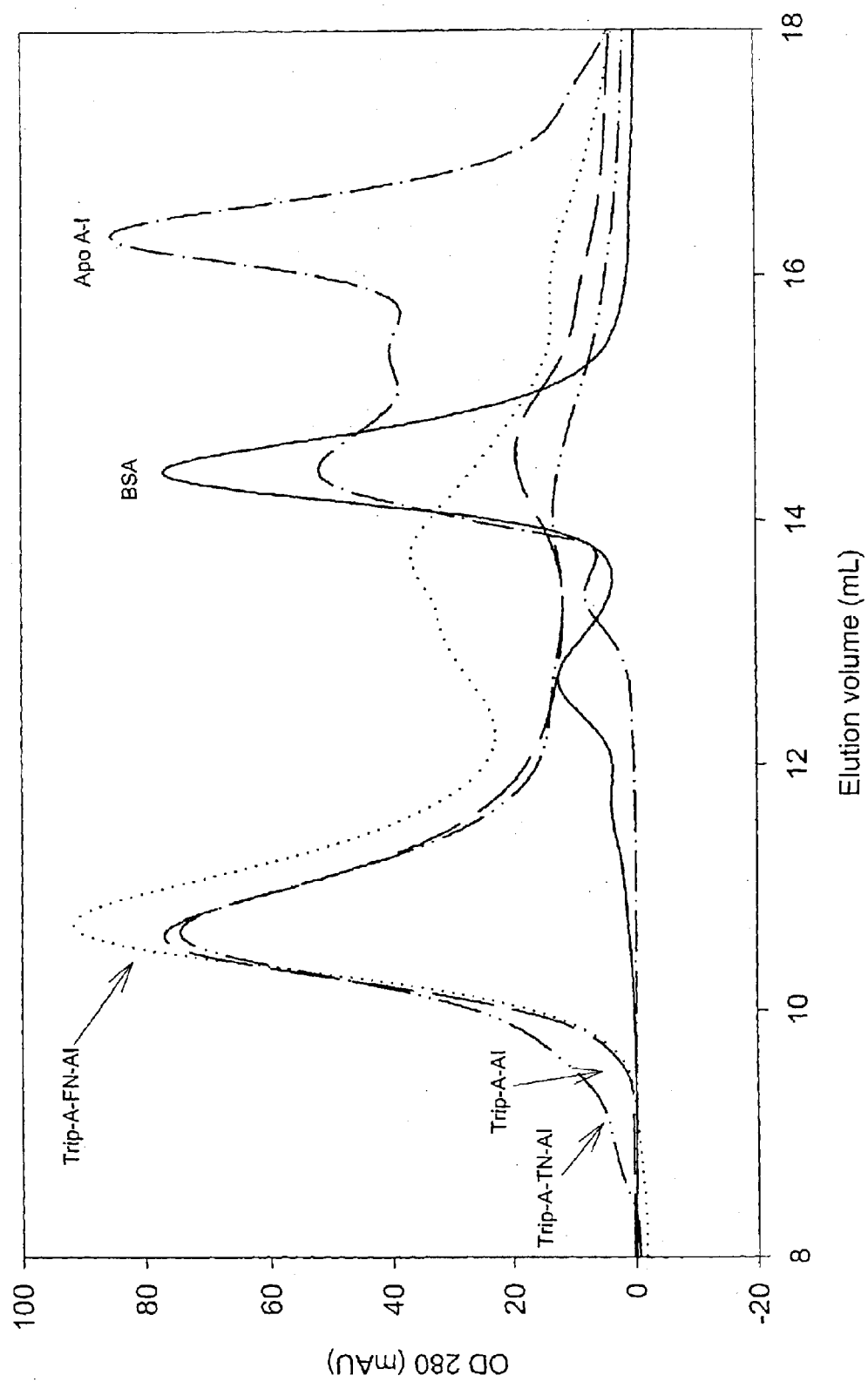

FIG. 13 shows analytical gelfiltration of Apo A-I, Trip-A-AI, Trip-A-TN-AI, Trip-A-FN-AI. As controls BSA was included. Details are disclosed in Example 5.

Figure 14:
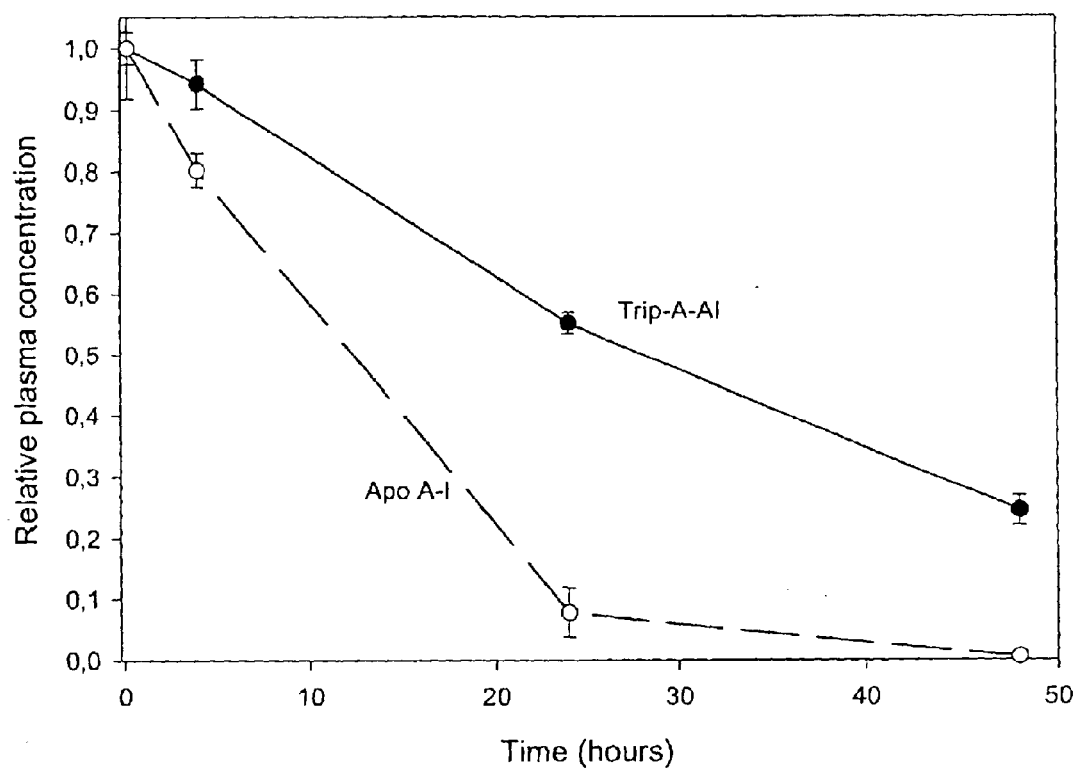

FIG. 14 shows the results of the evaluation of plasma clearance of apolipoprotein A-I, TripA Apo-AI, and TripA-fibronectin-linker Apo A-I in mice. Experimental details can be found in Example 8.

DETAILED DESCRIPTION OF THE INVENTION

The functionality of the constructs according to the invention and of the apo-A components of the constructs can be measured by a lipid binding assay such as by the DPMC assay described below. Furthermore, the in vivo effect on reverse cholesterol transport may be measured by administration to test animals such as rabbits fed on a cholesterol rich diet such as the method disclosed in Miyazaki et al (Arteriosclerosis, Thrombosis, and Vascular Biology, 1995; 15:1882–1888) or in Apo E deficient mice (Sha PK et al, Circulation 2001, 103:3047–3050).

The Apolipoprotein or Analogue

In the following the term "apo-A" is used to designate any apolipoprotein A comprising apolipoprotein A-I, apolipoprotein A-II or apolipoprotein A-IV, any variant or analogue thereof possessing the same lipid binding function.

Preferred apolipoprotein A-I analogues include those disclosed in FIG. 2A. Preferred apolipoprotein A-IV analogues include those disclosed in FIG. 2B.

Known variants of the sequences of human Apo-AI in FIG. 1 include the following variants, indicating the position of the variation with respect to the sequence in FIG. 1, the variation, and where appropriate the name of the known variant.

| 27 | P –> H (IN MUNSTER-3C). |
| 27 | P –> R. |
| 28 | P –> R (IN MUNSTER-3B). |
| 34 | R –> L (IN BALTIMORE). |

-continued

| 50 | G –> R (IN IOWA). |
| 84 | L –> R (IN AUTOSOMAL DOMINANT AMYLOIDOSIS). |
| 113 | D –> E. |
| 119 | A –> D (IN HITA). |
| 127 | D –> N (IN MUNSTER-3A). |
| 131 | MISSING (IN MARBURG/MUNSTER-2). |
| 131 | K –> M. |
| 132 | W –> R (IN TSUSHIMA). |
| 133 | E –> K (IN FUKUOKA). |
| 151 | R –> C (PARIS) |
| 160 | E –> K (IN NORWAY). |
| 163 | E –> G. |
| 167 | P –> R (IN GIESSEN). |
| 168 | L –> R (IN ZARAGOZA). |
| 171 | E –> V. |
| 189 | P –> R. |
| 197 | R –> C (IN MILANO). |
| 222 | E –> K (IN MUNSTER-4). |

According to the invention the term "apolipoprotein" is meant to include functional equivalents of at least one sequence in FIGS. 1, 2a and 2b, or a fragment of at least one sequence in FIGS. 1, 2a and 2b, comprising a predetermined amino acid sequence. A "fragment" is defined as:

i) fragments comprising an amino acid sequence capable of being recognised by an antibody also capable of recognising the predetermined amino acid sequences in FIG. 1, 2a or 2b, and/or ii) fragments comprising an amino acid sequence capable of binding to a lipid such as dimyristoyl phosphatidylcholine or cholesterol, and/or a receptor, which is also capable of binding the predetermined amino acid sequences in FIG. 1, 2a or 2b.

According to the present invention a functional equivalent of an apolipoprotein or fragments thereof may be obtained by addition, substitution or deletion of at least one amino acid. When the amino acid sequence comprises a substitution of one amino acid for another, such a substitution may be a conservative amino acid substitution. Fragments of the sequences in FIGS. 1, 2a and 2b may comprise more than one such substitution, such as e.g. two conservative amino acid substitutions, for example three or four conservative amino acid substitutions, such as five or six conservative amino acid substitutions, for example seven or eight conservative amino acid substitutions, such as from 10 to 15 conservative amino acid substitutions, for example from 15 to 25 conservative amino acid substitution, such as from 25 to 75 conservative amino acid substitutions, for example from 75 to 125 conservative amino acid substitutions, such as from 125 to 175 conservative amino acid substitutions. Substitutions can be made within any one or more groups of predetermined amino acids.

Examples of fragments comprising one or more conservative amino acid substitutions including one or more conservative amino acid substitutions within the same group of predetermined amino acids, or a plurality of conservative amino acid substitutions, wherein each conservative substitution is generated by substitution within a different group of predetermined amino acids.

Accordingly, a variant of the sequences in FIG. 1, 2a or 2b, or fragments thereof according to the invention may comprise, within the same variant of the sequences in FIG. 1, 2a or 2b, or fragments thereof or among different variant of the sequences in FIG. 1, 2a or 2b, or fragments thereof, at least one substitution, such as a plurality of substitutions introduced independently of one another. Variants of the sequences in FIG. 1, 2a or 2b, or fragments thereof may thus comprise conservative substitutions independently of one another, wherein at least one glycine (Gly) of said variants of the sequences in FIG. 1, 2a or 2b, or fragments thereof of the sequences in FIG. 1, 2a or 2b is substituted with an amino acid selected from the group of amino acids consisting of Ala, Val, Leu, and Ile, and independently thereof, variants of the sequences in FIG. 1, 2a or 2b, or fragments thereof, wherein at least one of said alanines (Ala) of said variant of the sequences in FIG. 1, 2a or 2b, or fragments thereof is substituted with an amino acid selected from the group of amino acids consisting of Gly, Val, Leu, and Ile, and independently thereof, variant of the sequences in FIG. 1, 2a or 2b, or fragments thereof, wherein at least one valine (Val) of said variant of the sequences in FIG. 1, 2a or 2b, or fragments thereof is substituted with an amino acid selected from the group of amino acids consisting of Gly, Ala, Leu, and Ile, and independently thereof, variants of the sequences in FIG. 1, 2a or 2b, or fragments thereof, wherein at least one of said leucines (Leu) of said variant of the sequences in FIG. 1, 2a or 2b, or fragments thereof is substituted with an amino acid selected from the group of amino acids consisting of Gly, Ala, Val, and Ile, and independently thereof, variants of the sequences in FIG. 1, 2a or 2b, or fragments thereof, wherein at least one isoleucine (Ile) of said variants of the sequences in FIG. 1, 2a or 2b, or fragments thereof is substituted with an amino acid selected from the group of amino acids consisting of Gly, Ala, Val and Leu, and independently thereof, variants of the sequences in FIG. 1, 2a or 2b, or fragments thereof wherein at least one of said aspartic acids (Asp) of said variants of the sequences in FIG. 1, 2a or 2b, or fragments thereof is substituted with an amino acid selected from the group of amino acids consisting of Glu, Asn, and Gln, and independently thereof, variants of the sequences in FIG. 1, 2a or 2b, or fragments thereof, wherein at least one of said phenylalanines (Phe) of said variants of the sequences in FIG. 1, 2a or 2b, or fragments thereof is substituted with an amino acid selected from the group of amino acids consisting of Tyr, Trp, His, Pro, and preferably selected from the group of amino acids consisting of Tyr and Trp, and independently thereof, variants of the sequences in FIG. 1, 2a or 2b, or fragments thereof, wherein at least one of said tyrosines (Tyr) of said variants of the sequences in FIG. 1, 2a or 2b, or fragments thereof of the sequences in FIG. 1, 2a or 2b is substituted with an amino acid selected from the group of amino acids consisting of Phe, Trp, His, Pro, preferably an amino acid selected from the group of amino acids consisting of Phe and Trp, and independently thereof, variants of the sequences in FIG. 1, 2a or 2b, or fragments thereof, wherein at least one of said arginines (Arg) of said fragment of the sequences in FIG. 1, 2a or 2b is substituted with an amino acid selected from the group of amino acids consisting of Lys and His, and independently thereof, variants of the sequences in FIG. 1, 2a or 2b, or fragments thereof, wherein at least one lysine (Lys) of said variants of the sequences in FIG. 1, 2a or 2b, or fragments thereof is substituted with an amino acid selected from the group of amino acids consisting of Arg and His, and independently thereof, variants of the sequences in FIG. 1, 2a or 2b, or fragments thereof, wherein at least one of said aspargines (Asn) of said variants of the sequences in FIG. 1, 2a or 2b, or fragments thereof is substituted with an amino acid selected from the group of amino acids consisting of Asp, Glu, and Gin, and independently thereof, variants of the sequences in FIG. 1, 2a or 2b, or fragments thereof, wherein at least one glutamine (Gln) of said variants of the sequences in FIG. 1, 2a or 2b, or fragments thereof is substituted with an amino acid selected from the group of amino acids consisting of Asp, Glu, and Asn, and independently thereof, variants of the sequences in FIG. 1, 2a or 2b, or fragments thereof, wherein at least one proline (Pro) of said variants of the sequences in FIG. 1, 2a or 2b, or fragments thereof is substituted with an amino acid selected from the group of amino acids consisting of Phe, Tyr, Trp, and His, and independently thereof, variants of the sequences in FIG. 1, 2a or 2b, or fragments thereof, wherein at least one of said cysteines (Cys) of said variants of the sequences in FIG. 1, 2a or 2b, or fragments thereof is substituted with an amino acid selected from the group of amino acids consisting of Asp, Glu, Lys, Arg, His, Asn, Gln, Ser, Thr, and Tyr.

It is clear from the above outline that the same variant or fragment thereof may comprise more than one conservative amino acid substitution from more than one group of conservative amino acids as defined herein above.

The addition or deletion of an amino acid may be an addition or deletion of from 2 to 10 amino acids, such as from 10 to 20 amino acids, for example from 20 to 30 amino acids, such as from 40 to 50 amino acids. However, additions or deletions of more than 50 amino acids, such as additions from 10 to 200 amino acids, are also comprised within the present invention. More specifically, 43 N-terminal amino acids may be removed from the sequence in FIG. 1 without substantially altering the lipid binding effect of the protein. Such a deletion variant is included in SEQ ID NO 4 as the apolipoprotein part of the construct.

It will thus be understood that the invention concerns apolipoproteins comprising at least one fragment of the sequences in FIG. 1, 2a or 2b capable of binding lipids such as DPMC, including any variants and functional equivalents of such at least one fragment.

The apolipoprotein according to the present invention, including any functional equivalents and fragments thereof, may in one embodiment comprise less than 243 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

Fragments

A fragment comprising the lipid binding region of the native sequences in FIG. 1, 2a or 2b is particularly preferred. However, the invention is not limited to fragments comprising the lipid binding region. Deletions of such fragments generating functionally equivalent fragments of the sequences in FIG. 1, 2a or 2b comprising less than the lipid binding region are also comprised in the present invention. Functionally equivalent the sequences in FIG. 1, 2a or 2b peptides, and fragments thereof according to the present invention, may comprise less or more amino acid residues than the lipid binding region. Preferably, the fragment comprises at least the amino acids 100–186 of apo-A-I or a variant or a functional equivalent thereof. It has been determined that this central domain and the α-helices within the domain are directly involved in interactions with phospholipids. Therefore, it is highly likely that this region plays an important role in the functional properties of apo-A-I.

"Functional equivalency" as used in the present invention is according to one preferred embodiment established by means of reference to the corresponding functionality of a predetermined fragment of the sequences in FIG. 1, 2a or 2b.

Functional equivalents of variants of the sequences in FIG. 1, 2a or 2b will be understood to exhibit amino acid sequences gradually differing from the preferred predetermined sequence, as the number and scope of insertions, deletions and substitutions including conservative substitutions increases. This difference is measured as a reduction in homology between the preferred predetermined sequence and the fragment or functional equivalent.

All fragments or functional equivalents of apolipoprotein are included within the scope of this invention, regardless of the degree of homology that they show to a preferred predetermined sequence of apolipoprotein. The reason for this is that some regions of the sequences in FIG. 1, 2a or 2b are most likely readily mutatable, or capable of being completely deleted, without any significant effect on the binding activity of the resulting fragment.

A functional variant obtained by substitution may well exhibit some form or degree of native activity of the sequences in FIG. 1, 2a or 2b, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity between i) a given the sequences in FIG. 1, 2a or 2b fragment capable of effect and ii) a preferred predetermined fragment, is not a principal measure of the fragment as a variant or functional equivalent of a preferred predetermined the sequences in FIG. 1, 2a or 2b fragment according to the present invention.

The homology between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90. Preferably the algorithm BLOSUM 30 is used.

Fragments sharing at least some homology with the sequences in FIG. 1, 2a or 2b fragment are to be considered as falling within the scope of the present invention when they are at least about 40 percent homologous with the apolipoprotein or fragment thereof, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with the sequences in FIG. 1, 2a or 2b fragment.

According to one embodiment of the invention the homology percentages refer to identity percentages.

Additional factors that may be taken into consideration when determining functional equivalence according to the meaning used herein are i) the ability of antisera against one of the sequences in FIG. 1, 2a or 2b to detect fragments of the sequences in FIG. 1, 2a or 2b according to the present invention, or ii) the ability of the functionally equivalent fragment to compete with the sequences in FIG. 1, 2a or 2b in a lipid binding assay.

Conservative substitutions may be introduced in any position of a preferred predetermined apolipoprotein or fragment thereof. It may however also be desirable to introduce non-conservative substitutions, particularly, but not limited to, a non-conservative substitution in any one or more positions.

A non-conservative substitution leading to the formation of a functionally equivalent fragment of the sequences in FIG. 1, 2a or 2b would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or ii) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

The Component X

Preferably, the component X of the protein construct according to the invention is essentially non-immunogenic. For instance the component X may be an amino acid, a carbohydrate, a nucleic acid sequence, an inert protein or polypeptide, which has substantially no physiological effect and especially no immunological effect on mammals.

Preferably the component X is non inmmunogenic and does not interfere negatively with regard to ligand binding, i.e. the apolipoprotein component should not be directed at an undesired site through interactions of the X-component with a ligand.

According to one embodiment the component X consists of just one amino acid, which amino acid preferably is a cystein residue, which may be placed N-terminally, C-terminally or internally in the apolipoprotein component. Such a construct may form a dimer with other identical or similar constructs. Preferably a linker is introduced between the terminal cystein residue and the apolipoprotein component to facilitate the correct folding and lipid interaction of the construct.

However, more preferably the component X comprises a peptide having more than 1 amino acids such as more than 2 amino acids, for example more than 5 amino acids, such as more than 10 amino acids, for example more than 15 amino acids, such as more than 20 amino acids, such as more than 30 amino acids, for example more than 40 amino acids, such as more than 50 amino acids, for example more than 75 amino acids, such as more than 100 amino acids, for example more than 200 amino acids, such as more than 300 amino acids, for example more than 400 amino acids, such as more than 500 amino acids, for example more than 600 amino acids, such as more than 700 amino acids, for example more than 800 amino acids, such as more than 900 amino acids, for example more than 1000, 1250, 1500, 2000, or 2500 amino acids.

In the case where the X-component is a protein, this protein is preferably a mammalian protein and more preferably a human protein. Examples of suitable proteins include plasma proteins such as albumin or serum albumin or another non-immunogenic peptide or protein such as the serine protease fragment of plasminogen or another serine protease engineered to be inactive by disruption of the catalytic triad; and the constant region of the heavy chain of immunoglobins. More preferably, the protein comprises serum albumin. Even more preferably the protein comprises an apolipoprotein containing an amphipatic helix containing apolipoprotein.

According to an especially preferred embodiment of the invention, the component X comprises an apolipoprotein component selected from the group consisting of apolipoprotein A-I, A-II, AIV, an analogue, functional variant or fragment thereof. The two apolipoprotein components may be linked linearly or they may be linked via an additional non-native terminal cystein bridge.

Higher oligomers as well as dimers of the apolipoprotein component comprising at least one non-native cystein residue may be manufactured and linked through cystein bridges under appropriate conditions. Oligomers linked by disulphide bridges may be linked serially (apo-A-S-S-apo-A, or apo-A-S-S-apo-A-S-S-apo-A or higher oligomers).

The protein construct according to the invention may also comprise two, three or more apolipoproteins or analogues thereof being serially and covalently linked to one another. This may be achieved by linking the C-terminal of a first apolipoprotein to the N-terminus of the next apolipoprotein and so forth. The proteins may be so linked after transcription and translation or the nucleotide sequence may simply comprise two, three or more sequences coding for the apolipoprotein construct in question as well as optional linker peptides between the apolipoproteins.

Thereby, the need for a heterologous moiety to perform the linkage is avoided. It is expected that in the constructs having two, three or more apo-A units essentially all the apo-A units will participate in lipid binding thereby contributing to the functionality of the construct. Therefore it is expected that these multi-apo-A constructs have an increased lipid binding ability compared to native apo-A. An additional advantage of these constructs compared to native apo-A, is that they have an increased plasma half-life compared to native apo-A.

Such constructs comprising more than one apolipoprotein component may comprise a combination selected from the following group:

Dimers:
A-I A-I; A-II AII; A-IV A-IV; A-I A-II; A-I A-IV; A-II A-IV.

-continued

Trimers:
A-I A-II A-IV; A-I A-I A-II; A-I A-I A-I;
A-I A-I A-IV; A-II A-II A-I; A-II A-II A-IV;
A-II A-II A-II; A-IV A-IV A-IV; A-IV A-IV A-II;
A-IV A-IV A-I.

Oligomerisation Modules

According to an especially preferred embodiment of the invention, the heterologous moiety is an oligomerising module. In this context, an oligomerising module is a peptide or a protein or part of a protein which is capable of interacting with other, similar or identical oligomerising modules. The interaction is of the type that produces multimeric proteins or polypeptides. Such an interaction may be caused by covalent bonds between the components of the multimer as well as by hydrogen bond forces, hydrophobic forces, van der Waals forces, salt bridges. The invention also encompasses oligomerising modules of non-peptide nature such as a nucleic acid sequence of DNA, RNA, LNA, or PNA. The skilled person is familiar with techniques to link proteins and nucleic acid sequences to one another.

The oligomerisation module may be a dimerising module, a trimerising module, a tetramerising module, or a multimerising module.

When the apolipoprotein or analogue part of the construct is coupled to an oligomerising module, multimers of the construct can be made by simply mixing a solution of constructs (oligomerisation module linked to apolipoprotein part) under appropriate conditions. In this way, dimers, trimers, tretramers, pentamers, hexamers or higher—mers can be made depending on the type of oligomerising module being linked to the apolipoprotein part of the construct.

The multimers according to the invention may be homomers or heteromers, since different apolipoproteins can be linked to the oligomerising modules and be incorporated into the multimer. It may be advantageous to mix the different types of apolipoproteins in this way to obtain an improved clinical effect of the construct. Preferred homomers include trimers of Apo-A-I and trimers of Apo-A-IV.

According to an especially preferred embodiment of the invention the oligomerising module is from tetranectin and more specifically comprises the tetranectin trimerising structural element (hereafter termed TTSE, SEQ ID NO 12), which is described in detail in WO 98/56906. The amino acid sequence of TTSE is set forth in SEQ ID NO 12. The trimerising effect of TTSE is caused by a coiled coil structure which interacts with the coiled coil structure of two other TTSEs to form a trimer, which is exceptionally stable. A further advantage of TTSE is that it is a weak antigen (WO 98/56906).

Preferably the heparin binding site, which is located in the N-terminal region of exon 1 (FIG. 4) is abolished by removal or mutagenis of N-terminal lysine residues (residues 9 and 14 of SEQ ID NO 12) (Nielsen et al, 1997, FEBS Lett 412:388–396) without inhibiting trimerisation. Preferably the lysine residues are mutagenised to alanine. TTSEs that include most or all of exon 1 therefore confer an affinity for sulfated polysaccharides to any designed protein which encompasses such a TTSE as part of its structure. If desired, however, this affinity can be reduced or abolished by N-terminal truncation or mutagenesis of lysine residues in the part of the TTSE that corresponds to the N-terminal amino acid residues of tetranectin (Lorentsen et al 2000, Biochem J 347:83–87).

The interacting domain of the trimerising module according to the invention is preferably of the same type as in TTSE, namely a triple alpha helical coiled coil.

The TTSE may be from human tetranectin, from rabbit tetranectin, from murine tetranectin or from C-type lectin of shark cartilage. Preferably, the TTSE comprises a sequence having at least 68%, such as at least 75%, for example at least 81%, for example at least 87% such as at least 92% identity with the consensus sequence of SEQ ID NO 12. Thereby analogues of the TTSE having substantially the same trimerising effect are encompassed by the invention.

Preferably, the cystein residue 50 of TTSE (SEQ ID NO 12) should be mutagenised to serine, threonine, methionine or to any other amino acid residue in order to avoid formation of an unwanted inter-chain disulphide bridge, which could lead to unwanted multimerisation.

The presence of a trimer may be ascertained by well known techniques such as gel-filtration, SDS-PAGE, or native SDS gel electrophoresis depending on the nature of the trimer. One preferred method for ascertaining the presence of an oligomer is through linkage by DMSI (dimethylsubirimidate) followed by SDS-PAGE.

According to a preferred embodiment of the invention the protein construct is obtained by linking two or more apolipoproteins to oligomerising modules. The advantage of this embodiment is that the linkage of the individual apolipoproteins to one another does not take place within the apolipoprotein but in the oligomerising module. Thereby the nature of the wild-type apolipoprotein is conserved and the apolipoprotein conserves the secondary and tertiary structure, which is advantageous for its physiological function. By further introducing a peptide spacer between the apolipoprotein and the oligomerising module it is ensured that both of the components of the construct can perform their interaction with lipids and other oligomerising modules respectively without being affected by the interactions of the other component. Preferably, the peptide spacer is non-immunogenic, and has an essentially linear three dimensional structure.

Different or identical apo-A units may be oligomerised using an oligomerisation module such as a dimerising module, a trimerising module, a tetramerising module, a pentamerising module, a hexamerising module or a multimerising module. The oligomerising modules may comprise a coiled coil structure capable of interchain recognition and interaction.

The general method for producing an artificial trimer of a protein or peptide comprises the identification of a trimerisation module from proteins that form trimers in nature. Through careful analysis, the domain responsible for the protein-protein interaction can be identified, isolated, and linked to the protein or peptide to be trimerised. According to the invention such trimerisation does not necessarily comprise the formation of a trimer of apolipoprotein or an analogue. It is also possible to link just one apolipoprotein to a trimerisation module and allow this peptide to trimerise with two other trimerisation modules. Thereby the molecular weight of the apolipoprotein part is increased and the plama half-life may be increased compared to native apolipoprotein.

One example of an oligomerisation module is disclosed in WO 95/31540 (HOPPE ET AL.), which describes polypeptides comprising a collectin neck region. The amino acid sequence constituting the collectin neck region may be attached to any polypeptide of choice. Trimers can then be made under appropriate conditions between three polypeptides comprising the collectin neck region amino acid sequence.

Another example of an oligomerisation module is the α1-chain from Haptoglobin. The α1-chain has a cystein residue which may link to another α1-chain to form a dimer. A natural variant is the α2-chain, which has had part of the α1-chain involved in disulphide bridging duplicated. The α2-chain may form cystein bridges to cystein residues in other α2 or α1-chains thereby forming trimers, tetramers, pentamers, hexamers and higher—mers. In the natural form the α-chain is associated to a β-chain. It is possible to replace the β-chain with an apolipoprotein to make an apo-A-α-chain (haptoglobin) construct.

Spacer Peptide

The protein construct may also advantageously comprise a spacer moiety, which is covalently linked between the apolipoprotein or apolipoprotein analogue and the heterologous moiety. The effect of the spacer is to provide space between the heterologous moiety and the apolipoprotein part of the construct. Thereby is ensured that the secondary structure of the apolipoprotein part is not affected by the presence of the heterologous moiety so that the physiological effect of the apolipoprotein part is maintained. Preferably, the spacer is of polypeptide nature. In this way the nucleic acid sequence encoding the spacer can be linked to the sequence encoding the apolipoprotein part of the construct and optionally the sequence for the heterologous moiety, and the whole construct can be produced at the same time.

Design and preparation of suitable spacer moieties are known in the art and are conveniently effected by preparing fusion polypeptides having the format apo-A-spacer-X, where the spacer moiety is a polypeptide fragment (often a relatively inert one), so as to avoid undesired reactions between the spacer and the surroundings or the construct.

A spacer moiety may also be inserted between two TTSEs allowing both of these to interact with a third separate TTSE to form a trimeric complex, which then comprises two separate peptides: TTSE and TTSE-spacer-TTSE. This embodiment facilitates the production of the apolipoprotein construct since the major part of the trimer, which is then strictly seen a dimer, can be synthesised as one single polypeptide comprising in the fusion partners (apo-A denoting any polypeptide sequence forming the apolipoprotein part of the construct) apo-A-TTSE-spacer-TTSE-apo-A.

In the embodiments where two TTSEs are present in the same monomer it is preferred that the spacer moiety has a length and a conformation which favours complex formation involving both of the two TTSEs which are covalently linked by the spacer moiety. In this way, problems arising from undesired formation of trimers of the formats (2+1+1), (2+2+2), and (2+2+1) (wherein only one TTSE of monomer participates in complex formation) can be diminished.

The spacer peptide preferably comprises at least two amino acids, such as at least three amino acids, for example at least five amino acids, such as at least ten amino acids, for example at least 15 amino acids, such as at least 20 amino acids, for example at least 30 amino acids, such as at least 40 amino acids, for example at least 50 amino acids, such as at least 60 amino acids, for example at least 70 amino acids, such as at least 80 amino acids, such as at least 90 amino acids such as approximately 100 amino acids.

The spacer may be linked to the apo-A component and X through covalent linkages. and preferably the spacer is essentially non-immunogenic, and/or is not prone to proteolytic cleavage, and/or does not comprise any cystein residues.

Similarly, the three-dimensional structure of the spacer is preferably linear or substantially linear.

The following are examples of spacer sequences, which are believed to be especially preferable for linking apolipoprotein analogues to a component X. Preferred examples of spacer or linker peptides include those, which have been used to link proteins without substantially impairing the function of the linked proteins or at least without substantially impairing the function of one of the linked proteins. More preferably the linkers or spacers have been used to link proteins comprising coiled-coil structures.

Tetranectin Based Linker:

The linker may include the tetranectin residues 53–56, which in tetranectin forms a β-strand, and the residues 57–59 which forms a turn in tetranectin (Nielsen B B, Kastrup J S, Rasmussen H, Holtet T L, Graversen J H, Etzerodt M, Thøgersen H G, Larsen I K, FEBS-Letter 412, 388–396, 1997). The sequence of the segment is GTKVHNK (SEQ ID NO:69). This linker has the advantage that it in native tetranectin is bridging the trimerisation domain with the CRD-domain, and hence is imagined to be well suited for connecting the trimerisation domain to another domain in general. Furthermore the resulting construct is not expected to be more immunogenic than the construct without a linker. The tetranectin based linker is highly preferred when the component X comprises the TTSE.

Fibronectin Based Linker:

The linker may be chosen as a sub-sequence from the connecting strand 3 from human fibronectin, this corresponds to amino acid residues 1992–2102 (SWISS-PROT numbering, entry P02751). Preferably the subsequence: PGTSGQQPSVGQQ (SEQ ID NO:70) covering amino acid residues number 2037–2049 is used, and within that subsequence the segment GTSGQ (residues 2–6 of SEQ ID NO:70) corresponding to amino acid residues 2038–2042 is more preferable. This construct has the advantage that it is know not to be highly prone to proteolytic cleavage and is not expected to be highly immunogenic bearing in mind that fibronectin is present at high concentrations in plasma.

Human IgG$_3$ Upper Hinge Based Linker

The 10 amino acid residue sequence derived from the upper hinge region of murine IgG$_3$, PKPSTPPGSS (SEQ ID NO:71), has been used for the production of antibodies dimerised trough a coiled coil (Pack P. and Plückthun, A. Biochemistry 31, pp 1579–1584 (1992)) and may be useful as a spacer peptide according to the present invention. Even more preferable may be a corresponding sequence from the upper hinge region of human IgG$_3$. Sequences from human IgG$_3$ are not expected to be immunogenic in human beings.

Flexible Linkers

Possible examples of flexible linker/spacer sequences include SGGTSGSTSGTGST (SEQ ID NO:72), AGSSTGSSTGPGSTT (SEQ ID NO:73) or GGSGGAP (SEQ ID NO:74). These sequences have been used for the linking of designed coiled coils to other protein domains (MUller, K. M., Arndt, K. M. and Alber, T., Meth. Enzymology, 328, pp 261–281 (2000).

The Linkage

The two components of the construct may be linked together by a covalent linkage. This linkage may be formed between the component X and the C or N terminal amino acid of the apo-A component. The components may also be linked via more than one covalent linkages. The covalent linkage between the components may also comprise a S-S bridge, preferably between cystein residues. These cystein residues is placed C or N terminally in the apo-A component and terminally or internally in the component X.

Carbohydrate

Irrespective of the other components of the construct the construct according to the invention may comprise a carbohydrate moiety.

Tetranectin Trimerising Structural Element

One especially preferred embodiment of the invention is the trimerisation or partial trimerisation of an apolipoprotein or analogue thereof with the trimerisation module from tetranectin.

This technique is described in WO 98/56906 (THØGERSEN ET AL.), which is hereby incorporated by reference. The trimeric polypeptides are constructed as a monomer polypeptide construct comprising at least one tetranectin trimerising structural element (TTSE), which is covalently linked to at least one heterologous moiety. The tetranectin trimerising structural element is capable of forming a stable complex with two other tetranectin trimerising structural elements.

The term "trimerising structural element" (TTSE) used in the present description and claims is intended to refer to the portion of a polypeptide molecule of the tetranectin family which is responsible for trimerisation between monomers of the tetranectin polypeptide (SEQ ID NO 12). The term is also intended to embrace variants of a TTSE of a naturally occurring tetranectin family member, variants which have been modified in the amino acid sequence without adversely affecting, to any substantial degree, the trimerisation properties relative to those of the native tetranectin family member molecule.

Specific examples of such variants will be described in detail herein, but it is generally preferred that the TTSE is derived from human tetranectin, murine tetranectin, C-type lectin of human or bovine cartilage, or C-type lectin of shark cartilage. Especially preferred is monomer polypeptide constructs including at least one TTSE derived from human tetranectin.

The 51 residue polypeptide sequence encoded by exons 1 and 2 of tetranectin (FIG. 3, SEQ ID NO 12) appears to be unique to the tetranectin group of proteins (FIG. 4) as no significant sequence homology to other known polypeptide sequences has been established. In preparation for experimental investigations of the architecture of tetranectin a collection of recombinant proteins have been produced, the collection including complete tetranectin, the CRD domain (approximately corresponding to the polypeptide encoded by exon 3), a product corresponding to the polypeptide encoded by exons 2+3, a product corresponding to exons 1+2 (Holtet et al., 1996). Tetranectin is indeed a trimer, but the exon 2 encoded polypeptide is in fact capable of effecting trimerisation by itself as evidenced by the observation that the recombinant protein corresponding to exons 2+3 is in fact trimeric in solution.

3D-structure analysis of crystals of full-length recombinant tetranectin (Nielsen et al., 1996; Nielsen, 1996; Larsen et al., 1996; Kastrup, 1996) has shown that the polypeptide encoded in exon 2 plus three residues encoded in exon 3 form a triple alpha helical coiled coil structure.

From the combination of sequence and structure data it becomes clear that trimerisation in tetranectin is in fact generated by a structural element (FIG. 4), comprising the amino acid residues encoded by exon two and the first three residues of exon 3 by an unusual heptad repeat sequence, that apparently is unique to tetranectin and other members of its group: This amino acid sequence (FIG. 4) is characterised by two copies of heptad repeats (abcdefg) with hydrophobic residues at a and d positions as are other alpha helical coiled coils. These two heptad repeats are in sequence followed by an unusual third copy of the heptad repeat, where glutamine 44 and glutamine 47 not only substitute the hydrophobic residues at both the a and d position, but are directly involved in the formation of the triple alpha helical coiled coil structure. These heptad repeats are additionally flanked by two half-repeats with hydrophobic residues at the d and a position, respectively.

The presence of beta-branched hydrophobic residues at a or d positions in alpha helical coiled coil are known to influence the state of oligomerisation. In the tetranectin structural element only one conserved valine (number 37) is present. At sequence position 29 in tetranectin no particular aliphatic residue appears to be preferred.

In summary, it is apparent that the triple stranded coiled coil structure in tetranectin to a large extent is governed by interactions that are unexpected in relation to those characteristic among the group of known coiled coil proteins.

The TTSEs form surprisingly stable trimeric molecules. The experimental observations, that (1) a substantial part of the recombinant proteins exists in the oligomeric state of and can be cross-linked as trimeric molecules even at 70° C. and (2) that exchange of monomers between different trimers can only be detected after exposure to elevated temperature are evidence of a extremely high stability of the tetranectin trimerising structural element. This feature must be reflected in the amino acid sequence of the structural element. In particular, the presence and position of the glutamine containing repeat in the sequential array of heptad repeats is, together with the presence and relative position of the other conserved residues in the consensus sequence (FIG. 4), considered important for the formation of these stable trimeric molecules. For most practical uses the cysteine residue 50 should be mutagenized to serine, threonine, methionine or to any other amino acid residue in order to avoid formation of an unwanted inter-chain disulphide bridge, which may lead to uncontrolled multimerisation, aggregation and precipitation of a polypeptide product harbouring this sequence.

In particular in conjunction with the trimer-stabilising exon 1 encoded polypeptide, the tetranectin trimerising structural element is a truly autonomous polypeptide module retaining its structural integrity and propensity to generate a highly stable homotrimeric complex whether it is attached or not by a peptide bond at either or at both termini to other proteins.

This unique property is demonstrated by the fact that polypeptide sequences derived from heterologous proteins may readily be trimerised when joined as fusion proteins to the tetranectin trimerising structural element. This remains valid irrespective of whether the heterologous polypeptide sequences are placed amino-terminally or carboxy-terminally to the trimerising element allowing for the formation of one molecular assembly containing up to six copies of one particular polypeptide sequence or functional entities, or the formation of one molecular assembly containing up to six different polypeptide sequences, each contributing their individual functional property.

Since three TTSEs of naturally occurring human tetranectin forms up a triple alpha helical coiled coil, it is preferred that the stable complex formed by the TTSEs of the invention also forms a triple alpha helical coiled coil.

The "tetranectin family" are polypeptides, which share the consensus sequence shown in FIG. 4 or a sequence, which is homologous at sequence level with this consensus sequence.

Hence, monomer polypeptide constructs of the invention are preferred which comprise a polypeptide sequence which has at least 68% sequence identity with the consensus sequence shown in FIG. 4, but higher sequence identities are preferred, such as at least 75%, at least 81%, at least 87%, and at least 92%.

Trip A-Module

In the expression plasmids according to the present invention, the TTSE module (SEQ ID NO 12) was modified as indicated by replacing Cys 50 by Ser and including a C-terminal lysin residue. A SPGT sequence has been added to the N-terminal. This is a connective sequence to the trimerisation module. The sequence has been inserted because it gives the opportunity to cut the DNA strand with BglII and Kpn K. C-terminally a connective GS sequence has been added, which provides an opportunity to cut with BamHI. This modified TTSE is designated TripA and disclosed as SEQ ID NO 13. The trimerisation module of the Apo A construct may thus advantageously comprise this sequence or a sequence haveng at least 68% sequence identity with the sequence of SEQ ID NO 13, but higher sequence identities are preferred, such as at least 75%, at least 81%, at least 87%, and at least 92%.

Specific examples of constructs encompassing the Trip A module are disclosed in the examples.

Examples of Constructs According to The Invention

The invention encompasses the specific sequences disclosed in the appended examples as SEQ ID NO 2 to 11 and SEQ ID NO 14. Preferably the invention encompasses SEQ ID NO 3 to 11 and SEQ ID NO 14. Sequences sharing at least 60% sequence identity, such as at least 70% sequence identity to these sequences are also within the scope of the invention, preferably sequences sharing at least 80% sequence identity, more preferably at least 90%, more preferably at least 95%, more preferably at least 98%.

Production of The Protein Construct

In order to produce a peptide component of the protein construct the cDNA encoding this part is inserted into an expression vector and transformed into a host cell.

The above mentioned host cell (which is also a part of the invention) can be prepared by traditional genetic engineering techniques which comprises inserting a nucleic acid fragment (normally a DNA fragment) encoding the polypeptide part of a monomer polypeptide construct of the invention into a suitable expression vector, transforming a suitable host cell with the vector, and culturing the host cell under conditions allowing expression of the polypeptide part of the monomer polypeptide construct. The nucleic acid fragment encoding the polypeptide may be placed under the control of a suitable promoter which may be inducible or a constitutive promoter.

Depending on the expression system, the polypeptide may be recovered from the extracellular phase, the periplasm or from the cytoplasm of the host cell.

Suitable vector systems and host cells are well-known in the art as evidenced by the vast amount of literature and materials available to the skilled person. Since the present invention also relates to the use of the nucleic acid fragments of the invention in the construction of vectors and in host cells, the following provides a general discussion relating to such use and the particular considerations in practising this aspect of the invention.

In general, of course, prokaryotes are preferred for the initial cloning of nucleic sequences of the invention and constructing the vectors useful in the invention. For example, in addition to the particular strains mentioned in the more specific disclosure below, one may mention by way of example, strains such as E. coli K12 strain 294 (ATCC No. 31446), E. coli B, and E. coli X 1776 (ATCC No. 31537). These examples are, of course, intended to be illustrative rather than limiting.

Prokaryotes are also preferred for expression, since efficient purification and protein refolding strategies are available. The aforementioned strains, as well as *E. coli* W3110 (F-λ, prototrophic, ATCC No. 273325), *bacilli* such as *Bacillus subtilis*, or other enterobacteriaceae such as *Salmonella typhimurium* or *Serratia marcesans*, and various *Pseudomonas* species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells.

The pBR plasmid, or other microbial plasmid or phage must also contain, or be modified to contain, promoters which can be used by the microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilised, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used. Saccharomyces cerevisiae, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980).

This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilisation. Any plasmid vector containing a yeast compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure (Tissue Culture, 1973). Examples of such useful host cell lines are VERO and HeLa cells, Chinese hamster ovary (CHO) cell lines, and W138, BHK, COS-7 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the Bgll site located in the viral origin of replication. Further, it is also possible, and often desirable, to utilise promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

Upon production of the polypeptide monomer constructs it may be necessary to process the polypeptides further, e.g. by introducing non-proteinaceous functions in the polypeptide, by subjecting the material to suitable refolding conditions (e.g. by using the generally applicable strategies suggested in WO 94/18227), or by cleaving off undesired peptide moieties of the monomer (e.g. expression enhancing peptide fragments which are undesired in the end product).

In the light of the above discussion, the methods for recombinantly producing the monomer polypeptide construct of the invention are also a part of the invention, as are the vectors carrying and/or being capable of replicating the nucleic acids according to the invention in a host cell or a cell-line. According to the invention the expression vector can be e.g. a plasmid, a cosmid, a minichromosome, or a phage. Especially interesting are vectors which are integrated in the host cell/cell line genome after introduction in the host.

Another part of the invention are transformed cells (useful in the above-described methods) carrying and capable of replicating the nucleic acid fragments of the invention; the host cell can be a microorganism such as a bacterium, a yeast, or a protozoan, or a cell derived from a multicellular organism such as a fungus, an insect cell, a plant cell, or a mammalian cell. Especially interesting are cells from the bacterial species Escherichia, Bacillus and Salmonella, and a preferred bacterium is *E. coli*.

Yet another part of the invention relates to a stable cell line producing the polypeptide part of a construct according to the invention, and preferably the cell line carries and expresses a nucleic acid of the invention.

Receptor Binding

The performance of the constructs according to the invention may be analysed by measuring the ability of the constructs to bind to receptors or HDL proteins which may bind native apolipoprotein A-I, A-II or A-IV. Such receptors and proteins include but are not limited to cubilin, megalin, Scavenger receptor class B type 1 (SR-B1), ATP-binding cassette 1 (ABC1), Lecithin:cholesterol acyltransferase (LCAT), Cholesteryl-ester transfer protein (CETP), Phospolipid transfer protein (PLTP). The dissociation constant, Kd, of the complex between cubilin and native apolipoprotein AI is 20 nM. It has been determined experimentally that an apolipoprotein AI trimer according to the present invention binds even stronger to cubilin (FIG. 12).

Affinity Tags

The protein construct according to the invention may also comprise an affinity tag for use during purification of the construct. Such a tag preferably comprises a polyhistidine sequence. This sequence can advantageously be used for purification of the product on a $Ni^{2+}$ column, which will bind the polyhistidine sequence and thereby the whole protein. After elution from the column the polyhistidine sequence may be cleaved off by a proteinase such as trombin recognising a specific sequence built into the construct between the protein construct and the polyhistidine sequence.

Other examples of affinity tags include but are not limited to well known tags such as an antigenic tag, or a GST tag. A proteolytic cleavage site may be inserted between the tag and the construct to cleave off the tag.

Signal Peptides

When expressing the constructs according to the invention in *E. coli* or in yeast, it may be preferable to include a signal peptide in the expression construct to ensure that the expressed protein is secernated and can be harvested from the medium surrounding the cells instead of the more laborious process of isolating the expressed protein from within the cells. Specific examples of signal peptides for expression in yeast and *E. coli*, which can be used in conjunction with the present invention include those disclosed in WO 90/12879 (Sirtori et al), which discloses a signal peptide for expression of Apo-AI and Apo-AIM in yeast, and WO 94/13819 (Kabi Pharmacia) disclosing a signal peptide for expression of Apo-AI and Apo-AIM in *E. coli*.

Production of Apo-A-TTSE

In order to produce a construct comprising an apolipoprotein part and a TTSE, the cDNA encoding the apolipoprotein part is ligated at the 3' end to the 5' end of the c-DNA encoding the TTSE. Further TTSE units and apolipoprotein units may also be ligated. A sequence encoding an enzyme cleavage site is further ligated to the 3' end of the sequence encoding TTSE and finally a sequence encoding polyhistidine is also ligated. This can be done by conventional PCR techniques. The combined c-DNA is inserted into an expression vector and transformed into a host cell.

After expression in the *E. coli*, the polyhistidine sequence-is used to capture the heterologous protein on a Ni2+ column. After elution the polyhistidine tail can be removed by a proteinase such as Fx cleaving the heterologous protein at the specific site inserted into it between the TTSE and the polyhistidine sequence. The resulting apo-A-TTSE peptide can then be processed further by trimerising it to other or identical apo-A-TTSE peptides. To improve expression in *E. coli* it may be advantageous to express the construct as a fusion protein together with e.g. ubiquitin, which may be cleaved off later.

Use of an Apo-A construct for Preparation of a Pharmaceutical Composition

The apo-A construct may be used for the preparation of a pharmaceutical composition. The composition may comprise pharmaceutical acceptable excipients, adjuvants, additives such as phospholipids, cholesterol, or triglycerides.

The pharmaceutical composition may be administered intravenously, intraarterially, intramusculary, transdermally, pulmonary, subcutaneously, intradermally, intratechally, through the buccal-, anal-, vaginal-, conjunctival-, or intranasal tissue, or by inoculation into tissue, such as tumour tissue, or by an implant, or orally.

The formulation of the pharmaceutical compositions according to the invention is preferably performed using techniques well known to the skilled practitioner. This may comprise the addition of pharmaceutically acceptable excipients, adjuvants, or additives, such as phospholipids, cholesterol or triglycerides.

Administration of Apo-A Construct

The apo-A-constructs according to the invention may be administered for prevention and/or treatment of diseases related to cholesterol, phospholipids, and triacylglycerides, LDL and HDL disorders such as hypercholesterolemia, and arteriosclerotic diseases such as atherosclerosis and myocardial infarct. Other indications include angina pectoris, plaque angina pectoris, unstable angina pectoris, arterial stenoses such as carotis stenosis, claudicatio, or cerebral arterial stenosis. Furthermore, the apolipoprotein constructs may be used for removal of endotoxins.

In one embodiment, administration comprises the administration of at least 50 mg of the construct every week such as to obtain a plasma concentration of approximately 0.5 g/L. Preferably the construct is administered parenterally such as through injections, suppositories, implants etc. Preferably the composition is administered in an amount comprising at least 50 mg apolipoprotein construct per week, such as at least 100 mg/week, for example at least 250 mg/week, such as at least 500 mg/week, for example at least 750 mg/week such as at least 1000 mg/week, for example at least 1250 mg/week, such as at least 1500 mg/week, for example at least 2000 mg/week, such as at least 2500 mg/week, for example at least 5000 mg/week. The administration may be performed daily, every two or three days, once a week, once every second week, or once every third week, or once every fourth week.

According to another embodiment, the construct is administered once, twice or three times in much higher amounts especially for acute treatment of angina pectoris and plaque angina pectoris or unstable angina pectoris. The administration may be performed during 1, 2, 3, 4, 5, 6, 7, 8 or up to 10 days. These amounts may be at least 10 mg/kg body weight, such as at least 20 mg/kg body weight, for example at least 30 mg/kg, such as at least 40 mg/kg, for example at least 50 mg/kg, such as at least 60 mg/kg, for example at least 70 mg/kg, such as at least 75 mg/kg, for example at least 90 mg/kg, such as at least 100 mg/kg, for example at least 125 mg/kg, such as at least 150 mg/kg, for example at least 200 mg/kg, such as at least 250 mg/kg, for example at least 300 mg/kg, such as at least 400 mg/kg, for example at least 500 mg/kg, such as at least 600 mg/kg, for example at least 700 mg/kg, such as at least 800 mg/kg, for example at least 900 mg/kg, such as at least 1000 mg/kg.

The constructs may also be administered orally. For this administration route, the technology described in WO 99/46283, U.S. Pat. No. 5,922,680, U.S. Pat. No. 5,780,434 or U.S. Pat. No. 5,591,433, U.S. Pat. No. 5,609,871, or U.S. Pat. No. 5,783,193 may be applied to the protein constructs according to the present invention. These references are hereby incorporated in their entirety by reference.

Cell Population

The invention also encompasses the use of the nucleotide sequence according to the invention for gene therapy.

The genes may be transferred to a population of macrophages and subsequently be transferred to the patient in need of treatment. Hereby, a transient expression of the gene is obtained, since the macrophage have a limited lifetime in the blood vessels.

Permanent transfection may be obtained by transforming liver cells.

The invention is now described with specific examples of embodiments of the invention, which are to be interpreted as illustrative rather than limiting examples. The design of further constructs according to the invention lie within the normal skills of the practitioners within the art.

EXAMPLE 1

Cloning of Apo A-I

The cDNA encoding Apo A-I was amplified from a human liver cDNA library (Clontech) using standard PCR techniques. For the construction of Ubi-A-I the primers used were: 5'-CAC GGA TCC ATC GAG GGT AGG GGT GGA SAT GAA CCC CCC CAG AGC-3' (SEQ ID NO:75) and 5'-TCC AAG CTT ATT ACT GGG TGT TGA GCT TCT TAG TG-3' (SEQ ID NO:76). The product was cloned into the vector pT7H6Ubi, described in (Ellgaard L. et al Eur. J. Biochem. 1997;244(2):544–51) using the BamHI and Hind III cloning sites. For the construction of Trip-A-A-I the primers used were 5'-AAG GGA TCC GAT GAA CCC CCC CAG AGC CCC-3' (SEQ ID NO:77) and 5'-TCC AAG CTT ATT ACT GGG TGT TGA GCT TCT TAG TG-3' (SEQ ID NO:78). The PCR product was cloned into the pT7H6tripa vector described in WO 98/56906 using the BamHI and HindIII cloning sites. For the construction of Trip-A-I-de143 the primers used were 5'-AGG GGA TCC CTA AAG CTC CTT GAC AAC TGG G-3' (SEQ ID NO:79) and 5'-TCC AAG CTT ATT ACT GGG TGA GCT TCT TAG TG-3' (SEQ ID NO:80). The PCR product was cloned into the pT7H6tripa vector described in WO 98/56906 using the BamHI and HindIII cloning sites. For the construction of Ubi-Cys-A-I the primers used were: 5'-GGT GGA TCC ATC GAG GGT AGG GGT GGA TGT GAT GAA CCC CCC C-3' (SEQ ID NO:81) and 5'-TCC AAG CTT ATT ACT GGG TGT TGA GCT TCT TAG TG-3' (SEQ ID NO:82). The product was cloned inti the vector pT7H6Ubi, described in (Ellgaard L. et al Eur. J. Biochem. 1997;244(2):544–51) using the BamHI and HindIII cloning sites. The plasmids generated are shown on FIGS. 4, 5, 6, and 7.

EXAMPLE 2

Expression of Apolipoprotein A-I (apo A-I) in *E. coli*

Ubi-A-I and Trip-A-I as well as the other constructs disclosed in the figures are conveniently expressed in *E. coli* AV-1 cells (Stratagene Inc.). Other cell lines may be used as well. Culturing of the cells and induction of expression were performed as described for tetranectin in WO 98/56906.

EXAMPLE 3

Isolation and Processing of Protein

Crude protein was isolated by phenol extraction as described for tetranectin in WO 98/56906. The re-dissolved pellet from 6 liters of expression culture was centrifuged to remove non-dissolved material and then batch adsorbed to 50 ml $Ni^{2+}$-NTA-Sepharose, prepared as described in WO 98/56906. The column material was packed on a column and then washed with 500 ml 8 M urea, 500 mM NaCl, 50 mM Tris-HCl pH 8.0, then 200 ml of 6 M Guanidinium-HCl, 50 mM Tris-HCl pH 8.0 and finally 300 ml of 500 mM NaCl, 50 mM Tris-HCl pH 8.0. The protein was eluted with 500 mM NaCl, 50 mM Tris-HCl pH 8.0 and 10 mM EDTA. The protein was added 0.5 mg of Factor Xa and digested overnight at room temperature. Thrombin may be used for this purpose as well. The protein was gelfiltrated on a G-25 sephadex (Pharmacia) column in to a 500 mM NaCl, 50 mM Tris-HCl pH 8.0 buffer. Undigested protein was removed by passing the protein solution over a $Ni^{2+}$-NTA-Sepharose column pre-washed in 500 mM NaCl, 50 mM Tris-HCl pH 8.0 and then washed with 500 mM NaCl, 50 mM Tris-HCl pH 8.0. Undigested protein was eluted with 500 mM NaCl, 50 mM Tris-HCl pH 8.0 and 10 mM EDTA. Further purification may be performed using Sp Sepharose ion exchange.

EXAMPLE 4

Removal of Lipids from the Proteins

The proteins were gelfiltrated into a 10 mM $(NH_4)_2CO_3$ pH 8.8 solution and lyophilised. The lyophilised protein was resuspended in 25 ml cold 1:1 methanol/chloroform, incubated on ice for 30 min, centrifuged at 3000 g for 20 minutes. The pellet was resuspended in 25 ml of 1:2 cold methanol/chloroform, equilibrated for 30 minutes on ice and recentrifuged. The supernatant was removed and the pellet was briefly air-dried and then redissolved in 6 M guanidinium-HCl, 50 mM Tris-HCl pH 8.0 over night.

EXAMPLE 5

Multimerisation Assay

Cross linking

Multimerisation may be measured by cross-linking of multimers followed by analytical SDS-PAGE.

60 µl of a 0.2 mg/ml protein dissolved in 150 mM Na-borate pH 9.0 equillibrated to the desired temperature for 30 minutes are added 5 µl of a 20 mg/ml dimethylsuberimidate and incubated for 30 minutes at the desired temperature. The cross-linking was quenched by the addition of 5 µl 3 M Tris-HCl pH 9.0.

Dimethylsuberimidate causes lysin residues located within a short distance from one another to form a covalent bond. The result is that proteins which have formed multimers are covalently linked to one another. The molecular weight of the multimers can be estimated in the subsequent SDS-PAGE.

The cross-linking products were analysed by SDS-PAGE on 8–16% polyacrylamide gels. Optionally an adjuvant, such as a lipid, was included in the cross-linking mixture, in which case the protein was pre-incubated with the adjuvant.

Analytical Gelfiltration

Multimerisation may also be measured by analytical gelfiltration.

The protein was dissolved in a 500 mM NaCl, 50 mM Tris-HCl pH 8.0 buffer and gelfiltrated on a Superdex 200 HR 10/30 column in to the desired buffer at room temperature and a flow of 0.25 ml/min. For standard procedures the buffer was 100 mM NaCl, 50 mM Tris-HCl pH 8.0.

From FIG. 13 it can be seen that Apo A-I elutes as composite peaks, the major ones centred at approximately 14.5 and 16.5 mL. BSA, with a molecular weight of 68 kDa, elutes at approximately 14.5 ml, indicating that the Apo A-I peak at 16.5 ml corresponds to monomeric Apo A-I, while the other major peak corresponds to apo A-I self-association complexes. The constructs fused to the trimerisation domain all elute with a main peak at approximately 10.7 ml and a minor peak at 14 ml. The peak at 14 ml probably corresponds to the trimeric form of the constructs, while the main peak at 10.7 ml corresponds to a high molecular weight product. Presumably the product is formed by association of the trimers. This indicates that fusion of apo A-I to the trimerisation domain does not only lead to trimers, but also to the formation of large complexes, where the Apo A-I units can interact with other apo A-I units, like native apo A-I can interact with other Apo A-I molecules.

EXAMPLE 6

Kinetics of Association of The Protein Construct With Dimyristoyl Phosphatidylcholine (DMPC)

The ability of the constructs according to the invention to bind to a lipid can conveniently be measured using a well known assay such as the association to dimyristoyl phosphatidylcholine (DPMC).

The assay was conducted as described in (Bergeron J. et al. (1997), Biochem. Biophys. Acta, 1344, 139–152. Dried DPMC was suspended in 100 mM NaCl, 50 mM Tris-HCl pH 8.0 and 0.25 mM EDTA above its transition temparature at a concentration of 0.5 mg/ml. The protein sample, buffer and the DMPC suspension were all incubated at 24° C. 10 minutes, and then mixed so that the final concentration of DMPC became 0.4 mg/ml, with a protein conc. of 5.2 $\mu$M (of the monomer). The reduction in turbidity of the mixture, reflecting increasing lipid-protein association, was followed by measuring the absorbance of the mixture at 325 nm. The assay was conducted four times each for apo AI, Trip-A-AI and Trip-A-FN-AI, and one time without adding protein.

From FIG. 11 it can be seen that all Apo A-I constructs bind DMPC. For all the three constructs tested the turbidity was totally cleared after 24 hours, indicating that the capacity of the fusion proteins to bind DMPC is present in the fusion proteins. However, apparently both Trip-A-Apo A-I and Trip-A-FN-Apo AI binds DMPC slower than does native Apo A-I at 24° C., which is the only temperature at which the assay is functional.

EXAMPLE 7

Surface Plasmon Resonance Analysis of the Binding of the Derivatives to Cubilin The assay was conducted as described in: Kozyraki R, Fyfe J, Kristiansen M, Gerdes C, Jacobsen C, Cui S et al. The intrinsic factor-vitamin B12 receptor, cubilin, is a high-affinity apolipoprotein A-I receptor facilitating endocytosis of high-density lipoprotein. Nat Med 1999; 5(6):656–661. The concentration of apolipoprotein construct used was 0.5 $\mu$M. Results (FIG. 12) are only shown for TripA-AI and apo A-I. Binding similar to that observed for TripA-AI was observed for TripA-FN-AI and TripA-TN-AI. The response increased upon trimerisation of apo A-I, especially there was a decrease in the of-rate, based on the gained "avidity" of the interaction for a multimer with an immobilised target compared to a monomer (bonus of multivalency). Showing that apo A-I was able to bind cubilin in the trimeric state, and that more than one apo A-I was in a conformation capable of interacting with cubilin, indicating correct folding of the apo A-I unit in the trimeric construct.

EXAMPLE 8

Evaluation of The Plasma Clearance of Apolipoprotein A-I, TripA Apo-A-I and TripA Fibronectin-linker Apo-A-I in Mice Three groups of five mice each were each injected 1 mg of apo A-I, Trip-A-AI or Trip-A-FN-AI, respectively. The protein was dissolved at a concentration of 0.33 mg/ml in the following buffer: 1×PBS pH 7.4, and 8.9 mg/ml dipalmitoylphosphatidylcholine. Blood samples were taken from each mice at the following times after the injection: 10 min., 4 h, 24 h, and 48 h.

The plasma concentrations of apolipoprotein A-I and derivatives were measured using an ELISA assay as follows:

Nunc Immuno PolySorp plates were used, each vial was added 100 $\mu$L in each addition. MB corresponds to the following buffer composition: 2 mM $CaCl_2$, 1 mM $MgCl_2$, 10 mM HEPES, 140 mM NaCl.

Plates were coated overnight in cold-room with 4 $\mu$g/ml of polyclonal anti-human apo A-I from rabbit (DAKO A/S) dissolved in 50 mM$NaHCO_3$ pH 9.6. Plates were washed in MB+0.05% Tween-20 pH 7.8 and blocked in MB+0.05% Tween-20+1% BSA pH 7.8 for 1 hour. The sample was applied dissolved in MB+0.05% Tween-20+1% BSA pH 7.8 and incubated for 1 hour, washed in MB+0.05% Tween-20+ 1% BSA pH 7.8 and incubated for 1 hour with monoclonal anti-apo A-I from mice (PerImmune Inc, clone 10-A8) at a concentration of 1 $\mu$g/ml in MB+0.05% Tween-20+1% BSA pH 7.8. Plates were washed and incubated with a secondary anti-mice IgG antibody linked to horse radish peroxidase. Plates were washed again and developed using OPD-tablets and $H_2O_2$, the reaction was stopped using 1 M $H_2SO_4$. The result was compared to a standard based on known concentrations of apo A-I and derivatives, respectively. No effect of diluting Apo A-I in mice plasma was observed for the standard.

The results, shown in FIG. 14, verify that the plasma clearance time of the construct Trip A Apo A-I is increased at least 3 times compared to the clearance time of native Apo AI. Preliminary data indicate that the clearance time for Trip A FN Apo A-I is at least the same as for Trip A Apo A-I. These data together with the cubilin binding data and DMPC binding data document that the constructs according to the invention are strong candidates for treating the diseases mentioned in the present application.

EXAMPLE 9

Plasmids

The construct according to the invention may be manufactured using the plasmids disclosed below.

Insertion of a Linker Sequence in Trip-A-AI

The basic linker containing constructs, with the mutations mentioned, was constructed as was the construct with-out linker. I.e. by PCR amplification of Apo A-I (and the linker sequence) and insertion into the pT7FxH6-Trip-A plasmid. The reverse primer was the same as used for the construction of pT7H6FxTrip-A-AI, while the forward primers used were:

pT7H6FX-Trip-A-FN(-2)-AI:
5'-CGC GGATCC TCG GGT CAG GAT GAA CCC CCC CAG AGC CCC -3' (SEQ ID NO:83)

Unfortunately all the isolated clones had the above highlighted G mutated to a T, indicating a faulty sequence of the primer.

pT7H6FX-Trip-A-TN-AI-Bam-S
5'-cgc gga tcc aag gtg cac atg aag gat gaa ccc
ccc cag agc ccc-3' (seq id no:84)

The mutations mentioned was corrected by site directed mutagenesis using the QuickChange kit from Stratagene and the following sets of primers:

pT7H6FX-Trip-FN-AI:
5'-acg gtc tcc ctg aag gga acc tcg ggt cag gat g-3' (SEQ ID NO:85)

5'-cat cct gac ccg agg ttc cct tca ggg aga ccg t-3' pT7H6FX-Trip-A-TN-AI
5'-acg gtc tcc ctg aag gga acc aag gtg cac atg aag g-3' (SEQ ID NO:86)

5'-cct tca tgt gca cct tgg ttc cct tca ggg aga ccg t-3'

Removal of the Heparin-binding Site of Trip-A

As a further derivation of the constructs, the heparin binding site of the Trip-A sequence (Lorentsen R H, Graversen J H, et al. Biochemical Journal (2000), 347 pp 83–87, was mutated using the site directed mutagenseis kit from Stratagene and the following set of primers:

For the mutation of lysine 9 from Trip-A:

5'-cca acc cag aag ccc aag gcg aat gta aat gcc-3' (SEQ ID NO:87)

5'-gtg ttc aca aca tct gcc ttg gca ttt aca atc-3' (SEQ ID NO:88)

For the mutation of lysine 15 from Trip-A:

5'-ggc att tac aat cgc ctt ggg ctt ctg ggt tgg-3' (SEQ ID NO:89)

5'-cca acc cag aag ccc aag gcg aft gta aat gcc-3'

These mutations are planned to be made on all the relevant Trip-A-apo-AI derivatives, possibly them all. Generating double mutants K9A, K15A of the trip-A derivatives, named TripA-FN-AI-K9AK15A, TripA-TN-AI-K9AK15A and TripA-AI-K9AK15A.

Furthermore truncation of the N-terminal could also remove the heparin affinity without removing the trimerisation. See Holtet et al. Protein Science (1997), Lorentsen et al. Biochem. Journal (2000), Nielsen et al. FEBS (1997) and Nielsen et al Acta Cryst D. (2000). The N-terminal residue would then preferably be located between Val 16 and Met 22.

Construction of The Expression Plasmid for Hp-α-A-I

First the plasmid pT7H6Fx-Hp(alpha) (FIG. 10H) was constructed as follows:

From a cDNA library (Clontech fetal liver) the Hp-alpha sequence was PCR amplified using the following set of primers:

Non-sense primer: 5'-cac aag ctt tcc gct aga tct ctg cac tgg gtt agc cgg att ctt ggg-3' (SEQ ID NO:90)

Sense Primer: 5'-ggt gga tcc atc gag ggt agg ggt gtg gac tca ggc aat gat gtc acg g-3'-3' (SEQ ID NO:91)

The PCR product contained the flowing features:

BamHI-site—Hp alpha sequence—BglII site—HindIII site.

In the Hp-alpha sequence the cystein disulfide bridging with the beta-chain of Hp was mutated to an alanine.

The product was digested with BamHI and HindIII and inserted into the pT7H6FX plasmid, which was sequenced. A PCR product encoding human Apo AI was made using the standard non-sense primer also used for making pT7H6-Ubi-Fx-ApoAI and pT7H6Fx-TripA-AI. While the sense primer used was the one used as sense primer in the construction of pT7H6FX-TripA-AI. Giving a PCR product with the following features:

BamHI site—Apo AI sequence—HindIII site, this product was digested with BamHI and HindIII and inserted into the above mentioned plasmid digested with BglII and HindIII. The resulting plasmid pT7H6FX-Hp(alpha)-Apo AI was sequenced and expression tested in *E. coli.* pT7H6 TripA-apoAI (FIG. 7):

The plasmid comprises the plasmid pT7H6FxtripA described in WO 98/56906 as example no. 1.

Expression is governed by the T7 promoter. The plasmid furthermore comprises a H6 sequence being a hexa-His affinity tag for use in purification. After that is inserted a Factor Xa recognition sequence (IQGR).

SPGT is a connective sequence to the subsequent trimerisation module. This sequence has been inserted because it gives the opportunity to cut the DNA strand with BglII and KpnI.

Trip A is the trimerisation module from tetranectin. GS is another connective sequence, which provides an opportunity to cut with BamHI.

Finally the plasmid comprises the human apoliprotein A-I cDNA coding for amino acids 25–267 from human apolipoprotein A-I. The expressed and purified protein corresponds to SEQ ID NO 3.

pT7H6TripA-apoA1-del43 (FIG. 8):

The plasmid comprises the sequences as above, but the apolipoprotein part has been replaced with cDNA coding for amino acids 68–267 from human apolipoprotein A-I. The expressed and purified protein corresponds to SEQ ID NO 4 pT7H6UbiFxApoAI (FIG. 5):

The basic plasmid has been described in Eligaard et al (1997). The plasmid comprises the following sequences:

the expression is governed by the T7 promoter

H6: hexa-His affinity tag for purification of the protein construct

Ubi: cDNA coding for human ubiquitin inserted to stabilise the protein in *E. coli.*

FX: recognition sequence for Factor Xa

DNA coding for two Gly residues, necessary for the optimal cleavage by Factor Xa.

ApoAI: cDNA coding for amino acids 25–267 from human apolipoprotein A-I

The expressed and purified protein corresponds to SEQ ID NO 1.

pT7H6UbiFXCvsApoAI (FIG. 6):

As above, but after the sequence coding for the two glycine residues and before the apolipoprotein A-I sequence coding for a cysteine residue has been inserted. The expressed and purified protein corresponds to SEQ ID NO 2.

PT7H6FXCysApoAI (FIG. 9):

The plasmid comprises the following sequences:

the expression is governed by the T7 promoter

H6: hexa-His affinity tag for purification of the protein construct

FX: recognition sequence for Factor Xa

DNA coding for two Gly residues, necessary for the optimal cleavage by Factor Xa.

DNA coding for a cystein residue.

ApoAI: cDNA coding for amino acids 25–267 from human apolipoprotein A-I The expressed and purified protein corresponds to SEQ ID NO 2.

Further examples of plasmids for expression of apolipoprotein constructs according to the invention are disclosed in FIGS. 10A to G together with the corresponding amino acid sequences of the expressed and purified proteins, which are disclosed in the sequence listing.

References

Bergeron et al 1997, Biochem Biophys Acta, 1344:139–152.
Bolivar et al, 1977. Gene, 2:95.
Chang et al. 1978. Nature, 275:617–624.
Ellgaard et al (1997). Dissection of the domain architecture of the $\alpha_2$macroglobulin-receptor-associated protein. Eur J Biochem vol 244:544–551.
Fiers et al. 1978. Nature, 273:113.
Goeddel et al. 1979. Nature, 281:544.
Hess et al. 1969. Advances in Enzyme Regulation, 7:149–166.
Hitzman et al. 1980. Journal of Biological Chemistry, 25:12073–12080.
Holland et al. 1978. Biochemistry, 17:4900.
Holtet, T. L., Graversen, J. H., Thøgersen, H. C. and Etzerodt, M. (1996). Domains and shared motifs in plasminogen—ligand interaction. Poster 21st Annual Lorne Conference on Protein Structure and Function, held Melbourne, Australia, Feb. 4–8, 1996.
Itakura et al. 1977. Science, 198:1056.
Jones. 1977. Genetics, 85:23–33.
Kastrup, J. S. (1996). Lecture at Minisymposium held by EU HCM contract CHRX-CT93-0143: Protein Crystallography I in Hamburg, Germany, Dec. 13–14, 1996.
Kingsman et al, 1979, Gene: 141.
Larsen, I. K., Nielsen, B. B., Rasmussen, H. and Kastrup, J. S. (1996). Poster, 17th International Crystallography Congress, Seattle, USA held Aug. 8–17, 1996.
Neame, P. J. and Boynton, R. E. (1996). Protein Soc. Symposium, (Meeting date 1995; 9th Meeting: Tech. Prot. Chem VII). Proceedings pp. 401–407 (Ed., Marshak, D. R.; Publisher: Academic, San Diego, Calif.).
Nielsen, B. B. (1996). Lecture, Lundbeck Centre Neuro-Medicinal Chemistry Minisymposium held Nov. 5, 1996 at the Royal Danish School of Pharmacy, Copenhagen.
Nielsen, B. B., Larsen, I. K., Rasmussen, H. and Kastrup, J. S. (1996). Lecture, Danish Crystallographer's Meeting, held Jun. 3–4, 1996 at the Royal Danish School of Pharmacy, Copenhagen.
Siebwenlist et al. 1980. Cell, 20:269.
Sørensen et al, 1995, Gene, 152:243–245.
Stinchomb et al. 1979. Nature 282:39.
Tschemper et al. 1980. Gene, 10:157.

What is claimed is:

1. A pharmaceutical composition comprising an apolipoprotein protein construct having the general formula apo-A-X, where apo-A is an apolipoprotein component selected from the group consisting of apolipoprotein A-I, apolipoprotein A-II, apolipoprotein A-IV, and X is a teeranectin trimerising module.

2. The composition of claim 1, further comprising a spacer peptide between the apo-A component and the tetranectin trimerising module, wherein the spacer peptide comprises at least two amino acids.

3. The composition according to claim 2, wherein the spacer peptide is essentially non-immunogenic, and/or is not prone to proteolytic cleavage and/or does not comprise any cystein residues.

4. The composition according to claim 2, wherein the three-dimensional structure of the spacer linear.

5. The composition according to claim 2, wherein the spacer peptide comprises an amino acid sequence selected from the group consisting of GTKVHMK (SEQ ID NO:69) PGTSGQQPSVGQQ (SEQ ID NO:70), GTSGQ (residues 2–6 of SEQ ID NO:70), PKPSTPPGSS (SEQ ID NO:71), SGGTSGSTSGTGST (SEQ in NQ:72), AGSSTGSSTGPG-STT (SEQ ID NO:73) and GGSGGAP (SEQ ID NO:74).

6. The composition of claim 1, wherein the tetranectin trimerising module is linked by a covalent link to the N-terminal or the C-terminal amino acid of apo-A.

7. The composition of claim 1, wherein the tetranectin trimerising module is part of a stable trimeric complex with two other tetranectin trimerising modules.

8. The composition of claim 7, wherein the stable trimeric complex includes a coiled coil structure.

9. The composition of claim 8, wherein the coiled coil structure is a triple alpha helical coiled coil.

10. The composition of claim 7, wherein the stable trimeric complex comprises two tetranectin trimerising modules linked by a spacer moiety, which allows both of the two tetranectin trimerising modules to take part in the complex formation with a third tetranectin trimerising module not being part of the apolipoprotein protein construct.

11. The composition of claim 1, wherein the tetranectin trimerising module is selected from the group consisting of human tetranectin, murine tetranectin or C-type lectin of human, bovine or shark cartilage.

12. The composition of claim 1, wherein the tetranectin trimerising module comprises a sequence having at least 68% identity with the sequence of SEQ ID NO 12 and is capable of forming a stable trimeric complex with other tetranectin trimerising modules.

13. The composition of claim 12, wherein the cysteine residue 50 in SEQ ID NO 12 is substituted by a serine residue, a threonine residue, or a methionine residue.

14. The composition of claim 1, wherein the tetranectin trimerisation module has at least 68% sequence identity with the Trip A module (SEQ ID NO 13) and is capable of forming a stable trimeric complex with other tetranectin trimerising modules.

15. The composition of claim 7, wherein the stable trimeric complex has a half-life at least 2 times the half-life of native apolipoprotein A-I, A-II or A-IV.

16. The composition of claim 7, wherein said stable trimeric complex is capable of binding to a receptor or protein selected from the group consisting of cubilin, megalin, Scavenger receptor class B, type 1 (SR-B1), ATP-binding cassette 1 (ABC1), Lecithin:cholesterol acyltransferase (LCAT), Cholesteryl-ester transfer protein (CETP), and Phospolipid transfer protein (PLTP).

17. The composition according to claim 16, wherein the trimeric complex comprises an amino acid sequence having at least 70% sequence identity to one of the sequences SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10 or SEQ ID NO 11.

18. The composition of claim 1, further comprising pharmaceutical acceptable excipients, adjuvants, or additives.

19. An apolipoprotein protein construct having the general formula apo-A-X, where apo-A is an apolipoprotein component selected from the group consisting of apolipoprotein A-I, apolipoprotein A-II, and apolipoprotein A-IV, and X is a tetranectin trimerising module.

20. The construct of claim 19, further comprising a spacer peptide between the apo-A component and the tetranectin trimerising module, wherein the spacer peptide comprises at least two amino acids.

21. The construct according to claim 20, wherein the spacer peptide is essentially non-immunogenic, and/or is not prone to proteolytic cleavage and/or does not comprise any cysteine residues.

22. The construct according to claim 20, wherein the three-dimensional structure of the spacer peptide is linear.

23. The construct according to claim 20, wherein the spacer peptide comprises an amino acid sequence selected from the group consisting of GTKVHMK (SEQ ID NO:69), PGTSGQQPSVGQQ (SEQ ID NO:70), GTSGQ (residues 2–6 of SEQ ID NO:70), PKPSTPPGSS (SEQ ID NO:71), SGGTSGSTSGTGST (SEQ ID NO:72), AGSSTCSSTG-PGSTT (SEQ ID NO:73) and GGSGGAP (SEQ ID NO:74).

24. The construct of claim 19, wherein the tetranectin trimerising module is part of a stable trimeric complex with two other tetranectin trimerising modules.

25. The construct of claim 24, wherein the stable complex comprises a coiled coil structure.

26. The construct of claim 25, wherein the coiled coil structure is a triple alpha helical coiled coil.

27. The construct of claim 24, wherein the stable trimeric complex comprises two tetranectin trimerising modules linked by a spacer moiety, which allows both of the two tetranectin trimerising modules to take part in the complex formation with a third tetranectin trimerising module not being part of the apolipoprotein protein construct.

28. The construct of claim 24, wherein the tetranectin trimerising module is selected from the group consisting of human tetranectin, murine tetranectin or C-type lectin of human, bovine or shark cartilage.

29. The construct of claim 24, wherein the tetranectin trimerising module comprises a sequence having at least 68% sequence identity with the sequence of SEQ ID NO 12 and is capable of forming a stable trimeric complex with other tetranectin trimerising modules.

30. The construct of claim 29, wherein the cysteine residue 50 in SEQ ID NO 12 is substituted by a serine residue, a threonine residue, or a methionine residue.

31. The construct of claim 24, wherein the tetranectin trimerising module has at least 68% sequence identity with the Trip A module (SEQ ID NO 13) and is capable of forming a stable trimeric complex with other tetranectin trimerising modules.

32. The composition of claim 7, wherein the stable trimeric cowplex has a half-life at least 3 times the half-life of native apolipoprotein A-I, A-II or A-IV.

33. The composition of claim 7, wherein the stable trimeric complex has a half-life at least 4 time the half-life of native apolipoprotein A-I, A-II or A-IV.

34. The composition of claim 7, wherein the stable trimeric complex has a half-life at least 10 times the half-life of native apolipoprotein A-I, A-II or A-IV.

35. The composition of claim 1, wherein the apolipoprotein A-I is human apolipoprotein A-I.

36. The composition of claim 1, wherein apo-A is a fragment of human apolipoprotein A-I, where said fragment substantially retains the lipid binding function of human apolipoprotein A-I.

37. The composition of claim 36, wherein the fragment of human apolipoprotein A-I comprises at least the amino acids 100–186 of human apolipoprotein A-I.

38. The composition of claim 36, wherein the fragment of human apolipoprotein A-I comprises at least the amino acids 25–267 of human apolipoprotein A-I (SEQ ID NO 1).

39. The composition of claim 36, wherein the fragment of human apolipoprotein A-I is amino acids 68–267 from human apolipoprotein A-I.

40. The construct according to claim 19, wherein the tetranectin trimerising module is linked by a covalent link to the N-terminal or the C-terminal amino acid of apo-A.

41. The construct of claim 24, wherein the stable trimeric complex has a half-life at least 2 times the half-life of native apolipoprotein A-I, A-II or A-IV.

42. The construct of claim 24, wherein the stable trimeric complex has a half-life at least 3 times the half-life of native apolipoprotein A-I, A-II or A-IV.

43. The construct of claim 24, wherein the stable trimeric complex has a half-life at least 4 times the half-life of native apolipoprotein A-I, A-II or A-IV.

44. The construct of claim 24, wherein the stable trimeric complex has a half-life at least 10 times the half-life of native apolipoprotein A-I, A-II or A-IV.

45. The construct of claim 19, wherein apo-A is human apolipoprotein A-I.

46. The construct of claim 24, wherein apo-A is a fragment of human apolipoprotein A-I where said fragment substantially retains the lipid binding function of human apolipoprotein A-I.

47. The construct of claim 46, wherein the fragment of human apolipoprotein A-I comprises at least the amino acids 100–186 of human apolipoprotein A-I.

48. The construct of claim 46, wherein the fragment of human apolipoprotein A-I comprises at least the amino acids 25–267 of human apolipoprotein A-I (SEQ ID NO 1).

49. The construct of claim 46, wherein the fragment of human apolipoprotein A-I is amino acids 68–267 from human apolipoprotein A-I.

50. The construct of claim 24, wherein said stable trimeric complex is capable of binding to a receptor or protein selected from the group consisting of cubilin, megalin, Scavenger receptor class B, type 1 (SR-B1), ATP-binding cassette 1 (ABC1), Lecithin:cholesterol acyltransferase (LCAT), Cholesteryl-ester transfer protein (CETP), and Phospolipid transfer protein (PLTP).

51. The construct according to claim 50, wherein the trimeric complex comprises an amino acid sequence having at least 70% sequence identity to at least one of the sequences SEQ ID NO 3, SEQ ID NO 4, SEQ ID NO 5, SEQ ID NO 6, SEQ ID NO 7, SEQ ID NO 8, SEQ ID NO 9, SEQ ID NO 10 or SEQ ID NO 11.

52. A trimeric complex consisting essentially of three apolipoprotein protein constructs, each construct having the general formula apo-A-X, where apo-A is an apolipoprotein component selected from the group consisting of apolipoprotein A-I, apolipoprotein A-II, and apolipoprotein A-IV, and X is a tetranectin trimerising module.

53. The composition of claim 36, wherein said fragment retains all of the lipid binding function of human apolipoprotein A-I.

54. The construct of claim 46, wherein said fragment retains all of the lipid binding function of human apolipoprotein A-I.

* * * * *

SEQUENCE LISTING

<160> NUMBER OF SEQ ID NOS: 91

<210> SEQ ID NO 1
<211> LENGTH: 243
<212> TYPE: PRT
<213> ORGANISM: Homo sapiens

<400> SEQUENCE: 1

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175
```

```
Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
        210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 244
<212> TYPE: PRT
<213> ORGANISM: Homo sapiens
<220> FEATURE:
<221> NAME/KEY: misc_feature
<222> LOCATION: (1)..(1)
<223> OTHER INFORMATION: N-terminal Cys
<221> NAME/KEY: misc_feature
<222> LOCATION: (2)..(244)
<223> OTHER INFORMATION: Amino acids 25-267 from human ApoA1

<400> SEQUENCE: 2

Cys Asp Glu Pro Pro Gln Ser Pro Trp Asp Arg Val Lys Asp Leu Ala
1               5                   10                  15

Thr Val Tyr Val Asp Val Leu Lys Asp Ser Gly Arg Asp Tyr Val Ser
            20                  25                  30

Gln Phe Glu Gly Ser Ala Leu Gly Lys Gln Leu Asn Leu Lys Leu Leu
        35                  40                  45

Asp Asn Trp Asp Ser Val Thr Ser Thr Phe Ser Lys Leu Arg Glu Gln
    50                  55                  60

Leu Gly Pro Val Thr Gln Glu Phe Trp Asp Asn Leu Glu Lys Glu Thr
65                  70                  75                  80

Glu Gly Leu Arg Gln Glu Met Ser Lys Asp Leu Glu Glu Val Lys Ala
                85                  90                  95

Lys Val Gln Pro Tyr Leu Asp Asp Phe Gln Lys Lys Trp Gln Glu Glu
            100                 105                 110

Met Glu Leu Tyr Arg Gln Lys Val Glu Pro Leu Arg Ala Glu Leu Gln
        115                 120                 125

Glu Gly Ala Arg Gln Lys Leu His Glu Leu Gln Glu Lys Leu Ser Pro
    130                 135                 140

Leu Gly Glu Glu Met Arg Asp Arg Ala Arg Ala His Val Asp Ala Leu
145                 150                 155                 160

Arg Thr His Leu Ala Pro Tyr Ser Asp Glu Leu Arg Gln Arg Leu Ala
                165                 170                 175

Ala Arg Leu Glu Ala Leu Lys Glu Asn Gly Gly Ala Arg Leu Ala Glu
            180                 185                 190

Tyr His Ala Lys Ala Thr Glu His Leu Ser Thr Leu Ser Glu Lys Ala
        195                 200                 205

Lys Pro Ala Leu Glu Asp Leu Arg Gln Gly Leu Leu Pro Val Leu Glu
    210                 215                 220

Ser Phe Lys Val Ser Phe Leu Ser Ala Leu Glu Glu Tyr Thr Lys Lys
225                 230                 235                 240

Leu Asn Thr Gln
```

<210> SEQ ID NO 3
<211> LENGTH: 301
<212> TYPE: PRT
<213> ORGANISM: Homo sapiens
<220> FEATURE:
<221> NAME/KEY: misc_feature
<222> LOCATION: (1)..(58)
<223> OTHER INFORMATION: Trimerisation module from tetranectin
<221> NAME/KEY: misc_feature
<222> LOCATION: (59)..(301)
<223> OTHER INFORMATION: Mature ApoA1

<400> SEQUENCE: 3

```
Ser Pro Gly Thr Glu Pro Pro Thr Gln Lys Pro Lys Lys Ile Val Asn
 1               5                  10                  15

Ala Lys Lys Asp Val Val Asn Thr Lys Met Phe Glu Glu Leu Lys Ser
            20                  25                  30

Arg Leu Asp Thr Leu Ala Gln Glu Val Ala Leu Leu Lys Glu Gln Gln
        35                  40                  45

Ala Leu Gln Thr Val Ser Leu Lys Gly Ser Asp Glu Pro Pro Gln Ser
    50                  55                  60

Pro Trp Asp Arg Val Lys Asp Leu Ala Thr Val Tyr Val Asp Val Leu
65                  70                  75                  80

Lys Asp Ser Gly Arg Asp Tyr Val Ser Gln Phe Glu Gly Ser Ala Leu
                85                  90                  95

Gly Lys Gln Leu Asn Leu Lys Leu Leu Asp Asn Trp Asp Ser Val Thr
            100                 105                 110

Ser Thr Phe Ser Lys Leu Arg Glu Gln Leu Gly Pro Val Thr Gln Glu
        115                 120                 125

Phe Trp Asp Asn Leu Glu Lys Glu Thr Glu Gly Leu Arg Gln Glu Met
    130                 135                 140

Ser Lys Asp Leu Glu Glu Val Lys Ala Lys Val Gln Pro Tyr Leu Asp
145                 150                 155                 160

Asp Phe Gln Lys Lys Trp Gln Glu Glu Met Glu Leu Tyr Arg Gln Lys
                165                 170                 175

Val Glu Pro Leu Arg Ala Glu Leu Gln Glu Gly Ala Arg Gln Lys Leu
            180                 185                 190

His Glu Leu Gln Glu Lys Leu Ser Pro Leu Gly Glu Glu Met Arg Asp
        195                 200                 205

Arg Ala Arg Ala His Val Asp Ala Leu Arg Thr His Leu Ala Pro Tyr
    210                 215                 220

Ser Asp Glu Leu Arg Gln Arg Leu Ala Ala Arg Leu Glu Ala Leu Lys
225                 230                 235                 240

Glu Asn Gly Gly Ala Arg Leu Ala Glu Tyr His Ala Lys Ala Thr Glu
                245                 250                 255

His Leu Ser Thr Leu Ser Glu Lys Ala Lys Pro Ala Leu Glu Asp Leu
            260                 265                 270

Arg Gln Gly Leu Leu Pro Val Leu Glu Ser Phe Lys Val Ser Phe Leu
        275                 280                 285

Ser Ala Leu Glu Glu Tyr Thr Lys Lys Leu Asn Thr Gln
    290                 295                 300
```

<210> SEQ ID NO 4
<211> LENGTH: 258
<212> TYPE: PRT
<213> ORGANISM: Homo sapiens

```
<220> FEATURE:
<221> NAME/KEY: misc_feature
<222> LOCATION: (1)..(58)
<223> OTHER INFORMATION: Trimerisation module from tetranectin
<221> NAME/KEY: misc_feature
<222> LOCATION: (59)..(258)
<223> OTHER INFORMATION: Amion acids 68-267 from human Apo A1

<400> SEQUENCE: 4
```

| | | | | | | | | | | | | | | |
|---|---|---|---|---|---|---|---|---|---|---|---|---|---|---|
| Ser | Pro | Gly | Thr | Glu | Pro | Pro | Thr | Gln | Lys | Pro | Lys | Lys | Ile | Val | Asn |
| 1 | | | | 5 | | | | | 10 | | | | | 15 | |
| Ala | Lys | Lys | Asp | Val | Val | Asn | Thr | Lys | Met | Phe | Glu | Glu | Leu | Lys | Ser |
| | | | 20 | | | | | 25 | | | | | 30 | | |
| Arg | Leu | Asp | Thr | Leu | Ala | Gln | Glu | Val | Ala | Leu | Leu | Lys | Glu | Gln | Gln |
| | | | 35 | | | | | 40 | | | | | 45 | | |
| Ala | Leu | Gln | Thr | Val | Ser | Leu | Lys | Gly | Ser | Leu | Lys | Leu | Leu | Asp | Asn |
| | 50 | | | | | 55 | | | | | 60 | | | | |
| Trp | Asp | Ser | Val | Thr | Ser | Thr | Phe | Ser | Lys | Leu | Arg | Glu | Gln | Leu | Gly |
| 65 | | | | | 70 | | | | | 75 | | | | | 80 |
| Pro | Val | Thr | Gln | Glu | Phe | Trp | Asp | Asn | Leu | Glu | Lys | Glu | Thr | Glu | Gly |
| | | | | 85 | | | | | 90 | | | | | 95 | |
| Leu | Arg | Gln | Glu | Met | Ser | Lys | Asp | Leu | Glu | Glu | Val | Lys | Ala | Lys | Val |
| | | | 100 | | | | | 105 | | | | | 110 | | |
| Gln | Pro | Tyr | Leu | Asp | Asp | Phe | Gln | Lys | Lys | Trp | Gln | Glu | Glu | Met | Glu |
| | | | 115 | | | | | 120 | | | | | 125 | | |
| Leu | Tyr | Arg | Gln | Lys | Val | Glu | Pro | Leu | Arg | Ala | Glu | Leu | Gln | Glu | Gly |
| | 130 | | | | | 135 | | | | | 140 | | | | |
| Ala | Arg | Gln | Lys | Leu | His | Glu | Leu | Gln | Glu | Lys | Leu | Ser | Pro | Leu | Gly |
| 145 | | | | | 150 | | | | | 155 | | | | | 160 |
| Glu | Glu | Met | Arg | Asp | Arg | Ala | Arg | Ala | His | Val | Asp | Ala | Leu | Arg | Thr |
| | | | | 165 | | | | | 170 | | | | | 175 | |
| His | Leu | Ala | Pro | Tyr | Ser | Asp | Glu | Leu | Arg | Gln | Arg | Leu | Ala | Ala | Arg |
| | | | 180 | | | | | 185 | | | | | 190 | | |
| Leu | Glu | Ala | Leu | Lys | Glu | Asn | Gly | Gly | Ala | Arg | Leu | Ala | Glu | Tyr | His |
| | | | 195 | | | | | 200 | | | | | 205 | | |
| Ala | Lys | Ala | Thr | Glu | His | Leu | Ser | Thr | Leu | Ser | Glu | Lys | Ala | Lys | Pro |
| | 210 | | | | | 215 | | | | | 220 | | | | |
| Ala | Leu | Glu | Asp | Leu | Arg | Gln | Gly | Leu | Leu | Pro | Val | Leu | Glu | Ser | Phe |
| 225 | | | | | 230 | | | | | 235 | | | | | 240 |
| Lys | Val | Ser | Phe | Leu | Ser | Ala | Leu | Glu | Glu | Tyr | Thr | Lys | Lys | Leu | Asn |
| | | | | 245 | | | | | 250 | | | | | 255 | |
| Thr | Gln | | | | | | | | | | | | | | |

```
<210> SEQ ID NO 5
<211> LENGTH: 301
<212> TYPE: PRT
<213> ORGANISM: Homo sapiens
<220> FEATURE:
<221> NAME/KEY: misc_feature
<222> LOCATION: (1)..(58)
<223> OTHER INFORMATION: Trimerisation module from tetranectin
<221> NAME/KEY: misc_feature
<222> LOCATION: (9)..(9)
<223> OTHER INFORMATION: Mutagen
<221> NAME/KEY: misc_feature
<222> LOCATION: (15)..(15)
<223> OTHER INFORMATION: Mutagen
<221> NAME/KEY: misc_feature
<222> LOCATION: (59)..(301)
<223> OTHER INFORMATION: Apo-A1 mature
```

```
<400> SEQUENCE: 5

Ser Pro Gly Thr Glu Pro Pro Thr Gln Lys Pro Lys Ala Ile Val Asn
1               5                   10                  15

Ala Lys Ala Asp Val Val Asn Thr Lys Met Phe Glu Glu Leu Lys Ser
            20                  25                  30

Arg Leu Asp Thr Leu Ala Gln Glu Val Ala Leu Leu Lys Glu Gln Gln
                35                  40                  45

Ala Leu Gln Thr Val Ser Leu Lys Gly Ser Asp Glu Pro Pro Gln Ser
        50                  55                  60

Pro Trp Asp Arg Val Lys Asp Leu Ala Thr Val Tyr Val Asp Val Leu
65                  70                  75                  80

Lys Asp Ser Gly Arg Asp Tyr Val Ser Gln Phe Glu Gly Ser Ala Leu
                85                  90                  95

Gly Lys Gln Leu Asn Leu Lys Leu Leu Asp Asn Trp Asp Ser Val Thr
            100                 105                 110

Ser Thr Phe Ser Lys Leu Arg Glu Gln Leu Gly Pro Val Thr Gln Glu
                115                 120                 125

Phe Trp Asp Asn Leu Glu Lys Glu Thr Glu Gly Leu Arg Gln Glu Met
130                 135                 140

Ser Lys Asp Leu Glu Glu Val Lys Ala Lys Val Gln Pro Tyr Leu Asp
145                 150                 155                 160

Asp Phe Gln Lys Lys Trp Gln Glu Glu Met Glu Leu Tyr Arg Gln Lys
                165                 170                 175

Val Glu Pro Leu Arg Ala Glu Leu Gln Glu Gly Ala Arg Gln Lys Leu
            180                 185                 190

His Glu Leu Gln Glu Lys Leu Ser Pro Leu Gly Glu Glu Met Arg Asp
        195                 200                 205

Arg Ala Arg Ala His Val Asp Ala Leu Arg Thr His Leu Ala Pro Tyr
    210                 215                 220

Ser Asp Glu Leu Arg Gln Arg Leu Ala Ala Arg Leu Glu Ala Leu Lys
225                 230                 235                 240

Glu Asn Gly Gly Ala Arg Leu Ala Glu Tyr His Ala Lys Ala Thr Glu
                245                 250                 255

His Leu Ser Thr Leu Ser Glu Lys Ala Lys Pro Ala Leu Glu Asp Leu
            260                 265                 270

Arg Gln Gly Leu Leu Pro Val Leu Glu Ser Phe Lys Val Ser Phe Leu
        275                 280                 285

Ser Ala Leu Glu Glu Tyr Thr Lys Lys Leu Asn Thr Gln
290                 295                 300

<210> SEQ ID NO 6
<211> LENGTH: 304
<212> TYPE: PRT
<213> ORGANISM: Homo sapiens
<220> FEATURE:
<221> NAME/KEY: misc_feature
<222> LOCATION: (1)..(58)
<223> OTHER INFORMATION: Trimerisation module from tetranectin
<221> NAME/KEY: misc_feature
<222> LOCATION: (59)..(61)
<223> OTHER INFORMATION: Linker
<221> NAME/KEY: misc_feature
<222> LOCATION: (62)..(304)
<223> OTHER INFORMATION: Mature Apo A1

<400> SEQUENCE: 6

Ser Pro Gly Thr Glu Pro Pro Thr Gln Lys Pro Lys Lys Ile Val Asn
1               5                   10                  15
```

```
Ala Lys Lys Asp Val Val Asn Thr Lys Met Phe Glu Glu Leu Lys Ser
            20                  25                  30

Arg Leu Asp Thr Leu Ala Gln Glu Val Ala Leu Leu Lys Glu Gln Gln
        35                  40                  45

Ala Leu Gln Thr Val Ser Leu Lys Gly Ser Ser Gly His Asp Glu Pro
    50                  55                  60

Pro Gln Ser Pro Trp Asp Arg Val Lys Asp Leu Ala Thr Val Tyr Val
65                  70                  75                  80

Asp Val Leu Lys Asp Ser Gly Arg Asp Tyr Val Ser Gln Phe Glu Gly
                85                  90                  95

Ser Ala Leu Gly Lys Gln Leu Asn Leu Lys Leu Leu Asp Asn Trp Asp
            100                 105                 110

Ser Val Thr Ser Thr Phe Ser Lys Leu Arg Glu Gln Leu Gly Pro Val
            115                 120                 125

Thr Gln Glu Phe Trp Asp Asn Leu Glu Lys Glu Thr Glu Gly Leu Arg
        130                 135                 140

Gln Glu Met Ser Lys Asp Leu Glu Glu Val Lys Ala Lys Val Gln Pro
145                 150                 155                 160

Tyr Leu Asp Asp Phe Gln Lys Lys Trp Gln Glu Glu Met Glu Leu Tyr
                165                 170                 175

Arg Gln Lys Val Glu Pro Leu Arg Ala Glu Leu Gln Glu Gly Ala Arg
            180                 185                 190

Gln Lys Leu His Glu Leu Gln Glu Lys Leu Ser Pro Leu Gly Glu Glu
        195                 200                 205

Met Arg Asp Arg Ala Arg Ala His Val Asp Ala Leu Arg Thr His Leu
    210                 215                 220

Ala Pro Tyr Ser Asp Glu Leu Arg Gln Arg Leu Ala Ala Arg Leu Glu
225                 230                 235                 240

Ala Leu Lys Glu Asn Gly Gly Ala Arg Leu Ala Glu Tyr His Ala Lys
                245                 250                 255

Ala Thr Glu His Leu Ser Thr Leu Ser Glu Lys Ala Lys Pro Ala Leu
            260                 265                 270

Glu Asp Leu Arg Gln Gly Leu Leu Pro Val Leu Glu Ser Phe Lys Val
        275                 280                 285

Ser Phe Leu Ser Ala Leu Glu Glu Tyr Thr Lys Lys Leu Asn Thr Gln
    290                 295                 300

<210> SEQ ID NO 7
<211> LENGTH: 304
<212> TYPE: PRT
<213> ORGANISM: Homo sapiens
<220> FEATURE:
<221> NAME/KEY: misc_feature
<222> LOCATION: (1)..(56)
<223> OTHER INFORMATION: Trimerisation module from tetranectin
<221> NAME/KEY: misc_feature
<222> LOCATION: (57)..(61)
<223> OTHER INFORMATION: Fibronectin based linker
<221> NAME/KEY: misc_feature
<222> LOCATION: (62)..(304)
<223> OTHER INFORMATION: Mature Apo A1

<400> SEQUENCE: 7

Ser Pro Gly Thr Glu Pro Pro Thr Gln Lys Pro Lys Lys Ile Val Asn
1               5                   10                  15

Ala Lys Lys Asp Val Val Asn Thr Lys Met Phe Glu Glu Leu Lys Ser
            20                  25                  30
```

Arg Leu Asp Thr Leu Ala Gln Glu Val Ala Leu Leu Lys Glu Gln Gln
              35                  40                  45

Ala Leu Gln Thr Val Ser Leu Lys Gly Thr Ser Gly Gln Asp Glu Pro
         50                  55                  60

Pro Gln Ser Pro Trp Asp Arg Val Lys Asp Leu Ala Thr Val Tyr Val
 65                  70                  75                  80

Asp Val Leu Lys Asp Ser Gly Arg Asp Tyr Val Ser Gln Phe Glu Gly
                 85                  90                  95

Ser Ala Leu Gly Lys Gln Leu Asn Leu Lys Leu Leu Asp Asn Trp Asp
             100                 105                 110

Ser Val Thr Ser Thr Phe Ser Lys Leu Arg Glu Gln Leu Gly Pro Val
         115                 120                 125

Thr Gln Glu Phe Trp Asp Asn Leu Glu Lys Glu Thr Glu Gly Leu Arg
 130                 135                 140

Gln Glu Met Ser Lys Asp Leu Glu Glu Val Lys Ala Lys Val Gln Pro
145                 150                 155                 160

Tyr Leu Asp Asp Phe Gln Lys Lys Trp Gln Glu Met Glu Leu Tyr
                 165                 170                 175

Arg Gln Lys Val Glu Pro Leu Arg Ala Glu Leu Gln Glu Gly Ala Arg
             180                 185                 190

Gln Lys Leu His Glu Leu Gln Glu Lys Leu Ser Pro Leu Gly Glu Glu
         195                 200                 205

Met Arg Asp Arg Ala Arg Ala His Val Asp Ala Leu Arg Thr His Leu
 210                 215                 220

Ala Pro Tyr Ser Asp Glu Leu Arg Gln Arg Leu Ala Ala Arg Leu Glu
225                 230                 235                 240

Ala Leu Lys Glu Asn Gly Gly Ala Arg Leu Ala Glu Tyr His Ala Lys
                 245                 250                 255

Ala Thr Glu His Leu Ser Thr Leu Ser Glu Lys Ala Lys Pro Ala Leu
             260                 265                 270

Glu Asp Leu Arg Gln Gly Leu Leu Pro Val Leu Glu Ser Phe Lys Val
         275                 280                 285

Ser Phe Leu Ser Ala Leu Glu Glu Tyr Thr Lys Lys Leu Asn Thr Gln
 290                 295                 300

<210> SEQ ID NO 8
<211> LENGTH: 304
<212> TYPE: PRT
<213> ORGANISM: Homo sapiens
<220> FEATURE:
<221> NAME/KEY: misc_feature
<222> LOCATION: (1)..(56)
<223> OTHER INFORMATION: Trimerisation module from tetranectin
<221> NAME/KEY: misc_feature
<222> LOCATION: (13)..(13)
<223> OTHER INFORMATION: Mutagen
<221> NAME/KEY: misc_feature
<222> LOCATION: (19)..(19)
<223> OTHER INFORMATION: Mutagen
<221> NAME/KEY: misc_feature
<222> LOCATION: (62)..(304)
<223> OTHER INFORMATION: Mature Apo A1

<400> SEQUENCE: 8

Ser Pro Gly Thr Glu Pro Pro Thr Gln Lys Pro Lys Ala Ile Val Asn
 1               5                  10                  15

Ala Lys Ala Asp Val Val Asn Thr Lys Met Phe Glu Glu Leu Lys Ser
             20                  25                  30

```
Arg Leu Asp Thr Leu Ala Gln Glu Val Ala Leu Leu Lys Glu Gln Gln
         35                  40                  45

Ala Leu Gln Thr Val Ser Leu Lys Gly Thr Ser Gly Gln Asp Glu Pro
     50                  55                  60

Pro Gln Ser Pro Trp Asp Arg Val Lys Asp Leu Ala Thr Val Tyr Val
65                  70                  75                  80

Asp Val Leu Lys Asp Ser Gly Arg Asp Tyr Val Ser Gln Phe Glu Gly
                 85                  90                  95

Ser Ala Leu Gly Lys Gln Leu Asn Leu Lys Leu Leu Asp Asn Trp Asp
             100                 105                 110

Ser Val Thr Ser Thr Phe Ser Lys Leu Arg Glu Gln Leu Gly Pro Val
         115                 120                 125

Thr Gln Glu Phe Trp Asp Asn Leu Glu Lys Glu Thr Glu Gly Leu Arg
     130                 135                 140

Gln Glu Met Ser Lys Asp Leu Glu Glu Val Lys Ala Lys Val Gln Pro
145                 150                 155                 160

Tyr Leu Asp Asp Phe Gln Lys Lys Trp Gln Glu Glu Met Glu Leu Tyr
                 165                 170                 175

Arg Gln Lys Val Glu Pro Leu Arg Ala Glu Leu Gln Glu Gly Ala Arg
             180                 185                 190

Gln Lys Leu His Glu Leu Gln Glu Lys Leu Ser Pro Leu Gly Glu Glu
         195                 200                 205

Met Arg Asp Arg Ala Arg Ala His Val Asp Ala Leu Arg Thr His Leu
     210                 215                 220

Ala Pro Tyr Ser Asp Glu Leu Arg Gln Arg Leu Ala Ala Arg Leu Glu
225                 230                 235                 240

Ala Leu Lys Glu Asn Gly Gly Ala Arg Leu Ala Glu Tyr His Ala Lys
                 245                 250                 255

Ala Thr Glu His Leu Ser Thr Leu Ser Glu Lys Ala Lys Pro Ala Leu
             260                 265                 270

Glu Asp Leu Arg Gln Gly Leu Leu Pro Val Leu Glu Ser Phe Lys Val
         275                 280                 285

Ser Phe Leu Ser Ala Leu Glu Glu Tyr Thr Lys Lys Leu Asn Thr Gln
     290                 295                 300

<210> SEQ ID NO 9
<211> LENGTH: 306
<212> TYPE: PRT
<213> ORGANISM: Homo sapiens
<220> FEATURE:
<221> NAME/KEY: misc_feature
<222> LOCATION: (1)..(58)
<223> OTHER INFORMATION: Trimerisation module from tetranectin
<221> NAME/KEY: misc_feature
<222> LOCATION: (59)..(63)
<223> OTHER INFORMATION: Linker
<221> NAME/KEY: misc_feature
<222> LOCATION: (64)..(306)
<223> OTHER INFORMATION: Mature Apo A1

<400> SEQUENCE: 9

Ser Pro Gly Thr Glu Pro Pro Thr Gln Lys Pro Lys Lys Ile Val Asn
1               5                   10                  15

Ala Lys Lys Asp Val Val Asn Thr Lys Met Phe Glu Glu Leu Lys Ser
             20                  25                  30

Arg Leu Asp Thr Leu Ala Gln Glu Val Ala Leu Leu Lys Glu Gln Gln
         35                  40                  45
```

```
Ala Leu Gln Thr Val Ser Leu Lys Gly Ser Lys Val His Met Lys Asp
             50                  55                  60

Glu Pro Pro Gln Ser Pro Trp Asp Arg Val Lys Asp Leu Ala Thr Val
 65                  70                  75                  80

Tyr Val Asp Val Leu Lys Asp Ser Gly Arg Asp Tyr Val Ser Gln Phe
                 85                  90                  95

Glu Gly Ser Ala Leu Gly Lys Gln Leu Asn Leu Lys Leu Leu Asp Asn
                100                 105                 110

Trp Asp Ser Val Thr Ser Thr Phe Ser Lys Leu Arg Glu Gln Leu Gly
            115                 120                 125

Pro Val Thr Gln Glu Phe Trp Asp Asn Leu Glu Lys Glu Thr Glu Gly
130                 135                 140

Leu Arg Gln Glu Met Ser Lys Asp Leu Glu Glu Val Lys Ala Lys Val
145                 150                 155                 160

Gln Pro Tyr Leu Asp Asp Phe Gln Lys Lys Trp Gln Glu Glu Met Glu
                165                 170                 175

Leu Tyr Arg Gln Lys Val Glu Pro Leu Arg Ala Glu Leu Gln Glu Gly
                180                 185                 190

Ala Arg Gln Lys Leu His Glu Leu Gln Glu Lys Leu Ser Pro Leu Gly
            195                 200                 205

Glu Glu Met Arg Asp Arg Ala Arg Ala His Val Asp Ala Leu Arg Thr
210                 215                 220

His Leu Ala Pro Tyr Ser Asp Glu Leu Arg Gln Arg Leu Ala Ala Arg
225                 230                 235                 240

Leu Glu Ala Leu Lys Glu Asn Gly Gly Ala Arg Leu Ala Glu Tyr His
                245                 250                 255

Ala Lys Ala Thr Glu His Leu Ser Thr Leu Ser Glu Lys Ala Lys Pro
            260                 265                 270

Ala Leu Glu Asp Leu Arg Gln Gly Leu Leu Pro Val Leu Glu Ser Phe
        275                 280                 285

Lys Val Ser Phe Leu Ser Ala Leu Glu Glu Tyr Thr Lys Lys Leu Asn
    290                 295                 300

Thr Gln
305

<210> SEQ ID NO 10
<211> LENGTH: 306
<212> TYPE: PRT
<213> ORGANISM: Homo sapiens
<220> FEATURE:
<221> NAME/KEY: misc_feature
<222> LOCATION: (1)..(56)
<223> OTHER INFORMATION: Trimerisation module from tetranectin
<221> NAME/KEY: misc_feature
<222> LOCATION: (57)..(63)
<223> OTHER INFORMATION: Tetranectin based linker
<221> NAME/KEY: misc_feature
<222> LOCATION: (64)..(306)
<223> OTHER INFORMATION: Mature Apo A1

<400> SEQUENCE: 10

Ser Pro Gly Thr Glu Pro Pro Thr Gln Lys Pro Lys Lys Ile Val Asn
 1               5                  10                  15

Ala Lys Lys Asp Val Val Asn Thr Lys Met Phe Glu Glu Leu Lys Ser
            20                  25                  30

Arg Leu Asp Thr Leu Ala Gln Glu Val Ala Leu Leu Lys Glu Gln Gln
        35                  40                  45
```

```
Ala Leu Gln Thr Val Ser Leu Lys Gly Thr Lys Val His Met Lys Asp
        50                  55                  60

Glu Pro Pro Gln Ser Pro Trp Asp Arg Val Lys Asp Leu Ala Thr Val
 65                  70                  75                  80

Tyr Val Asp Val Leu Lys Asp Ser Gly Arg Asp Tyr Val Ser Gln Phe
                85                  90                  95

Glu Gly Ser Ala Leu Gly Lys Gln Leu Asn Leu Lys Leu Leu Asp Asn
            100                 105                 110

Trp Asp Ser Val Thr Ser Thr Phe Ser Lys Leu Arg Glu Gln Leu Gly
            115                 120                 125

Pro Val Thr Gln Glu Phe Trp Asp Asn Leu Glu Lys Glu Thr Glu Gly
130                 135                 140

Leu Arg Gln Glu Met Ser Lys Asp Leu Glu Glu Val Lys Ala Lys Val
145                 150                 155                 160

Gln Pro Tyr Leu Asp Asp Phe Gln Lys Lys Trp Gln Glu Glu Met Glu
                165                 170                 175

Leu Tyr Arg Gln Lys Val Glu Pro Leu Arg Ala Glu Leu Gln Glu Gly
                180                 185                 190

Ala Arg Gln Lys Leu His Glu Leu Gln Glu Lys Leu Ser Pro Leu Gly
            195                 200                 205

Glu Glu Met Arg Asp Arg Ala Arg Ala His Val Asp Ala Leu Arg Thr
210                 215                 220

His Leu Ala Pro Tyr Ser Asp Glu Leu Arg Gln Arg Leu Ala Ala Arg
225                 230                 235                 240

Leu Glu Ala Leu Lys Glu Asn Gly Gly Ala Arg Leu Ala Glu Tyr His
                245                 250                 255

Ala Lys Ala Thr Glu His Leu Ser Thr Leu Ser Glu Lys Ala Lys Pro
            260                 265                 270

Ala Leu Glu Asp Leu Arg Gln Gly Leu Leu Pro Val Leu Glu Ser Phe
            275                 280                 285

Lys Val Ser Phe Leu Ser Ala Leu Glu Glu Tyr Thr Lys Lys Leu Asn
        290                 295                 300

Thr Gln
305

<210> SEQ ID NO 11
<211> LENGTH: 306
<212> TYPE: PRT
<213> ORGANISM: Homo sapiens
<220> FEATURE:
<221> NAME/KEY: misc_feature
<222> LOCATION: (1)..(56)
<223> OTHER INFORMATION: Trimerisation module from tetranectin
<221> NAME/KEY: misc_feature
<222> LOCATION: (13)..(13)
<223> OTHER INFORMATION: Mutagen
<221> NAME/KEY: misc_feature
<222> LOCATION: (19)..(19)
<223> OTHER INFORMATION: Mutagen
<221> NAME/KEY: misc_feature
<222> LOCATION: (57)..(63)
<223> OTHER INFORMATION: Tetranectin based linker
<221> NAME/KEY: misc_feature
<222> LOCATION: (64)..(306)
<223> OTHER INFORMATION: Mature Apo A1

<400> SEQUENCE: 11

Ser Pro Gly Thr Glu Pro Pro Thr Gln Lys Pro Lys Ala Ile Val Asn
 1               5                  10                  15
```

```
Ala Lys Ala Asp Val Val Asn Thr Lys Met Phe Glu Glu Leu Lys Ser
         20                  25                  30
Arg Leu Asp Thr Leu Ala Gln Glu Val Ala Leu Leu Lys Glu Gln Gln
     35                  40                  45
Ala Leu Gln Thr Val Ser Leu Lys Gly Thr Lys Val His Met Lys Asp
 50                  55                  60
Glu Pro Pro Gln Ser Pro Trp Asp Arg Val Lys Asp Leu Ala Thr Val
65                  70                  75                  80
Tyr Val Asp Val Leu Lys Asp Ser Gly Arg Asp Tyr Val Ser Gln Phe
                 85                  90                  95
Glu Gly Ser Ala Leu Gly Lys Gln Leu Asn Leu Lys Leu Leu Asp Asn
            100                 105                 110
Trp Asp Ser Val Thr Ser Thr Phe Ser Lys Leu Arg Glu Gln Leu Gly
        115                 120                 125
Pro Val Thr Gln Glu Phe Trp Asp Asn Leu Glu Lys Glu Thr Glu Gly
130                 135                 140
Leu Arg Gln Glu Met Ser Lys Asp Leu Glu Glu Val Lys Ala Lys Val
145                 150                 155                 160
Gln Pro Tyr Leu Asp Asp Phe Gln Lys Lys Trp Gln Glu Glu Met Glu
                165                 170                 175
Leu Tyr Arg Gln Lys Val Glu Pro Leu Arg Ala Glu Leu Gln Glu Gly
            180                 185                 190
Ala Arg Gln Lys Leu His Glu Leu Gln Glu Lys Leu Ser Pro Leu Gly
        195                 200                 205
Glu Glu Met Arg Asp Arg Ala Arg Ala His Val Asp Ala Leu Arg Thr
210                 215                 220
His Leu Ala Pro Tyr Ser Asp Glu Leu Arg Gln Arg Leu Ala Ala Arg
225                 230                 235                 240
Leu Glu Ala Leu Lys Glu Asn Gly Gly Ala Arg Leu Ala Glu Tyr His
                245                 250                 255
Ala Lys Ala Thr Glu His Leu Ser Thr Leu Ser Glu Lys Ala Lys Pro
            260                 265                 270
Ala Leu Glu Asp Leu Arg Gln Gly Leu Leu Pro Val Leu Glu Ser Phe
        275                 280                 285
Lys Val Ser Phe Leu Ser Ala Leu Glu Glu Tyr Thr Lys Lys Leu Asn
290                 295                 300
Thr Gln
305

<210> SEQ ID NO 12
<211> LENGTH: 51
<212> TYPE: PRT
<213> ORGANISM: Homo sapiens

<400> SEQUENCE: 12

Glu Pro Pro Thr Gln Lys Pro Lys Lys Ile Val Asn Ala Lys Lys Asp
1               5                   10                  15
Val Val Asn Thr Lys Met Phe Glu Glu Leu Lys Ser Arg Leu Asp Thr
            20                  25                  30
Leu Ala Gln Glu Val Ala Leu Leu Lys Glu Gln Gln Ala Leu Gln Thr
        35                  40                  45
Val Cys Leu
 50
```

-continued

```
<210> SEQ ID NO 13
<211> LENGTH: 58
<212> TYPE: PRT
<213> ORGANISM: Homo sapiens
<220> FEATURE:
<221> NAME/KEY: misc_feature
<222> LOCATION: (1)..(4)
<223> OTHER INFORMATION: Linker sequence
<221> NAME/KEY: misc_feature
<222> LOCATION: (5)..(56)
<223> OTHER INFORMATION: Modified TTSE
<221> NAME/KEY: misc_feature
<222> LOCATION: (57)..(58)
<223> OTHER INFORMATION: Linker

<400> SEQUENCE: 13

Ser Pro Gly Thr Glu Pro Pro Thr Gln Lys Pro Lys Lys Ile Val Asn
1               5                   10                  15

Ala Lys Lys Asp Val Val Asn Thr Lys Met Phe Glu Glu Leu Lys Ser
            20                  25                  30

Arg Leu Asp Thr Leu Ala Gln Val Ala Leu Leu Lys Glu Gln Gln
        35                  40                  45

Ala Leu Gln Thr Val Ser Leu Lys Gly Ser
    50                  55

<210> SEQ ID NO 14
<211> LENGTH: 329
<212> TYPE: PRT
<213> ORGANISM: Homo sapiens
<220> FEATURE:
<221> NAME/KEY: misc_feature
<222> LOCATION: (1)..(86)
<223> OTHER INFORMATION: Hp(alpha) residues
<221> NAME/KEY: misc_feature
<222> LOCATION: (87)..(329)
<223> OTHER INFORMATION: Apo A1

<400> SEQUENCE: 14

Gly Val Asp Ser Gly Asn Asp Val Thr Asp Ile Ala Asp Asp Gly Cys
1               5                   10                  15

Pro Lys Pro Pro Glu Ile Ala His Gly Tyr Val Glu His Ser Val Arg
            20                  25                  30

Tyr Gln Cys Lys Asn Tyr Tyr Lys Leu Arg Thr Glu Gly Asp Gly Val
        35                  40                  45

Tyr Thr Leu Asn Asn Glu Lys Gln Trp Ile Asn Lys Ala Val Gly Asp
    50                  55                  60

Lys Leu Pro Glu Cys Glu Ala Val Ala Gly Lys Pro Lys Asn Pro Ala
65                  70                  75                  80

Asn Pro Val Gln Arg Ser Asp Glu Pro Pro Gln Ser Pro Trp Asp Arg
                85                  90                  95

Val Lys Asp Leu Ala Thr Val Tyr Val Asp Val Leu Lys Asp Ser Gly
            100                 105                 110

Arg Asp Tyr Val Ser Gln Phe Glu Gly Ser Ala Leu Gly Lys Gln Leu
        115                 120                 125

Asn Leu Lys Leu Leu Asp Asn Trp Asp Ser Val Thr Ser Thr Phe Ser
    130                 135                 140

Lys Leu Arg Glu Gln Leu Gly Pro Val Thr Gln Glu Phe Trp Asp Asn
145                 150                 155                 160

Leu Glu Lys Glu Thr Glu Gly Leu Arg Gln Glu Met Ser Lys Asp Leu
                165                 170                 175

Glu Glu Val Lys Ala Lys Val Gln Pro Tyr Leu Asp Asp Phe Gln Lys
            180                 185                 190
```

```
Lys Trp Gln Glu Glu Met Glu Leu Tyr Arg Gln Lys Val Glu Pro Leu
            195                 200                 205

Arg Ala Glu Leu Gln Glu Gly Ala Arg Gln Lys Leu His Glu Leu Gln
210                 215                 220

Glu Lys Leu Ser Pro Leu Gly Glu Glu Met Arg Asp Arg Ala Arg Ala
225                 230                 235                 240

His Val Asp Ala Leu Arg Thr His Leu Ala Pro Tyr Ser Asp Glu Leu
                245                 250                 255

Arg Gln Arg Leu Ala Ala Arg Leu Glu Ala Leu Lys Glu Asn Gly Gly
            260                 265                 270

Ala Arg Leu Ala Glu Tyr His Ala Lys Ala Thr Glu His Leu Ser Thr
        275                 280                 285

Leu Ser Glu Lys Ala Lys Pro Ala Leu Glu Asp Leu Arg Gln Gly Leu
290                 295                 300

Leu Pro Val Leu Glu Ser Phe Lys Val Ser Phe Leu Ser Ala Leu Glu
305                 310                 315                 320

Glu Tyr Thr Lys Lys Leu Asn Thr Gln
                325

<210> SEQ ID NO 15
<211> LENGTH: 267
<212> TYPE: PRT
<213> ORGANISM: Homo sapiens

<400> SEQUENCE: 15

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240
```

```
Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 16
<211> LENGTH: 267
<212> TYPE: PRT
<213> ORGANISM: Macaca fascicularis

<400> SEQUENCE: 16

Met Lys Ala Thr Val Leu Thr Leu Ala Val Leu Phe Leu Thr Gly Ser
1               5                   10                  15

Gln Ala Arg His Phe Trp Gln Gln Asp Glu Pro Pro Gln Thr Pro Trp
            20                  25                  30

Asp Arg Val Lys Asp Leu Val Thr Val Tyr Val Glu Ala Leu Lys Asp
        35                  40                  45

Ser Gly Lys Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Val Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu His Glu Gly Thr Arg Gln Lys Leu His Glu
145                 150                 155                 160

Leu His Glu Lys Leu Ser Pro Leu Gly Glu Glu Val Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Ser Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Ser Thr Gln
            260                 265

<210> SEQ ID NO 17
<211> LENGTH: 265
<212> TYPE: PRT
<213> ORGANISM: Bos Taurus

<400> SEQUENCE: 17

Met Lys Ala Val Val Leu Thr Leu Ala Val Leu Phe Leu Thr Gly Ser
1               5                   10                  15

Gln Ala Arg His Phe Trp Gln Gln Asp Asp Pro Gln Ser Ser Trp Asp
            20                  25                  30
```

```
Arg Val Lys Asp Phe Ala Thr Val Tyr Val Glu Ala Ile Lys Asp Ser
        35                  40                  45

Gly Arg Asp Tyr Val Ala Gln Phe Glu Ala Ser Ala Leu Gly Lys Gln
    50                  55                  60

Leu Asn Leu Lys Leu Leu Asp Asn Trp Asp Thr Leu Ala Ser Thr Leu
65                  70                  75                  80

Ser Lys Val Arg Glu Gln Leu Gly Pro Val Thr Gln Glu Phe Trp Asp
                85                  90                  95

Asn Leu Glu Lys Glu Thr Ala Ser Leu Arg Gln Glu Met His Lys Asp
            100                 105                 110

Leu Glu Glu Val Lys Gln Lys Val Gln Pro Tyr Leu Asp Glu Phe Gln
        115                 120                 125

Lys Lys Trp His Glu Glu Val Glu Ile Tyr Arg Gln Lys Val Ala Pro
130                 135                 140

Leu Gly Glu Glu Phe Arg Glu Gly Ala Arg Gln Lys Val Gln Glu Leu
145                 150                 155                 160

Gln Asp Lys Leu Ser Pro Leu Ala Gln Glu Leu Arg Asp Arg Ala Arg
                165                 170                 175

Ala His Val Glu Thr Leu Arg Gln Gln Leu Ala Pro Tyr Ser Asp Asp
            180                 185                 190

Leu Arg Gln Arg Leu Thr Ala Arg Leu Glu Ala Leu Lys Glu Gly Gly
        195                 200                 205

Gly Ser Leu Ala Glu Tyr His Ala Lys Ala Ser Glu Gln Leu Lys Ala
    210                 215                 220

Leu Gly Glu Lys Ala Lys Pro Val Leu Glu Asp Leu Arg Gln Gly Leu
225                 230                 235                 240

Leu Pro Val Leu Glu Ser Leu Lys Val Ser Ile Leu Ala Ala Ile Asp
                245                 250                 255

Glu Ala Ser Lys Lys Leu Asn Ala Gln
            260                 265

<210> SEQ ID NO 18
<211> LENGTH: 265
<212> TYPE: PRT
<213> ORGANISM: Sus scrofa

<400> SEQUENCE: 18

Met Lys Ala Val Val Leu Thr Leu Ala Val Leu Phe Leu Thr Gly Ser
1               5                   10                  15

Gln Ala Arg His Phe Trp Gln Gln Asp Pro Gln Ser Pro Trp Asp
        20                  25                  30

Arg Val Lys Asp Phe Ala Thr Val Tyr Val Asp Ala Ile Lys Asp Ser
        35                  40                  45

Gly Arg Asp Tyr Val Ala Gln Phe Glu Ala Ser Ala Leu Gly Lys His
    50                  55                  60

Leu Asn Leu Lys Leu Leu Asp Asn Trp Asp Ser Leu Gly Ser Thr Phe
65                  70                  75                  80

Thr Lys Val Arg Glu Gln Leu Gly Pro Val Thr Gln Glu Phe Trp Asp
                85                  90                  95

Asn Leu Glu Lys Glu Thr Glu Ala Leu Arg Gln Glu Met Ser Lys Asp
            100                 105                 110

Leu Glu Glu Val Lys Lys Val Gln Pro Tyr Leu Asp Asp Phe Gln
        115                 120                 125

Asn Lys Trp Gln Glu Glu Met Glu Thr Tyr Arg Gln Lys Met Ala Pro
130                 135                 140
```

```
Leu Gly Ala Glu Phe Arg Gly Ala Arg Gln Lys Val Gln Glu Leu
145                 150                 155                 160

Gln Glu Lys Leu Ser Pro Leu Ala Glu Leu Arg Asp Arg Leu Arg
                165                 170                 175

Ala His Val Glu Ala Leu Arg Gln His Val Ala Pro Tyr Ser Asp Asp
            180                 185                 190

Leu Arg Gln Arg Met Ala Ala Arg Phe Glu Ala Leu Lys Glu Gly Gly
        195                 200                 205

Gly Ser Leu Ala Glu Tyr Gln Ala Lys Ala Gln Glu Gln Leu Lys Ala
        210                 215                 220

Leu Gly Glu Lys Ala Lys Pro Ala Leu Glu Asp Leu Arg Gln Gly Leu
225                 230                 235                 240

Leu Pro Val Leu Glu Asn Leu Lys Val Ser Ile Leu Ala Ala Ile Asp
                245                 250                 255

Glu Ala Ser Lys Lys Leu Asn Ala Gln
                260                 265
```

<210> SEQ ID NO 19
<211> LENGTH: 266
<212> TYPE: PRT
<213> ORGANISM: Canis familiaris

<400> SEQUENCE: 19

```
Met Lys Ala Ala Leu Leu Thr Leu Ala Val Leu Phe Leu Thr Gly Ser
1               5                   10                  15

Gln Ala Arg His Phe Trp Gln Gln Asp Glu Pro Gln Ser Pro Trp Asp
            20                  25                  30

Arg Val Lys Asp Leu Ala Thr Val Tyr Val Asp Ala Val Lys Asp Ser
        35                  40                  45

Gly Arg Asp Tyr Val Ala Gln Phe Glu Ala Ser Ala Leu Gly Lys Gln
    50                  55                  60

Leu Asn Leu Lys Leu Leu Asp Asn Trp Asp Ser Leu Ser Ser Thr Val
65                  70                  75                  80

Thr Lys Leu Arg Glu Gln Ile Gly Pro Val Thr Gln Glu Phe Trp Asp
                85                  90                  95

Asn Leu Glu Lys Glu Thr Glu Val Leu Arg Gln Glu Met Ser Lys Asp
            100                 105                 110

Leu Glu Glu Val Lys Gln Lys Val Gln Pro Tyr Leu Asp Asp Phe Gln
        115                 120                 125

Lys Lys Trp Gln Glu Glu Val Glu Leu Tyr Arg Gln Lys Val Ala Pro
130                 135                 140

Leu Gly Ser Glu Leu Arg Glu Gly Ala Arg Gln Lys Leu Gln Glu Leu
145                 150                 155                 160

Gln Glu Lys Leu Ser Pro Leu Ala Glu Glu Leu Arg Asp Arg Ala Arg
                165                 170                 175

Thr His Val Asp Ala Leu Arg Ala Gln Leu Ala Pro Tyr Ser Asp Asp
            180                 185                 190

Leu Arg Glu Arg Leu Ala Ala Arg Leu Glu Ala Leu Lys Glu Gly Gly
        195                 200                 205

Gly Ala Ser Leu Ala Glu Tyr His Ala Arg Ala Ser Glu Gln Leu Ser
    210                 215                 220

Ala Leu Gly Glu Lys Ala Arg Pro Ala Leu Glu Asp Leu Arg Gln Gly
225                 230                 235                 240
```

```
Leu Leu Pro Val Leu Glu Ser Phe Lys Val Ser Leu Leu Ala Ala Ile
                245                 250                 255

Asp Glu Ala Thr Lys Lys Leu Asn Ala Gln
            260                 265

<210> SEQ ID NO 20
<211> LENGTH: 266
<212> TYPE: PRT
<213> ORGANISM: Oryctolagus cuniculus

<400> SEQUENCE: 20

Met Lys Ala Val Val Leu Thr Leu Ala Val Leu Phe Leu Thr Gly Ser
1               5                   10                  15

Gln Ala Arg His Phe Trp Gln Arg Asp Glu Pro Arg Ser Ser Trp Asp
            20                  25                  30

Lys Ile Lys Asp Phe Ala Thr Val Tyr Val Asp Thr Val Lys Asp Ser
        35                  40                  45

Gly Arg Glu Tyr Val Ala Gln Phe Glu Ala Ser Ala Phe Gly Lys Gln
    50                  55                  60

Leu Asn Leu Lys Leu Leu Asp Asn Trp Asp Ser Leu Ser Ser Thr Val
65                  70                  75                  80

Ser Lys Leu Gln Glu Gln Leu Gly Pro Val Thr Gln Glu Phe Trp Asp
                85                  90                  95

Asn Leu Glu Lys Glu Thr Glu Gly Leu Arg Glu Glu Met Asn Lys Asp
            100                 105                 110

Leu Gln Glu Val Arg Gln Lys Val Gln Pro Tyr Leu Asp Glu Phe Gln
        115                 120                 125

Lys Lys Trp Gln Glu Glu Val Glu Arg Tyr Arg Gln Lys Val Glu Pro
    130                 135                 140

Leu Gly Ala Glu Leu Arg Glu Ser Ala Arg Gln Lys Leu Thr Glu Leu
145                 150                 155                 160

Gln Glu Lys Leu Ser Pro Leu Ala Glu Glu Leu Arg Asp Ser Ala Arg
                165                 170                 175

Thr His Val Asp Thr Leu Arg Thr Lys Leu Ala Pro Tyr Ser Asn Glu
            180                 185                 190

Leu Gln Gln Arg Leu Ala Ala Arg Leu Glu Ser Ile Lys Glu Gly Gly
        195                 200                 205

Gly Ala Ser Leu Ala Glu Tyr Gln Ala Lys Ala Arg Glu His Leu Ser
    210                 215                 220

Val Leu Ser Glu Lys Ala Arg Pro Ala Leu Glu Asp Leu Arg Gln Gly
225                 230                 235                 240

Leu Leu Pro Val Leu Glu Ser Phe Lys Ala Ser Val Gln Asn Val Leu
                245                 250                 255

Asp Glu Ala Thr Lys Lys Leu Asn Thr Gln
            260                 265

<210> SEQ ID NO 21
<211> LENGTH: 265
<212> TYPE: PRT
<213> ORGANISM: Tupaia glis belangeri

<400> SEQUENCE: 21

Met Lys Ala Val Val Leu Thr Leu Ala Val Leu Phe Leu Thr Gly Ser
1               5                   10                  15

Gln Ala Arg His Phe Trp Gln Gln Asp Glu Pro Gln Ser Ser Trp Asp
            20                  25                  30
```

```
Arg Val Arg Asp Leu Ala Asn Val Tyr Val Asp Ala Val Lys Glu Ser
        35                  40                  45

Gly Arg Glu Tyr Val Ser Gln Leu Glu Ala Ser Ala Leu Gly Lys Gln
 50                  55                  60

Leu Asn Leu Lys Leu Val Asp Asn Trp Asp Thr Leu Gly Ser Thr Phe
 65                  70                  75                  80

Gln Lys Val His Glu His Leu Gly Pro Val Ala Gln Glu Phe Trp Glu
                 85                  90                  95

Lys Leu Glu Lys Glu Thr Glu Leu Arg Arg Glu Ile Asn Lys Asp
            100                 105                 110

Leu Glu Asp Val Arg Gln Lys Thr Gln Pro Phe Leu Asp Glu Ile Gln
            115                 120                 125

Lys Lys Trp Gln Glu Asp Leu Glu Arg Tyr Arg Gln Lys Val Glu Pro
130                 135                 140

Leu Ser Ala Gln Leu Arg Glu Gly Ala Arg Gln Lys Leu Met Glu Leu
145                 150                 155                 160

Gln Glu Gln Val Thr Pro Leu Gly Glu Asp Leu Arg Asp Ser Val Arg
                165                 170                 175

Ala Tyr Ala Asp Thr Leu Arg Thr Gln Leu Ala Pro Tyr Ser Glu Gln
            180                 185                 190

Met Arg Lys Thr Leu Gly Ala Arg Leu Glu Ala Ile Lys Glu Gly Gly
            195                 200                 205

Ser Ala Ser Leu Ala Glu Tyr His Ala Lys Ala Ser Glu Gln Leu Ser
            210                 215                 220

Ala Leu Gly Glu Lys Ala Lys Pro Val Leu Glu Asp Ile His Gln Gly
225                 230                 235                 240

Leu Met Pro Met Trp Glu Ser Phe Lys Thr Gly Val Leu Asn Val Ile
                245                 250                 255

Asp Glu Ala Ala Lys Lys Leu Thr Ala
            260                 265

<210> SEQ ID NO 22
<211> LENGTH: 264
<212> TYPE: PRT
<213> ORGANISM: Mus musculus

<400> SEQUENCE: 22

Met Lys Ala Val Val Leu Ala Val Ala Leu Val Phe Leu Thr Gly Ser
 1               5                  10                  15

Gln Ala Trp His Val Trp Gln Gln Asp Glu Pro Gln Ser Gln Trp Asp
                 20                  25                  30

Lys Val Lys Asp Phe Ala Asn Val Tyr Val Asp Ala Val Lys Asp Ser
            35                  40                  45

Gly Arg Asp Tyr Val Ser Gln Phe Glu Ser Ser Leu Gly Gln Gln
 50                  55                  60

Leu Asn Leu Asn Leu Leu Glu Asn Trp Asp Thr Leu Gly Ser Thr Val
 65                  70                  75                  80

Ser Gln Leu Gln Glu Arg Leu Gly Pro Leu Thr Arg Asp Phe Trp Asp
                 85                  90                  95

Asn Leu Glu Lys Glu Thr Asp Trp Val Arg Gln Glu Met Asn Lys Asp
            100                 105                 110

Leu Glu Glu Val Lys Gln Lys Val Gln Pro Tyr Leu Asp Glu Phe Gln
            115                 120                 125

Lys Lys Trp Lys Glu Asp Val Glu Leu Tyr Arg Gln Lys Val Ala Pro
130                 135                 140
```

-continued

```
Leu Gly Ala Glu Leu Gln Ser Ala Arg Gln Lys Leu Gln Glu Leu
145                 150                 155                 160

Gln Gly Arg Leu Ser Pro Val Ala Glu Glu Phe Arg Asp Arg Met Arg
                165                 170                 175

Thr His Val Asp Ser Leu Arg Thr Gln Leu Ala Pro His Ser Glu Gln
            180                 185                 190

Met Arg Glu Ser Leu Ala Gln Arg Leu Ala Glu Leu Lys Ser Asn Pro
        195                 200                 205

Thr Leu Asn Glu Tyr His Thr Arg Ala Lys Thr His Leu Lys Thr Leu
    210                 215                 220

Gly Glu Lys Ala Arg Pro Ala Leu Glu Asp Leu Arg His Ser Leu Met
225                 230                 235                 240

Pro Met Leu Glu Thr Leu Lys Thr Lys Ala Gln Ser Val Ile Asp Lys
                245                 250                 255

Ala Ser Glu Thr Leu Thr Ala Gln
            260
```

<210> SEQ ID NO 23
<211> LENGTH: 259
<212> TYPE: PRT
<213> ORGANISM: Rattus norvegicus

<400> SEQUENCE: 23

```
Met Lys Ala Ala Val Leu Ala Val Ala Leu Val Phe Leu Thr Gly Cys
1               5                   10                  15

Gln Ala Trp Glu Phe Trp Gln Gln Asp Glu Pro Gln Ser Gln Trp Asp
            20                  25                  30

Arg Val Lys Asp Phe Ala Thr Val Tyr Val Asp Ala Val Lys Asp Ser
        35                  40                  45

Gly Arg Asp Tyr Val Ser Gln Phe Glu Ser Ser Thr Leu Gly Lys Gln
    50                  55                  60

Leu Asn Leu Asn Leu Leu Asp Asn Trp Asp Thr Leu Gly Ser Thr Val
65                  70                  75                  80

Gly Arg Leu Gln Glu Gln Leu Gly Pro Val Thr Gln Glu Phe Trp Ala
                85                  90                  95

Asn Leu Glu Lys Glu Thr Asp Trp Leu Arg Asn Glu Met Asn Lys Asp
            100                 105                 110

Leu Glu Asn Val Lys Gln Lys Met Gln Pro His Leu Asp Glu Phe Gln
        115                 120                 125

Glu Lys Trp Asn Glu Glu Val Glu Ala Tyr Arg Gln Lys Leu Glu Pro
    130                 135                 140

Leu Gly Thr Glu Leu His Lys Asn Ala Lys Glu Met Gln Arg His Leu
145                 150                 155                 160

Lys Val Val Ala Glu Glu Phe Arg Asp Arg Met Arg Val Asn Ala Asp
                165                 170                 175

Ala Leu Arg Ala Lys Phe Gly Leu Tyr Ser Asp Gln Met Arg Glu Asn
            180                 185                 190

Leu Ala Gln Arg Leu Thr Glu Ile Arg Asn His Pro Thr Leu Ile Glu
        195                 200                 205

Tyr His Thr Lys Ala Gly Asp His Leu Arg Thr Leu Gly Glu Lys Ala
    210                 215                 220

Lys Pro Ala Leu Asp Asp Leu Gly Gln Gly Leu Met Pro Val Leu Glu
225                 230                 235                 240
```

```
Ala Trp Lys Ala Lys Ile Met Ser Met Ile Asp Glu Ala Lys Lys Lys
                245                 250                 255

Leu Asn Ala

<210> SEQ ID NO 24
<211> LENGTH: 241
<212> TYPE: PRT
<213> ORGANISM: Erinaceus europaeus

<400> SEQUENCE: 24

Asp Glu Ala Lys Ser Tyr Trp Asp Gln Ile Lys Asp Met Leu Thr Val
1               5                   10                  15

Tyr Val Asp Thr Ala Lys Asp Ser Gly Lys Asp Tyr Leu Thr Ser Leu
            20                  25                  30

Asp Thr Ser Ala Leu Gly Gln Gln Leu Asn Lys Lys Leu Ala Asp Asn
        35                  40                  45

Trp Asp Thr Val Ser Ser Ala Leu Leu Lys Ala Arg Glu Gln Met Lys
    50                  55                  60

Pro Ile Ala Met Glu Phe Trp Gly Asn Leu Glu Lys Asp Thr Glu Gly
65                  70                  75                  80

Leu Arg Gln Thr Val Ser Lys Asp Leu Glu Leu Val Lys Glu Lys Val
                85                  90                  95

Gln Pro Tyr Leu Asp Ser Phe Gln Lys Lys Val Glu Glu Leu Glu
            100                 105                 110

Leu Tyr Arg Gln Lys Val Ala Pro Leu Ser Ala Glu Trp Arg Glu Gln
        115                 120                 125

Ala Arg Gln Lys Ala Gln Glu Leu Gln Gln Lys Ala Gly Glu Leu Gly
    130                 135                 140

Gln Gln His Arg Asp Arg Val Arg Thr His Val Asp Ala Leu Arg Thr
145                 150                 155                 160

Asp Leu Ala Pro Tyr Gly Glu Glu Ala Arg Lys Leu Leu Gln Arg
                165                 170                 175

Leu Gln Asp Ile Lys Ala Lys Ser Gly Asp Leu Ala Glu Tyr Gln Thr
            180                 185                 190

Lys Leu Ser Glu His Leu Lys Ser Phe Gly Glu Lys Ala Gln Pro Thr
        195                 200                 205

Leu Gln Asp Leu Arg His Gly Leu Glu Pro Leu Trp Glu Gly Ile Lys
    210                 215                 220

Ala Gly Ala Met Ser Met Leu Glu Glu Leu Gly Lys Lys Leu Asn Ser
225                 230                 235                 240

Gln

<210> SEQ ID NO 25
<211> LENGTH: 264
<212> TYPE: PRT
<213> ORGANISM: Gallus gallus

<400> SEQUENCE: 25

Met Arg Gly Val Leu Val Thr Leu Ala Val Leu Phe Leu Thr Gly Thr
1               5                   10                  15

Gln Ala Arg Ser Phe Trp Gln His Asp Glu Pro Gln Thr Pro Leu Asp
            20                  25                  30

Arg Ile Arg Asp Met Val Asp Val Tyr Leu Glu Thr Val Lys Ala Ser
        35                  40                  45

Gly Lys Asp Ala Ile Ala Gln Phe Glu Ser Ser Ala Val Gly Lys Gln
    50                  55                  60
```

```
Leu Asp Leu Lys Leu Ala Asp Asn Leu Asp Thr Leu Ser Ala Ala Ala
 65                  70                  75                  80

Ala Lys Leu Arg Glu Asp Met Ala Pro Tyr Tyr Lys Glu Val Arg Glu
                 85                  90                  95

Met Trp Leu Lys Asp Thr Glu Ala Leu Arg Ala Glu Leu Thr Lys Asp
                100                 105                 110

Leu Glu Glu Val Lys Glu Lys Ile Arg Pro Phe Leu Asp Gln Phe Ser
            115                 120                 125

Ala Lys Trp Thr Glu Glu Leu Glu Gln Tyr Arg Gln Arg Leu Thr Pro
        130                 135                 140

Val Ala Gln Glu Leu Lys Glu Leu Thr Lys Gln Lys Val Glu Leu Met
145                 150                 155                 160

Gln Ala Lys Leu Thr Pro Val Ala Glu Glu Ala Arg Asp Arg Leu Arg
                165                 170                 175

Gly His Val Glu Glu Leu Arg Lys Asn Leu Ala Pro Tyr Ser Asp Glu
                180                 185                 190

Leu Arg Gln Lys Leu Ser Gln Lys Leu Glu Glu Ile Arg Glu Lys Gly
            195                 200                 205

Ile Pro Gln Ala Ser Glu Tyr Gln Ala Lys Val Met Glu Gln Leu Ser
        210                 215                 220

Asn Leu Arg Glu Lys Met Thr Pro Leu Val Gln Glu Phe Arg Glu Arg
225                 230                 235                 240

Leu Thr Pro Tyr Ala Glu Asn Leu Lys Asn Arg Leu Ile Ser Phe Leu
                245                 250                 255

Asp Glu Leu Gln Lys Ser Val Ala
                260

<210> SEQ ID NO 26
<211> LENGTH: 264
<212> TYPE: PRT
<213> ORGANISM: Coturnix coturnix japonica

<400> SEQUENCE: 26

Met Arg Gly Val Leu Val Thr Leu Ala Val Leu Phe Leu Thr Gly Thr
  1               5                  10                  15

Gln Ala Arg Ser Phe Trp Gln His Asp Asp Pro Gln Thr Pro Leu Asp
                 20                  25                  30

Arg Ile Arg Asp Met Leu Asp Val Tyr Leu Glu Thr Val Lys Ala Ser
             35                  40                  45

Gly Lys Asp Ala Ile Ser Gln Phe Glu Ser Ser Ala Val Gly Lys Gln
         50                  55                  60

Leu Asp Leu Lys Leu Ala Asp Asn Leu Asp Thr Leu Ser Ala Ala Ala
 65                  70                  75                  80

Ala Lys Leu Arg Glu Asp Met Thr Pro Tyr Tyr Arg Glu Val Arg Glu
                 85                  90                  95

Met Trp Leu Lys Asp Thr Glu Ala Leu Arg Ala Glu Leu Thr Lys Asp
                100                 105                 110

Leu Glu Glu Val Lys Glu Lys Ile Arg Pro Phe Leu Asp Gln Phe Ser
            115                 120                 125

Ala Lys Trp Thr Glu Glu Val Glu Gln Tyr Arg Gln Arg Leu Ala Pro
        130                 135                 140

Val Ala Gln Glu Leu Lys Asp Leu Thr Lys Gln Lys Val Glu Leu Met
145                 150                 155                 160

Gln Ala Lys Leu Thr Pro Val Ala Glu Glu Val Arg Asp Arg Leu Arg
                165                 170                 175
```

```
Glu Gln Val Glu Glu Leu Arg Lys Asn Leu Ala Pro Tyr Ser Ser Glu
            180                 185                 190

Leu Arg Gln Lys Leu Ser Gln Lys Leu Glu Glu Ile Arg Glu Arg Gly
            195                 200                 205

Ile Pro Gln Ala Ser Glu Tyr Gln Ala Lys Val Val Glu Gln Leu Ser
            210                 215                 220

Asn Leu Arg Glu Lys Met Thr Pro Leu Val Gln Glu Phe Lys Glu Arg
225                 230                 235                 240

Leu Thr Pro Tyr Ala Glu Asn Leu Lys Asn Arg Leu Ile Asp Leu Leu
                245                 250                 255

Asp Glu Val Gln Lys Thr Met Ala
            260

<210> SEQ ID NO 27
<211> LENGTH: 264
<212> TYPE: PRT
<213> ORGANISM: Anas platyrhynchos

<400> SEQUENCE: 27

Met Arg Val Val Val Thr Leu Ala Leu Leu Phe Leu Thr Gly Thr
1               5                   10                  15

Gln Ala Arg Tyr Phe Trp Gln His Asp Glu Pro Gln Ala Pro Leu Asp
            20                  25                  30

Arg Leu Arg Asp Leu Val Asp Val Tyr Leu Glu Thr Val Lys Ala Ser
            35                  40                  45

Gly Lys Asp Ala Ile Ala Gln Phe Glu Ala Ser Ala Val Gly Lys Gln
            50                  55                  60

Leu Asp Leu Lys Leu Ala Asp Asn Leu Asp Thr Leu Gly Ala Ala Ala
65                  70                  75                  80

Ala Lys Leu Arg Glu Asp Met Ala Pro Tyr Tyr Lys Glu Val Arg Glu
                85                  90                  95

Met Trp Leu Lys Asp Thr Glu Ser Leu Arg Ala Glu Leu Thr Lys Asp
            100                 105                 110

Leu Glu Glu Val Lys Glu Lys Ile Arg Pro Phe Leu Asp Gln Phe Ser
            115                 120                 125

Ala Lys Trp Thr Glu Glu Leu Glu Gln Tyr Arg Gln Arg Leu Ala Pro
            130                 135                 140

Val Ala Glu Glu Leu Lys Glu Leu Thr Lys Gln Lys Val Glu Leu Met
145                 150                 155                 160

Gln Gln Lys Leu Thr Pro Val Ala Glu Glu Ala Arg Asp Arg Leu Arg
            165                 170                 175

Gly His Val Glu Glu Leu Arg Lys Asn Leu Ala Pro Tyr Ser Asp Glu
            180                 185                 190

Leu Arg Gln Lys Leu Ser Gln Lys Leu Glu Glu Ile Arg Glu Lys Gly
            195                 200                 205

Ile Pro Gln Ala Ala Glu Tyr Gln Ala Lys Val Val Glu Gln Leu Ser
            210                 215                 220

Asn Leu Arg Glu Lys Met Thr Pro Leu Val Gln Asp Phe Lys Glu Arg
225                 230                 235                 240

Leu Thr Pro Tyr Ala Glu Asn Leu Lys Thr Arg Phe Ile Ser Leu Leu
                245                 250                 255

Asp Glu Leu Gln Lys Thr Val Ala
            260
```

-continued

<210> SEQ ID NO 28
<211> LENGTH: 262
<212> TYPE: PRT
<213> ORGANISM: Oncorhynchus mykiss

<400> SEQUENCE: 28

```
Met Lys Phe Leu Ala Leu Ala Leu Thr Ile Leu Leu Ala Ala Gly Thr
1               5                   10                  15

Gln Ala Phe Pro Met Gln Ala Asp Ala Pro Ser Gln Leu Glu His Val
            20                  25                  30

Lys Ala Ala Leu Ser Met Tyr Ile Ala Gln Val Lys Leu Thr Ala Gln
        35                  40                  45

Arg Ser Ile Asp Leu Leu Asp Asp Thr Glu Tyr Lys Glu Tyr Lys Met
    50                  55                  60

Gln Leu Thr Gln Ser Leu Asp Asn Leu Gln Gln Tyr Ala Asp Ala Thr
65                  70                  75                  80

Ser Gln Ser Leu Ala Pro Tyr Ser Glu Ala Phe Gly Thr Gln Leu Thr
                85                  90                  95

Asp Ala Thr Ala Ala Val Arg Ala Glu Val Met Lys Asp Val Glu Glu
            100                 105                 110

Leu Arg Ser Gln Leu Glu Pro Lys Arg Ala Glu Leu Lys Glu Val Leu
        115                 120                 125

Asp Lys His Ile Asp Glu Tyr Arg Lys Lys Leu Glu Pro Leu Ile Lys
    130                 135                 140

Glu His Ile Glu Leu Arg Arg Thr Glu Met Glu Ala Phe Arg Ala Lys
145                 150                 155                 160

Met Glu Pro Ile Val Glu Glu Leu Arg Ala Lys Val Ala Ile Asn Val
                165                 170                 175

Glu Glu Thr Lys Thr Lys Leu Met Pro Ile Val Glu Ile Val Arg Ala
            180                 185                 190

Lys Leu Thr Glu Arg Leu Glu Glu Leu Arg Thr Leu Ala Ala Pro Tyr
        195                 200                 205

Ala Glu Glu Tyr Lys Glu Gln Met Ile Lys Ala Val Gly Glu Val Arg
    210                 215                 220

Glu Lys Val Ser Pro Leu Ser Glu Asp Phe Lys Gly Gln Val Gly Pro
225                 230                 235                 240

Ala Ala Glu Gln Ala Lys Gln Lys Leu Leu Ala Phe Tyr Glu Thr Ile
                245                 250                 255

Ser Gln Ala Met Lys Ala
            260
```

<210> SEQ ID NO 29
<211> LENGTH: 262
<212> TYPE: PRT
<213> ORGANISM: Salmo trutta

<400> SEQUENCE: 29

```
Met Lys Phe Leu Ala Leu Ala Leu Thr Ile Leu Leu Ala Ala Ala Thr
1               5                   10                  15

Gln Ala Val Pro Met Gln Ala Asp Ala Pro Ser Gln Leu Glu His Val
            20                  25                  30

Lys Val Ala Met Met Glu Tyr Met Ala Gln Val Lys Glu Thr Gly Gln
        35                  40                  45

Arg Ser Ile Asp Leu Leu Asp Asp Thr Glu Phe Lys Glu Tyr Lys Val
    50                  55                  60
```

```
Gln Leu Ser Gln Ser Leu Asp Asn Leu Gln Gln Tyr Ala Gln Thr Thr
 65                  70                  75                  80

Ser Gln Ser Leu Ala Pro Tyr Ser Glu Ala Phe Gly Ala Gln Leu Thr
                 85                  90                  95

Asp Ala Ala Ala Val Arg Ala Glu Val Met Lys Asp Val Glu Asp
            100                 105                 110

Val Arg Thr Gln Leu Glu Pro Lys Arg Ala Glu Leu Lys Glu Val Leu
            115                 120                 125

Asp Lys His Ile Asp Glu Tyr Arg Lys Lys Leu Glu Pro Leu Ile Lys
        130                 135                 140

Glu Ile Val Glu Gln Arg Arg Thr Glu Leu Glu Ala Phe Arg Val Lys
145                 150                 155                 160

Met Glu Pro Val Val Glu Glu Met Arg Ala Lys Val Ser Thr Asn Val
                165                 170                 175

Glu Glu Thr Lys Ala Lys Leu Met Pro Ile Val Glu Thr Val Arg Ala
            180                 185                 190

Lys Leu Thr Glu Arg Leu Glu Glu Leu Arg Thr Leu Ala Ala Pro Tyr
        195                 200                 205

Ala Glu Glu Tyr Lys Glu Gln Met Phe Lys Ala Val Gly Glu Val Arg
        210                 215                 220

Glu Lys Val Gly Pro Leu Thr Asn Asp Phe Lys Gly Gln Val Gly Pro
225                 230                 235                 240

Ala Ala Glu Gln Ala Lys Glu Lys Leu Met Asp Phe Tyr Glu Thr Ile
                245                 250                 255

Ser Gln Ala Met Lys Ala
            260

<210> SEQ ID NO 30
<211> LENGTH: 258
<212> TYPE: PRT
<213> ORGANISM: Salmo salar

<400> SEQUENCE: 30

Met Lys Phe Leu Val Leu Ala Leu Thr Ile Leu Leu Ala Ala Gly Thr
 1               5                  10                  15

Gln Ala Phe Pro Met Gln Ala Asp Ala Pro Ser Gln Leu Glu His Val
                20                  25                  30

Lys Ala Ala Leu Asn Met Tyr Ile Ala Gln Val Lys Leu Thr Ala Gln
            35                  40                  45

Arg Ser Ile Asp Leu Leu Asp Asp Thr Glu Tyr Lys Glu Tyr Lys Met
 50                  55                  60

Gln Leu Ser Gln Ser Leu Asp Asn Leu Gln Gln Phe Ala Asp Ser Thr
 65                  70                  75                  80

Ser Lys Ser Trp Pro Pro Thr Pro Arg Ser Ser Ala Pro Ser Cys Asp
                 85                  90                  95

Ala Thr Ala Thr Val Arg Ala Glu Val Met Lys Asp Val Glu Asp Val
            100                 105                 110

Arg Thr Gln Leu Glu Pro Lys Arg Ala Glu Leu Thr Glu Val Leu Asn
        115                 120                 125

Lys His Ile Asp Glu Tyr Arg Lys Lys Leu Glu Pro Leu Ile Lys Gln
        130                 135                 140

His Ile Glu Leu Arg Arg Thr Glu Met Asp Ala Phe Arg Ala Lys Ile
145                 150                 155                 160

Asp Pro Val Val Glu Glu Met Arg Ala Lys Val Ala Val Asn Val Glu
                165                 170                 175
```

```
Glu Thr Lys Thr Lys Leu Met Pro Ile Val Glu Ile Val Arg Ala Lys
            180                 185                 190

Leu Thr Glu Arg Leu Glu Glu Leu Arg Thr Leu Ala Ala Pro Tyr Ala
        195                 200                 205

Glu Glu Tyr Lys Glu Gln Met Phe Lys Ala Val Gly Glu Val Arg Glu
    210                 215                 220

Lys Val Ala Pro Leu Ser Glu Asp Phe Lys Ala Arg Trp Ala Pro Pro
225                 230                 235                 240

Pro Arg Arg Pro Ser Lys Ser Ser Trp Leu Ser Thr Arg Pro Ser Ala
                245                 250                 255

Arg Pro

<210> SEQ ID NO 31
<211> LENGTH: 262
<212> TYPE: PRT
<213> ORGANISM: Brachydanio rerio

<400> SEQUENCE: 31

Met Lys Phe Val Ala Leu Ala Leu Thr Leu Leu Ala Leu Gly Ser
1               5                   10                  15

Gln Ala Asn Leu Phe Gln Ala Asp Ala Pro Thr Gln Leu Glu His Tyr
            20                  25                  30

Lys Ala Ala Ala Leu Val Tyr Leu Asn Gln Val Lys Asp Gln Ala Glu
        35                  40                  45

Lys Ala Leu Asp Asn Leu Asp Gly Thr Asp Tyr Glu Gln Tyr Lys Leu
    50                  55                  60

Gln Leu Ser Glu Ser Leu Thr Lys Leu Gln Glu Tyr Ala Gln Thr Thr
65                  70                  75                  80

Ser Gln Ala Leu Thr Pro Tyr Ala Glu Thr Ile Ser Thr Gln Leu Met
                85                  90                  95

Glu Asn Thr Lys Gln Leu Arg Glu Arg Val Met Thr Asp Val Glu Asp
            100                 105                 110

Leu Arg Ser Lys Leu Glu Pro His Arg Ala Glu Leu Tyr Thr Ala Leu
        115                 120                 125

Gln Lys His Ile Asp Glu Tyr Arg Glu Lys Leu Glu Pro Val Phe Gln
    130                 135                 140

Glu Tyr Ser Ala Leu Asn Arg Gln Asn Ala Glu Gln Leu Arg Ala Lys
145                 150                 155                 160

Leu Glu Pro Leu Met Asp Asp Ile Arg Lys Ala Phe Glu Ser Asn Ile
                165                 170                 175

Glu Glu Thr Lys Ser Lys Val Val Pro Met Val Glu Ala Val Arg Thr
            180                 185                 190

Lys Leu Thr Glu Arg Leu Glu Asp Leu Arg Thr Met Ala Ala Pro Tyr
        195                 200                 205

Ala Glu Glu Tyr Lys Glu Gln Leu Val Lys Ala Val Glu Glu Ala Arg
    210                 215                 220

Glu Lys Ile Ala Pro His Thr Gln Asp Leu Gln Thr Arg Met Glu Pro
225                 230                 235                 240

Tyr Met Glu Asn Val Arg Thr Thr Phe Ala Gln Met Tyr Glu Thr Ile
                245                 250                 255

Ala Lys Ala Ile Gln Ala
            260
```

```
<210> SEQ ID NO 32
<211> LENGTH: 260
<212> TYPE: PRT
<213> ORGANISM: Sparus aurata

<400> SEQUENCE: 32

Met Lys Phe Ala Ala Leu Ala Leu Ala Leu Leu Ala Val Gly Ser
1               5                   10                  15

His Ala Ala Ser Met Gln Ala Asp Ala Pro Ser Gln Leu Asp His Ala
            20                  25                  30

Arg Ala Val Leu Asp Val Tyr Leu Thr Gln Val Lys Asp Met Ser Leu
        35                  40                  45

Arg Ala Val Asn Gln Leu Asp Asp Pro Gln Tyr Ala Glu Phe Lys Thr
    50                  55                  60

Asn Leu Ala Gln Arg Ile Glu Glu Met Tyr Thr Gln Ile Lys Thr Leu
65                  70                  75                  80

Gln Gly Ser Val Ser Pro Met Thr Asp Ser Phe Tyr Asn Thr Val Met
                85                  90                  95

Glu Val Thr Lys Asp Thr Arg Glu Ser Leu Asn Val Asp Leu Glu Ala
            100                 105                 110

Leu Lys Ser Ser Leu Ala Pro Gln Asn Glu Gln Leu Lys Gln Val Ile
        115                 120                 125

Glu Lys His Leu Asn Asp Tyr Arg Thr Leu Leu Thr Pro Ile Tyr Asn
    130                 135                 140

Asp Tyr Lys Thr Lys His Asp Glu Glu Met Ala Ala Leu Lys Thr Arg
145                 150                 155                 160

Leu Glu Pro Val Met Glu Glu Leu Arg Thr Lys Ile Gln Ala Asn Val
                165                 170                 175

Glu Glu Thr Lys Ala Val Leu Met Pro Met Val Glu Thr Val Arg Thr
            180                 185                 190

Lys Val Thr Glu Arg Leu Glu Ser Leu Arg Glu Val Val Gln Pro Tyr
        195                 200                 205

Val Gln Glu Tyr Lys Glu Gln Met Lys Gln Met Tyr Asp Gln Ala Gln
    210                 215                 220

Thr Val Asp Thr Asp Ala Leu Arg Thr Lys Ile Thr Pro Leu Val Glu
225                 230                 235                 240

Glu Ile Lys Val Lys Met Asn Ala Ile Phe Glu Ile Ile Ala Ala Ser
                245                 250                 255

Val Thr Lys Ser
        260

<210> SEQ ID NO 33
<211> LENGTH: 396
<212> TYPE: PRT
<213> ORGANISM: Homo sapiens

<400> SEQUENCE: 33

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60
```

-continued

```
Lys Leu Gly Glu Val Asn Thr Tyr Ala Gly Asp Leu Gln Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395
```

<210> SEQ ID NO 34
<211> LENGTH: 429
<212> TYPE: PRT
<213> ORGANISM: Macaca fascicularis

<400> SEQUENCE: 34

```
Met Phe Leu Lys Ala Val Val Leu Thr Leu Ala Leu Val Ala Val Thr
  1               5                  10                  15

Gly Ala Arg Ala Glu Val Ser Ala Asp Gln Val Ala Thr Val Met Trp
                 20                  25                  30

Asp Tyr Phe Ser Gln Leu Ser Ser Asn Ala Lys Glu Ala Val Glu His
             35                  40                  45
```

```
Leu Gln Lys Ser Glu Leu Thr Gln Gln Leu Asn Ala Leu Phe Gln Asp
 50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Arg Lys Glu Leu Glu Glu Val Arg Ala Arg
                100                 105                 110

Leu Leu Pro His Ala Asn Glu Val Ser Gln Lys Ile Gly Glu Asn Val
                115                 120                 125

Arg Glu Leu Gln Gln Arg Leu Glu Pro Tyr Thr Asp Gln Leu Arg Thr
        130                 135                 140

Gln Val Asn Thr Gln Thr Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Thr Ser Leu Arg Pro His Ala Asp Gln Leu Lys Ala Lys Ile Asp Gln
                180                 185                 190

Asn Val Glu Glu Leu Lys Glu Arg Leu Thr Pro Tyr Ala Asp Glu Phe
                195                 200                 205

Lys Val Lys Ile Asp Gln Thr Val Glu Glu Leu Arg Arg Ser Leu Ala
210                 215                 220

Pro Tyr Ala Gln Asp Ala Gln Glu Lys Leu Asn His Gln Leu Glu Gly
225                 230                 235                 240

Leu Ala Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Met Arg Gly Asn Leu Arg Gly Asn Thr Glu Gly Leu Gln Lys Ser
                275                 280                 285

Leu Ala Glu Leu Gly Gly His Leu Asp Arg His Val Glu Glu Phe Arg
        290                 295                 300

Leu Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Asn Thr Leu
                355                 360                 365

Ser Leu Pro Glu Pro Glu Gln Gln Arg Glu Gln Gln Gln Glu Gln Gln
        370                 375                 380

Gln Glu Gln Glu Gln Gln Gln Gln Gln Gln Glu Gln Gln Gln Glu Gln
385                 390                 395                 400

Gln Glu Gln Gln Arg Glu Gln Gln Gln Glu Gln Gln Gln Glu Gln
                405                 410                 415

Gln Gln Glu Gln Val Gln Met Leu Ala Pro Leu Glu Ser
        420                 425

<210> SEQ ID NO 35
<211> LENGTH: 395
<212> TYPE: PRT
<213> ORGANISM: Mus musculus
```

```
<400> SEQUENCE: 35

Met Phe Leu Lys Ala Ala Val Leu Thr Leu Ala Leu Val Ala Ile Thr
1               5                   10                  15

Gly Thr Arg Ala Glu Val Thr Ser Asp Gln Val Ala Asn Val Val Trp
            20                  25                  30

Asp Tyr Phe Thr Gln Leu Ser Asn Asn Ala Lys Glu Ala Val Glu Gln
            35                  40                  45

Phe Gln Lys Thr Asp Val Thr Gln Gln Leu Ser Thr Leu Phe Gln Asp
        50                  55                  60

Lys Leu Gly Asp Ala Ser Thr Tyr Ala Asp Gly Val His Asn Lys Leu
65                  70                  75                  80

Val Pro Phe Val Val Gln Leu Ser Gly His Leu Ala Lys Glu Thr Glu
                85                  90                  95

Arg Val Lys Glu Glu Ile Lys Lys Glu Leu Glu Asp Leu Arg Asp Arg
            100                 105                 110

Met Met Pro His Ala Asn Lys Val Thr Gln Thr Phe Gly Glu Asn Met
            115                 120                 125

Gln Lys Leu Gln Glu His Leu Lys Pro Tyr Ala Val Asp Leu Gln Asp
        130                 135                 140

Gln Ile Asn Thr Gln Thr Gln Glu Met Lys Leu Gln Leu Thr Pro Tyr
145                 150                 155                 160

Ile Gln Arg Met Gln Thr Thr Ile Lys Glu Asn Val Asp Asn Leu His
                165                 170                 175

Thr Ser Met Met Pro Leu Ala Thr Asn Leu Lys Asp Lys Phe Asn Arg
            180                 185                 190

Asn Met Glu Glu Leu Lys Gly His Leu Thr Pro Arg Ala Asn Glu Leu
        195                 200                 205

Lys Ala Thr Ile Asp Gln Asn Leu Glu Asp Leu Arg Arg Ser Leu Ala
210                 215                 220

Pro Leu Thr Val Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Ala Lys Ile Asp Gln Leu Gln Lys Asn Leu Ala Pro Leu Val Glu
            260                 265                 270

Asp Val Gln Ser Lys Val Lys Gly Asn Thr Glu Gly Leu Gln Lys Ser
        275                 280                 285

Leu Glu Asp Leu Asn Arg Gln Leu Glu Gln Gln Val Glu Glu Phe Arg
290                 295                 300

Arg Thr Val Glu Pro Met Gly Glu Met Phe Asn Lys Ala Leu Val Gln
305                 310                 315                 320

Gln Leu Glu Gln Phe Arg Gln Gln Leu Gly Pro Asn Ser Gly Glu Val
                325                 330                 335

Glu Ser His Leu Ser Phe Leu Glu Lys Ser Leu Arg Glu Lys Val Asn
            340                 345                 350

Ser Phe Met Ser Thr Leu Glu Lys Lys Gly Ser Pro Asp Gln Pro Gln
        355                 360                 365

Ala Leu Pro Leu Pro Glu Gln Ala Gln Glu Gln Ala Gln Glu Gln Ala
370                 375                 380

Gln Glu Gln Val Gln Pro Lys Pro Leu Glu Ser
385                 390                 395
```

<210> SEQ ID NO 36
<211> LENGTH: 401
<212> TYPE: PRT
<213> ORGANISM: Papio anubis

<400> SEQUENCE: 36

```
Gly Ala Arg Ala Glu Val Ser Ala Asp Gln Val Ala Thr Val Met Trp
1               5                   10                  15

Asp Tyr Phe Ser Gln Leu Ser Ser Asn Ala Lys Glu Ala Val Glu His
            20                  25                  30

Leu Gln Lys Ser Glu Leu Thr Gln Gln Leu Asn Ala Leu Phe Gln Asp
        35                  40                  45

Lys Leu Gly Glu Val Asn Thr Tyr Ala Gly Asp Leu Gln Lys Lys Leu
    50                  55                  60

Val Pro Phe Ala Thr Glu Leu His Glu Arg Leu Ala Lys Asp Ser Lys
65                  70                  75                  80

Lys Leu Lys Glu Glu Ile Arg Lys Glu Leu Glu Glu Val Arg Ala Arg
                85                  90                  95

Leu Leu Pro His Ala Asn Glu Val Ser Gln Lys Ile Gly Glu Asn Val
            100                 105                 110

Arg Glu Leu Gln Gln Arg Leu Glu Pro Tyr Thr Asp Gln Leu Arg Thr
        115                 120                 125

Gln Val Asn Thr Gln Thr Glu Gln Leu Arg Arg Gln Leu Thr Pro Tyr
    130                 135                 140

Ala Gln Arg Met Glu Arg Val Leu Arg Glu Asn Ala Asp Ser Leu Gln
145                 150                 155                 160

Thr Ser Leu Arg Pro His Ala Asp Gln Leu Lys Ala Lys Ile Asp Gln
                165                 170                 175

Asn Val Glu Glu Leu Lys Gly Arg Leu Thr Pro Tyr Ala Asp Glu Phe
            180                 185                 190

Lys Val Lys Ile Asp Gln Thr Val Glu Glu Leu Arg Arg Ser Leu Ala
        195                 200                 205

Pro Tyr Ala Gln Asp Ala Gln Glu Lys Leu Asn His Gln Leu Glu Gly
    210                 215                 220

Leu Ala Phe Gln Met Lys Lys Asn Ala Glu Glu Leu Lys Ala Arg Ile
225                 230                 235                 240

Ser Ala Ser Ala Glu Glu Leu Arg Gln Arg Leu Ala Pro Leu Ala Glu
                245                 250                 255

Asp Met Arg Gly Asn Leu Arg Gly Asn Thr Glu Gly Leu Gln Lys Ser
            260                 265                 270

Leu Ala Glu Leu Gly Gly His Leu Asp Arg His Val Glu Glu Phe Arg
        275                 280                 285

Leu Arg Val Glu Pro Tyr Gly Glu Asn Phe Asn Lys Ala Leu Val Gln
    290                 295                 300

Gln Met Glu Gln Leu Arg Gln Lys Leu Gly Pro His Ala Gly Asp Val
305                 310                 315                 320

Glu Gly His Leu Ser Phe Leu Glu Lys Asp Leu Arg Asp Lys Val Asn
                325                 330                 335

Ser Phe Phe Ser Thr Phe Lys Glu Lys Glu Ser Gln Asp Asn Thr Leu
            340                 345                 350

Ser Leu Pro Glu Pro Glu Gln Gln Glu Gln Gln Glu Gln Glu
        355                 360                 365

Gln Gln Gln Gln Gln Gln Glu Gln Gln Gln Glu Gln Gln Gln
    370                 375                 380
```

```
Glu Gln Glu Gln Gln Gln Gln Val Gln Met Leu Ala Pro Leu Glu
385                 390                 395                 400

Ser
```

<210> SEQ ID NO 37
<211> LENGTH: 382
<212> TYPE: PRT
<213> ORGANISM: Sus scrofa

<400> SEQUENCE: 37

```
Met Phe Leu Lys Ala Val Val Leu Ser Leu Ala Leu Val Ala Val Thr
1               5                   10                  15

Gly Ala Arg Ala Glu Val Asn Ala Asp Gln Val Ala Thr Val Met Trp
            20                  25                  30

Asp Tyr Phe Ser Gln Leu Gly Ser Asn Ala Lys Lys Ala Val Glu His
        35                  40                  45

Leu Gln Lys Ser Glu Leu Thr Gln Gln Leu Asn Thr Leu Phe Gln Asp
    50                  55                  60

Lys Leu Gly Glu Val Asn Thr Tyr Thr Glu Asp Leu Gln Lys Lys Leu
65                  70                  75                  80

Val Pro Phe Ala Thr Glu Leu His Glu Arg Leu Thr Lys Asp Ser Glu
                85                  90                  95

Lys Leu Lys Glu Glu Ile Arg Arg Glu Leu Glu Leu Arg Ala Arg
            100                 105                 110

Leu Leu Pro His Ala Thr Glu Val Ser Gln Lys Ile Gly Asp Asn Val
            115                 120                 125

Arg Glu Leu Gln Gln Arg Leu Gly Pro Phe Thr Gly Gly Leu Arg Thr
130                 135                 140

Gln Val Asn Thr Gln Val Gln Gln Leu Gln Arg Gln Leu Lys Pro Tyr
145                 150                 155                 160

Ala Glu Arg Met Glu Ser Val Leu Arg Gln Asn Ile Arg Asn Leu Glu
                165                 170                 175

Ala Ser Val Ala Pro Tyr Ala Asp Glu Phe Lys Ala Lys Ile Asp Gln
            180                 185                 190

Asn Val Glu Glu Leu Lys Gly Ser Leu Thr Pro Tyr Ala Glu Glu Leu
    195                 200                 205

Lys Ala Lys Ile Asp Gln Asn Val Glu Glu Leu Arg Arg Ser Leu Ala
    210                 215                 220

Pro Tyr Ala Gln Asp Val Gln Glu Lys Leu Asn His Gln Leu Glu Gly
225                 230                 235                 240

Leu Ala Phe Gln Met Lys Lys Gln Ala Glu Glu Leu Lys Ala Lys Ile
                245                 250                 255

Ser Ala Asn Ala Asp Glu Leu Arg Gln Lys Leu Val Pro Val Ala Glu
            260                 265                 270

Asn Val His Gly His Leu Lys Gly Asn Thr Glu Gly Leu Gln Lys Ser
            275                 280                 285

Leu Leu Glu Leu Arg Ser His Leu Asp Gln Gln Val Glu Glu Phe Arg
    290                 295                 300

Leu Lys Val Glu Pro Tyr Gly Glu Thr Phe Asn Lys Ala Leu Val Gln
305                 310                 315                 320

Gln Val Glu Asp Leu Arg Gln Lys Leu Gly Pro Leu Ala Gly Asp Val
                325                 330                 335

Glu Gly His Leu Ser Phe Leu Glu Lys Asp Leu Arg Asp Lys Val Asn
            340                 345                 350
```

```
Thr Phe Phe Ser Thr Leu Lys Glu Glu Ala Ser Gln Gly Gln Ser Gln
        355                 360                 365

Ala Leu Pro Ala Gln Glu Lys Ala Gln Ala Pro Leu Glu Gly
    370                 375                 380

<210> SEQ ID NO 38
<211> LENGTH: 391
<212> TYPE: PRT
<213> ORGANISM: Rattus norvegicus

<400> SEQUENCE: 38

Met Phe Leu Lys Ala Val Val Leu Thr Val Ala Leu Val Ala Ile Thr
1               5                   10                  15

Gly Thr Gln Ala Glu Val Thr Ser Asp Gln Val Ala Asn Val Met Trp
            20                  25                  30

Asp Tyr Phe Thr Gln Leu Ser Asn Asn Ala Lys Glu Ala Val Glu Gln
        35                  40                  45

Leu Gln Lys Thr Asp Val Thr Gln Gln Leu Asn Thr Leu Phe Gln Asp
    50                  55                  60

Lys Leu Gly Asn Ile Asn Thr Tyr Ala Asp Asp Leu Gln Asn Lys Leu
65                  70                  75                  80

Val Pro Phe Ala Val Gln Leu Ser Gly His Leu Thr Lys Glu Thr Glu
                85                  90                  95

Arg Val Arg Glu Glu Ile Gln Lys Glu Leu Glu Asp Leu Arg Ala Asn
            100                 105                 110

Met Met Pro His Ala Asn Lys Val Ser Gln Met Phe Gly Asp Asn Val
        115                 120                 125

Gln Lys Leu Gln Glu His Leu Arg Pro Tyr Ala Thr Asp Leu Gln Ala
    130                 135                 140

Gln Ile Asn Ala Gln Thr Gln Asp Met Lys Arg Gln Leu Thr Pro Tyr
145                 150                 155                 160

Ile Gln Arg Met Gln Thr Thr Ile Gln Asp Asn Val Glu Asn Leu Gln
                165                 170                 175

Ser Ser Met Val Pro Phe Ala Asn Glu Leu Lys Glu Lys Phe Asn Gln
            180                 185                 190

Asn Met Glu Gly Leu Lys Gly Gln Leu Thr Pro Arg Ala Asn Glu Leu
        195                 200                 205

Lys Ala Thr Ile Asp Gln Asn Leu Glu Asp Leu Arg Ser Arg Leu Ala
    210                 215                 220

Pro Leu Ala Glu Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Thr Asn Ile Asp Gln Leu Gln Lys Asn Leu Ala Pro Leu Val Glu
            260                 265                 270

Asp Val Gln Ser Lys Leu Lys Gly Asn Thr Glu Gly Leu Gln Lys Ser
        275                 280                 285

Leu Glu Asp Leu Asn Lys Gln Leu Asp Gln Gln Val Glu Val Phe Arg
    290                 295                 300

Arg Ala Val Glu Pro Leu Gly Asp Lys Phe Asn Met Ala Leu Val Gln
305                 310                 315                 320

Gln Met Glu Lys Phe Arg Gln Gln Leu Gly Ser Asp Ser Gly Asp Val
                325                 330                 335

Glu Ser His Leu Ser Phe Leu Glu Lys Asn Leu Arg Glu Lys Val Ser
            340                 345                 350
```

```
Ser Phe Met Ser Thr Leu Gln Lys Lys Gly Ser Pro Asp Gln Pro Leu
        355                 360                 365

Ala Leu Pro Leu Pro Glu Gln Val Gln Glu Gln Val Gln Glu Gln Val
        370                 375                 380

Gln Pro Lys Pro Leu Glu Ser
385                 390

<210> SEQ ID NO 39
<211> LENGTH: 36
<212> TYPE: PRT
<213> ORGANISM: Homo sapiens

<400> SEQUENCE: 39

Val Val Asn Thr Lys Met Phe Glu Glu Leu Lys Ser Arg Leu Asp Thr
1               5                  10                  15

Leu Ala Gln Glu Val Ala Leu Leu Lys Glu Gln Gln Ala Leu Gln Thr
                20                  25                  30

Val Cys Leu Lys
        35

<210> SEQ ID NO 40
<211> LENGTH: 36
<212> TYPE: PRT
<213> ORGANISM: Mus musculus

<400> SEQUENCE: 40

Leu Val Ser Ser Lys Met Phe Glu Glu Leu Lys Asn Arg Met Asp Val
1               5                  10                  15

Leu Ala Gln Glu Val Ala Leu Leu Lys Glu Lys Gln Ala Leu Gln Thr
                20                  25                  30

Val Cys Leu Lys
        35

<210> SEQ ID NO 41
<211> LENGTH: 36
<212> TYPE: PRT
<213> ORGANISM: Box taurus

<400> SEQUENCE: 41

Arg Arg Val Lys Glu Lys Asp Gly Asp Leu Lys Thr Gln Val Glu Lys
1               5                  10                  15

Leu Trp Arg Glu Val Asn Ala Leu Lys Glu Met Gln Ala Leu Gln Thr
                20                  25                  30

Val Cys Leu Arg
        35

<210> SEQ ID NO 42
<211> LENGTH: 36
<212> TYPE: PRT
<213> ORGANISM: Carcharhinus springeri

<400> SEQUENCE: 42

Ser Lys Ser Gly Lys Gly Lys Asp Asp Leu Arg Asn Glu Ile Asp Lys
1               5                  10                  15

Leu Trp Arg Glu Val Asn Ser Leu Lys Glu Met Gln Ala Leu Gln Thr
                20                  25                  30

Val Cys Leu Lys
        35
```

<210> SEQ ID NO 43
<211> LENGTH: 1282
<212> TYPE: DNA
<213> ORGANISM: Artificial Sequence
<220> FEATURE:
<223> OTHER INFORMATION: pT7 H6UbiFx Apo A-1 plasmid
<221> NAME/KEY: CDS
<222> LOCATION: (100)..(1107)
<223> OTHER INFORMATION:

<400> SEQUENCE: 43

```
gatctcgatc ccgcgaaatt aatacgatac actataggga gaccacaacg gtttccctct      60
agaaataatt ttgtttaact ttaagaagga gatatacat atg gga tcg cat cac        114
                                           Met Gly Ser His His
                                             1               5 cat cac cat cac gga tca cag atc ttt gtg aag acc ctc act ggc aaa       162
His His His His Gly Ser Gln Ile Phe Val Lys Thr Leu Thr Gly Lys
                 10                  15                  20 acc atc acc ctt gag gtc gag ccc agt gac acc att gag aat gtc aaa       210
Thr Ile Thr Leu Glu Val Glu Pro Ser Asp Thr Ile Glu Asn Val Lys
             25                  30                  35 gcc aaa att caa gac aag gag ggt atc cca cct gac cag cag cgt ctg       258
Ala Lys Ile Gln Asp Lys Glu Gly Ile Pro Pro Asp Gln Gln Arg Leu
         40                  45                  50 ata ttt gcc ggc aaa cag ctg gaa gat gga cgt act ttg tct gac tac       306
Ile Phe Ala Gly Lys Gln Leu Glu Asp Gly Arg Thr Leu Ser Asp Tyr
 55                  60                  65 aat att caa aag gag tct act ctt cat ctt gtg ttg aga ctt cgt ggt       354
Asn Ile Gln Lys Glu Ser Thr Leu His Leu Val Leu Arg Leu Arg Gly
 70                  75                  80                  85 gga tcc atc gag ggt agg ggt gga gat gaa ccc ccc cag agc ccc tgg       402
Gly Ser Ile Glu Gly Arg Gly Gly Asp Glu Pro Pro Gln Ser Pro Trp
                 90                  95                 100 gat cga gtg aag gac ctg gcc act gtg tac gtg gat gtg ctc aaa gac       450
Asp Arg Val Lys Asp Leu Ala Thr Val Tyr Val Asp Val Leu Lys Asp
             105                 110                 115 agc ggc aga gac tat gtg tcc cag ttt gaa ggc tcc gcc ttg gga aaa       498
Ser Gly Arg Asp Tyr Val Ser Gln Phe Glu Gly Ser Ala Leu Gly Lys
         120                 125                 130 cag cta aac cta aag ctc ctt gac aac tgg gac agc gtg acc tcc acc       546
Gln Leu Asn Leu Lys Leu Leu Asp Asn Trp Asp Ser Val Thr Ser Thr
 135                 140                 145 ttc agc aag ctg cgc gaa cag ctc ggc cct gtg acc cag gag ttc tgg       594
Phe Ser Lys Leu Arg Glu Gln Leu Gly Pro Val Thr Gln Glu Phe Trp
150                 155                 160                 165 gat aac ctg gaa aag gag aca gag ggc ctg agg cag gag atg agc aag       642
Asp Asn Leu Glu Lys Glu Thr Glu Gly Leu Arg Gln Glu Met Ser Lys
                 170                 175                 180 gat ctg gag gag gtg aag gcc aag gtg cag ccc tac ctg gac gac ttc       690
Asp Leu Glu Glu Val Lys Ala Lys Val Gln Pro Tyr Leu Asp Asp Phe
             185                 190                 195 cag aag aag tgg cag gag gag atg gag ctc tac cgc cag aag gtg gag       738
Gln Lys Lys Trp Gln Glu Glu Met Glu Leu Tyr Arg Gln Lys Val Glu
         200                 205                 210 ccg ctg cgc gca gag ctc caa gag ggc gcg cgc cag aag ctg cac gag       786
Pro Leu Arg Ala Glu Leu Gln Glu Gly Ala Arg Gln Lys Leu His Glu
 215                 220                 225 ctg caa gag aag ctg agc cca ctg ggc gag gag atg cgc gac cgc gcg       834
Leu Gln Glu Lys Leu Ser Pro Leu Gly Glu Glu Met Arg Asp Arg Ala
230                 235                 240                 245
```

```
cgc gcc cat gtg gac gcg ctg cgc acg cat ctg gcc ccc tac agc gac      882
Arg Ala His Val Asp Ala Leu Arg Thr His Leu Ala Pro Tyr Ser Asp
            250                 255                 260 gag ctg cgc cag cgc ttg gcc gcg cgc ctt gag gct ctc aag gag aac      930
Glu Leu Arg Gln Arg Leu Ala Ala Arg Leu Glu Ala Leu Lys Glu Asn
            265                 270                 275 ggc ggc gcc aga ctg gcc gag tac cac gcc aag gcc acc gag cat ctg      978
Gly Gly Ala Arg Leu Ala Glu Tyr His Ala Lys Ala Thr Glu His Leu
        280                 285                 290 agc acg ctc agc gag aag gcc aag ccc gcg ctc gag gac ctc cgc caa     1026
Ser Thr Leu Ser Glu Lys Ala Lys Pro Ala Leu Glu Asp Leu Arg Gln
        295                 300                 305 ggc ctg ctg ccc gtg ctg gag agc ttc aag gtc agc ttc ctg agc gct     1074
Gly Leu Leu Pro Val Leu Glu Ser Phe Lys Val Ser Phe Leu Ser Ala
310                 315                 320                 325 ctc gag gag tac act aag aag ctc aac acc cag taagcatgca agcttgaatt   1127
Leu Glu Glu Tyr Thr Lys Lys Leu Asn Thr Gln
                330                 335 ccgatccggc tgctaacaaa gcccgaaagg aagctgagtt ggctgcctgc caccgctgag   1187
ctgagcaata actagcataa cccctctgcc accgctgtgg ggcctctaaa cgggtcttga   1247
ggggtttttt gctgaaagga ggaactatat ccgat                              1282

<210> SEQ ID NO 44
<211> LENGTH: 336
<212> TYPE: PRT
<213> ORGANISM: Artificial Sequence
<220> FEATURE:
<223> OTHER INFORMATION: pT7 H6UbiFx Apo A-1 plasmid

<400> SEQUENCE: 44

Met Gly Ser His His His His His His Gly Ser Gln Ile Phe Val Lys
1               5                   10                  15

Thr Leu Thr Gly Lys Thr Ile Thr Leu Glu Val Glu Pro Ser Asp Thr
            20                  25                  30

Ile Glu Asn Val Lys Ala Lys Ile Gln Asp Lys Glu Gly Ile Pro Pro
        35                  40                  45

Asp Gln Gln Arg Leu Ile Phe Ala Gly Lys Gln Leu Glu Asp Gly Arg
    50                  55                  60

Thr Leu Ser Asp Tyr Asn Ile Gln Lys Glu Ser Thr Leu His Leu Val
65                  70                  75                  80

Leu Arg Leu Arg Gly Gly Ser Ile Glu Gly Arg Gly Asp Glu Pro
            85                  90                  95

Pro Gln Ser Pro Trp Asp Arg Val Lys Asp Leu Ala Thr Val Tyr Val
            100                 105                 110

Asp Val Leu Lys Asp Ser Gly Arg Asp Tyr Val Ser Gln Phe Glu Gly
        115                 120                 125

Ser Ala Leu Gly Lys Gln Leu Asn Leu Lys Leu Leu Asp Asn Trp Asp
    130                 135                 140

Ser Val Thr Ser Thr Phe Ser Lys Leu Arg Glu Gln Leu Gly Pro Val
145                 150                 155                 160

Thr Gln Glu Phe Trp Asp Asn Leu Glu Lys Glu Thr Glu Gly Leu Arg
                165                 170                 175

Gln Glu Met Ser Lys Asp Leu Glu Glu Val Lys Ala Lys Val Gln Pro
            180                 185                 190

Tyr Leu Asp Asp Phe Gln Lys Lys Trp Gln Glu Glu Met Glu Leu Tyr
        195                 200                 205
```

-continued

```
Arg Gln Lys Val Glu Pro Leu Arg Ala Glu Leu Gln Glu Gly Ala Arg
    210                 215                 220
Gln Lys Leu His Glu Leu Gln Glu Lys Leu Ser Pro Leu Gly Glu Glu
225                 230                 235                 240
Met Arg Asp Arg Ala Arg Ala His Val Asp Ala Leu Arg Thr His Leu
                245                 250                 255
Ala Pro Tyr Ser Asp Glu Leu Arg Gln Arg Leu Ala Ala Arg Leu Glu
            260                 265                 270
Ala Leu Lys Glu Asn Gly Gly Ala Arg Leu Ala Glu Tyr His Ala Lys
        275                 280                 285
Ala Thr Glu His Leu Ser Thr Leu Ser Glu Lys Ala Lys Pro Ala Leu
    290                 295                 300
Glu Asp Leu Arg Gln Gly Leu Leu Pro Val Leu Glu Ser Phe Lys Val
305                 310                 315                 320
Ser Phe Leu Ser Ala Leu Glu Glu Tyr Thr Lys Lys Leu Asn Thr Gln
                325                 330                 335
```

<210> SEQ ID NO 45
<211> LENGTH: 1285
<212> TYPE: DNA
<213> ORGANISM: Artificial Sequence
<220> FEATURE:
<223> OTHER INFORMATION: T7 H6UbiFx Cys-Apo A-1 plasmid
<221> NAME/KEY: CDS
<222> LOCATION: (100)..(1110)
<223> OTHER INFORMATION:

<400> SEQUENCE: 45

```
gatctcgatc ccgcgaaatt aatacgatac actataggga gaccacaacg gtttccctct      60
agaaataatt ttgtttaact ttaagaagga gatatacat atg gga tcg cat cac         114
                                          Met Gly Ser His His
                                           1               5 cat cac cat cac gga tca cag atc ttt gtg aag acc ctc act ggc aaa        162
His His His His Gly Ser Gln Ile Phe Val Lys Thr Leu Thr Gly Lys
             10                  15                  20 acc atc acc ctt gag gtc gag ccc agt gac acc att gag aat gtc aaa        210
Thr Ile Thr Leu Glu Val Glu Pro Ser Asp Thr Ile Glu Asn Val Lys
         25                  30                  35 gcc aaa att caa gac aag gag ggt atc cca cct gac cag cag cgt ctg        258
Ala Lys Ile Gln Asp Lys Glu Gly Ile Pro Pro Asp Gln Gln Arg Leu
     40                  45                  50 ata ttt gcc ggc aaa cag ctg gaa gat gga cgt act ttg tct gac tac        306
Ile Phe Ala Gly Lys Gln Leu Glu Asp Gly Arg Thr Leu Ser Asp Tyr
 55                  60                  65 aat att caa aag gag tct act ctt cat ctt gtg ttg aga ctt cgt ggt        354
Asn Ile Gln Lys Glu Ser Thr Leu His Leu Val Leu Arg Leu Arg Gly
 70                  75                  80                  85 gga tcc atc gag ggt agg ggt gga tgt gat gaa ccc ccc cag agc ccc        402
Gly Ser Ile Glu Gly Arg Gly Gly Cys Asp Glu Pro Pro Gln Ser Pro
                 90                  95                 100 tgg gat cga gtg aag gac ctg gcc act gtg tac gtg gat gtg ctc aaa        450
Trp Asp Arg Val Lys Asp Leu Ala Thr Val Tyr Val Asp Val Leu Lys
            105                 110                 115 gac agc ggc aga gac tat gtg tcc cag ttt gaa ggc tcc gcc ttg gga        498
Asp Ser Gly Arg Asp Tyr Val Ser Gln Phe Glu Gly Ser Ala Leu Gly
        120                 125                 130 aaa cag cta aac cta aag ctc ctt gac aac tgg gac agc gtg acc tcc        546
Lys Gln Leu Asn Leu Lys Leu Leu Asp Asn Trp Asp Ser Val Thr Ser
    135                 140                 145
```

-continued

| | | |
|---|---|---|
| acc ttc agc aag ctg cgc gaa cag ctc ggc cct gtg acc cag gag ttc<br>Thr Phe Ser Lys Leu Arg Glu Gln Leu Gly Pro Val Thr Gln Glu Phe<br>150                        155                        160                        165 | 594 | |
| tgg gat aac ctg gaa aag gag aca gag ggc ctg agg cag gag atg agc<br>Trp Asp Asn Leu Glu Lys Glu Thr Glu Gly Leu Arg Gln Glu Met Ser<br>                  170                        175                        180 | 642 | |
| aag gat ctg gag gag gtg aag gcc aag gtg cag ccc tac ctg gac gac<br>Lys Asp Leu Glu Glu Val Lys Ala Lys Val Gln Pro Tyr Leu Asp Asp<br>                  185                        190                        195 | 690 | |
| ttc cag aag aag tgg cag gag gag atg gag ctc tac cgc cag aag gtg<br>Phe Gln Lys Lys Trp Gln Glu Glu Met Glu Leu Tyr Arg Gln Lys Val<br>                  200                        205                        210 | 738 | |
| gag ccg ctg cgc gca gag ctc caa gag ggc gcg cgc cag aag ctg cac<br>Glu Pro Leu Arg Ala Glu Leu Gln Glu Gly Ala Arg Gln Lys Leu His<br>215                        220                        225 | 786 | |
| gag ctg caa gag aag ctg agc cca ctg ggc gag gag atg cgc gac cgc<br>Glu Leu Gln Glu Lys Leu Ser Pro Leu Gly Glu Glu Met Arg Asp Arg<br>230                        235                        240                        245 | 834 | |
| gcg cgc gcc cat gtg gac gcg ctg cgc acg cat ctg gcc ccc tac agc<br>Ala Arg Ala His Val Asp Ala Leu Arg Thr His Leu Ala Pro Tyr Ser<br>                  250                        255                        260 | 882 | |
| gac gag ctg cgc cag cgc ttg gcc gcg cgc ctt gag gct ctc aag gag<br>Asp Glu Leu Arg Gln Arg Leu Ala Ala Arg Leu Glu Ala Leu Lys Glu<br>                  265                        270                        275 | 930 | |
| aac ggc ggc gcc aga ctg gcc gag tac cac gcc aag gcc acc gag cat<br>Asn Gly Gly Ala Arg Leu Ala Glu Tyr His Ala Lys Ala Thr Glu His<br>                  280                        285                        290 | 978 | |
| ctg agc acg ctc agc gag aag gcc aag ccc gcg ctc gag gac ctc cgc<br>Leu Ser Thr Leu Ser Glu Lys Ala Lys Pro Ala Leu Glu Asp Leu Arg<br>295                        300                        305 | 1026 | |
| caa ggc ctg ctg ccc gtg ctg gag agc ttc aag gtc agc ttc ctg agc<br>Gln Gly Leu Leu Pro Val Leu Glu Ser Phe Lys Val Ser Phe Leu Ser<br>310                        315                        320                        325 | 1074 | |
| gct ctc gag gag tac act aag aag ctc aac acc cag taagcatgca<br>Ala Leu Glu Glu Tyr Thr Lys Lys Leu Asn Thr Gln<br>                  330                        335 | 1120 | |
| agcttgaatt ccgatccggc tgctaacaaa gcccgaaagg aagctgagtt ggctgcctgc | 1180 | |
| caccgctgag ctgagcaata actagcataa cccctctgcc accgctgtgg ggcctctaaa | 1240 | |
| cgggtcttga ggggtttttt gctgaaagga ggaactatat ccgat | 1285 | |

<210> SEQ ID NO 46
<211> LENGTH: 337
<212> TYPE: PRT
<213> ORGANISM: Artificial Sequence
<220> FEATURE:
<223> OTHER INFORMATION: T7 H6UbiFx Cys-Apo A-1 plasmid

<400> SEQUENCE: 46

Met Gly Ser His His His His His Gly Ser Gln Ile Phe Val Lys
1               5                     10                   15

Thr Leu Thr Gly Lys Thr Ile Thr Leu Glu Val Glu Pro Ser Asp Thr
                 20                     25                     30

Ile Glu Asn Val Lys Ala Lys Ile Gln Asp Lys Glu Gly Ile Pro Pro
           35                     40                     45

Asp Gln Gln Arg Leu Ile Phe Ala Gly Lys Gln Leu Glu Asp Gly Arg
    50                     55                     60

Thr Leu Ser Asp Tyr Asn Ile Gln Lys Glu Ser Thr Leu His Leu Val
65                 70                     75                     80

```
Leu Arg Leu Arg Gly Gly Ser Ile Glu Gly Arg Gly Cys Asp Glu
            85                  90                  95

Pro Pro Gln Ser Pro Trp Asp Arg Val Lys Asp Leu Ala Thr Val Tyr
            100                 105                 110

Val Asp Val Leu Lys Asp Ser Gly Arg Asp Tyr Val Ser Gln Phe Glu
            115                 120                 125

Gly Ser Ala Leu Gly Lys Gln Leu Asn Leu Lys Leu Leu Asp Asn Trp
130                 135                 140

Asp Ser Val Thr Ser Thr Phe Ser Lys Leu Arg Glu Gln Leu Gly Pro
145                 150                 155                 160

Val Thr Gln Glu Phe Trp Asp Asn Leu Glu Lys Glu Thr Glu Gly Leu
            165                 170                 175

Arg Gln Glu Met Ser Lys Asp Leu Glu Glu Val Lys Ala Lys Val Gln
            180                 185                 190

Pro Tyr Leu Asp Asp Phe Gln Lys Lys Trp Gln Glu Glu Met Glu Leu
            195                 200                 205

Tyr Arg Gln Lys Val Glu Pro Leu Arg Ala Glu Leu Gln Glu Gly Ala
210                 215                 220

Arg Gln Lys Leu His Glu Leu Gln Glu Lys Leu Ser Pro Leu Gly Glu
225                 230                 235                 240

Glu Met Arg Asp Arg Ala Arg Ala His Val Asp Ala Leu Arg Thr His
            245                 250                 255

Leu Ala Pro Tyr Ser Asp Glu Leu Arg Gln Arg Leu Ala Ala Arg Leu
            260                 265                 270

Glu Ala Leu Lys Glu Asn Gly Gly Ala Arg Leu Ala Glu Tyr His Ala
            275                 280                 285

Lys Ala Thr Glu His Leu Ser Thr Leu Ser Glu Lys Ala Lys Pro Ala
            290                 295                 300

Leu Glu Asp Leu Arg Gln Gly Leu Leu Pro Val Leu Glu Ser Phe Lys
305                 310                 315                 320

Val Ser Phe Leu Ser Ala Leu Glu Glu Tyr Thr Lys Lys Leu Asn Thr
            325                 330                 335

Gln

<210> SEQ ID NO 47
<211> LENGTH: 1217
<212> TYPE: DNA
<213> ORGANISM: Artificial Sequence
<220> FEATURE:
<223> OTHER INFORMATION: pT7 H6 Trip-A-Apo A-1 - AmpR plasmid
<221> NAME/KEY: CDS
<222> LOCATION: (100)..(1047)
<223> OTHER INFORMATION:

<400> SEQUENCE: 47
gatctcgatc ccgcgaaatt aatacgatac actataggga gaccacaacg gtttccctct      60
agaaataatt ttgtttaact ttaagaagga gatatacat atg gga tcg cat cac       114
                                            Met Gly Ser His His
                                             1               5 cat cac cat cac gga tcg atc cag ggt aga tct cct ggt acc gag cca       162
His His His His Gly Ser Ile Gln Gly Arg Ser Pro Gly Thr Glu Pro
                10                  15                  20 cca acc cag aag ccc aag aag att gta aat gcc aag aaa gat gtt gtg       210
Pro Thr Gln Lys Pro Lys Lys Ile Val Asn Ala Lys Lys Asp Val Val
            25                  30                  35
```

-continued

| | | |
|---|---|---|
| aac aca aag atg ttt gag gag ctc aag agc cgt ctg gac acc ctg gcc<br>Asn Thr Lys Met Phe Glu Glu Leu Lys Ser Arg Leu Asp Thr Leu Ala<br>     40                           45                     50 | 258 |
| cag gag gtg gcc ctg ctg aag gag cag cag gcc ctg cag acg gtc tcc<br>Gln Glu Val Ala Leu Leu Lys Glu Gln Gln Ala Leu Gln Thr Val Ser<br>  55                        60                     65 | 306 |
| ctg aag gga tcc gat gaa ccc ccc cag agc ccc tgg gat cga gtg aag<br>Leu Lys Gly Ser Asp Glu Pro Pro Gln Ser Pro Trp Asp Arg Val Lys<br>70                     75                     80                     85 | 354 |
| gac ctg gcc act gtg tac gtg gat gtg ctc aaa gac agc ggc aga gac<br>Asp Leu Ala Thr Val Tyr Val Asp Val Leu Lys Asp Ser Gly Arg Asp<br>                     90                     95                   100 | 402 |
| tat gtg tcc cag ttt gaa ggc tcc gcc ttg gga aaa cag cta aac cta<br>Tyr Val Ser Gln Phe Glu Gly Ser Ala Leu Gly Lys Gln Leu Asn Leu<br>                 105                     110                   115 | 450 |
| aag ctc ctt gac aac tgg gac agc gtg acc tcc acc ttc agc aag ctg<br>Lys Leu Leu Asp Asn Trp Asp Ser Val Thr Ser Thr Phe Ser Lys Leu<br>                 120                     125                   130 | 498 |
| cgc gaa cag ctc ggc cct gtg acc cag gag ttc tgg gat aac ctg gaa<br>Arg Glu Gln Leu Gly Pro Val Thr Gln Glu Phe Trp Asp Asn Leu Glu<br>      135                   140                     145 | 546 |
| aag gag aca gag ggc ctg agg cag gag atg agc aag gat ctg gag gag<br>Lys Glu Thr Glu Gly Leu Arg Gln Glu Met Ser Lys Asp Leu Glu Glu<br>150                   155                     160                     165 | 594 |
| gtg aag gcc aag gtg cag ccc tac ctg gac gac ttc cag aag aag tgg<br>Val Lys Ala Lys Val Gln Pro Tyr Leu Asp Asp Phe Gln Lys Lys Trp<br>                 170                     175                   180 | 642 |
| cag gag gag atg gag ctc tac cgc cag aag gtg gag ccg ctg cgc gca<br>Gln Glu Glu Met Glu Leu Tyr Arg Gln Lys Val Glu Pro Leu Arg Ala<br>                 185                     190                   195 | 690 |
| gag ctc caa gag ggc gcg cgc cag aag ctg cac gag ctg caa gag aag<br>Glu Leu Gln Glu Gly Ala Arg Gln Lys Leu His Glu Leu Gln Glu Lys<br>      200                   205                     210 | 738 |
| ctg agc cca ctg ggc gag gag atg cgc gac cgc gcg cgc gcc cat gtg<br>Leu Ser Pro Leu Gly Glu Glu Met Arg Asp Arg Ala Arg Ala His Val<br>      215                   220                     225 | 786 |
| gac gcg ctg cgc acg cat ctg gcc ccc tac agc gac gag ctg cgc cag<br>Asp Ala Leu Arg Thr His Leu Ala Pro Tyr Ser Asp Glu Leu Arg Gln<br>230                   235                     240                     245 | 834 |
| cgc ttg gcc gcg cgc ctt gag gct ctc aag gag aac ggc ggc gcc aga<br>Arg Leu Ala Ala Arg Leu Glu Ala Leu Lys Glu Asn Gly Gly Ala Arg<br>                 250                     255                   260 | 882 |
| ctg gcc gag tac cac gcc aag gcc acc gag cat ctg agc acg ctc agc<br>Leu Ala Glu Tyr His Ala Lys Ala Thr Glu His Leu Ser Thr Leu Ser<br>      265                   270                     275 | 930 |
| gag aag gcc aag ccc gcg ctc gag gac ctc cgc caa ggc ctg ctg ccc<br>Glu Lys Ala Lys Pro Ala Leu Glu Asp Leu Arg Gln Gly Leu Leu Pro<br>                 280                     285                   290 | 978 |
| gtg ctg gag agc ttc aag gtc agc ttc ctg agc gct ctc gag gag tac<br>Val Leu Glu Ser Phe Lys Val Ser Phe Leu Ser Ala Leu Glu Glu Tyr<br>      295                   300                     305 | 1026 |
| act aag aag ctc aac acc cag taataagctt gaattccgat ccggctgcta<br>Thr Lys Lys Leu Asn Thr Gln<br>310                   315 | 1077 |
| acaaagcccg aaaggaagct gagttggctg cctgccaccg ctgagctgag caataactag | 1137 |
| cataacccct ctgccaccgc tgtggggcct ctaaacgggt cttgaggggt tttttgctga | 1197 |
| aaggaggaac tatatccgat | 1217 |

```
<210> SEQ ID NO 48
<211> LENGTH: 316
<212> TYPE: PRT
<213> ORGANISM: Artificial Sequence
<220> FEATURE:
<223> OTHER INFORMATION: pT7 H6 Trip-A-Apo A-1 - AmpR plasmid

<400> SEQUENCE: 48

Met Gly Ser His His His His His Gly Ser Ile Gln Gly Arg Ser
1               5                   10                  15

Pro Gly Thr Glu Pro Pro Thr Gln Lys Pro Lys Lys Ile Val Asn Ala
            20                  25                  30

Lys Lys Asp Val Val Asn Thr Lys Met Phe Glu Glu Leu Lys Ser Arg
        35                  40                  45

Leu Asp Thr Leu Ala Gln Glu Val Ala Leu Leu Lys Glu Gln Gln Ala
    50                  55                  60

Leu Gln Thr Val Ser Leu Lys Gly Ser Asp Glu Pro Pro Gln Ser Pro
65                  70                  75                  80

Trp Asp Arg Val Lys Asp Leu Ala Thr Val Tyr Val Asp Val Leu Lys
                85                  90                  95

Asp Ser Gly Arg Asp Tyr Val Ser Gln Phe Glu Gly Ser Ala Leu Gly
            100                 105                 110

Lys Gln Leu Asn Leu Lys Leu Leu Asp Asn Trp Asp Ser Val Thr Ser
        115                 120                 125

Thr Phe Ser Lys Leu Arg Glu Gln Leu Gly Pro Val Thr Gln Glu Phe
    130                 135                 140

Trp Asp Asn Leu Glu Lys Glu Thr Glu Gly Leu Arg Gln Glu Met Ser
145                 150                 155                 160

Lys Asp Leu Glu Glu Val Lys Ala Lys Val Gln Pro Tyr Leu Asp Asp
                165                 170                 175

Phe Gln Lys Lys Trp Gln Glu Glu Met Glu Leu Tyr Arg Gln Lys Val
            180                 185                 190

Glu Pro Leu Arg Ala Glu Leu Gln Glu Gly Ala Arg Gln Lys Leu His
        195                 200                 205

Glu Leu Gln Glu Lys Leu Ser Pro Leu Gly Glu Glu Met Arg Asp Arg
    210                 215                 220

Ala Arg Ala His Val Asp Ala Leu Arg Thr His Leu Ala Pro Tyr Ser
225                 230                 235                 240

Asp Glu Leu Arg Gln Arg Leu Ala Ala Arg Leu Glu Ala Leu Lys Glu
                245                 250                 255

Asn Gly Gly Ala Arg Leu Ala Glu Tyr His Ala Lys Ala Thr Glu His
            260                 265                 270

Leu Ser Thr Leu Ser Glu Lys Ala Lys Pro Ala Leu Glu Asp Leu Arg
        275                 280                 285

Gln Gly Leu Leu Pro Val Leu Glu Ser Phe Lys Val Ser Phe Leu Ser
    290                 295                 300

Ala Leu Glu Glu Tyr Thr Lys Lys Leu Asn Thr Gln
305                 310                 315

<210> SEQ ID NO 49
<211> LENGTH: 1088
<212> TYPE: DNA
<213> ORGANISM: Artificial Sequence
<220> FEATURE:
<223> OTHER INFORMATION: pT7H6 Trip-A-Apo A-1-del 43 - AmpR plasmid
<221> NAME/KEY: CDS
<222> LOCATION: (100)..(918)
<223> OTHER INFORMATION:
```

-continued

<400> SEQUENCE: 49

```
gatctcgatc cgcgaaatt aatacgatac actatagga gaccacaacg gtttccctct    60
agaaataatt ttgtttaact ttaagaagga gatatacat atg gga tcg cat cac   114
                                            Met Gly Ser His His
                                            1               5 cat cac cat cac gga tcg atc cag ggt aga tct cct ggt acc gag cca  162
His His His His Gly Ser Ile Gln Gly Arg Ser Pro Gly Thr Glu Pro
            10                  15                  20 cca acc cag aag ccc aag aag att gta aat gcc aag aaa gat gtt gtg  210
Pro Thr Gln Lys Pro Lys Lys Ile Val Asn Ala Lys Lys Asp Val Val
         25                  30                  35 aac aca aag atg ttt gag gag ctc aag agc cgt ctg gac acc ctg gcc  258
Asn Thr Lys Met Phe Glu Glu Leu Lys Ser Arg Leu Asp Thr Leu Ala
             40                  45                  50 cag gag gtg gcc ctg ctg aag gag cag cag gcc ctg cag acg gtc tcc  306
Gln Glu Val Ala Leu Leu Lys Glu Gln Gln Ala Leu Gln Thr Val Ser
     55                  60                  65 ctg aag gga tcc cta aag ctc ctt gac aac tgg gac agc gtg acc tcc  354
Leu Lys Gly Ser Leu Lys Leu Leu Asp Asn Trp Asp Ser Val Thr Ser
70                  75                  80                  85 acc ttc agc aag ctg cgc gaa cag ctc ggc cct gtg acc cag gag ttc  402
Thr Phe Ser Lys Leu Arg Glu Gln Leu Gly Pro Val Thr Gln Glu Phe
                 90                  95                 100 tgg gat aac ctg gaa aag gag aca gag ggc ctg agg cag gag atg agc  450
Trp Asp Asn Leu Glu Lys Glu Thr Glu Gly Leu Arg Gln Glu Met Ser
            105                 110                 115 aag gat ctg gag gag gtg aag gcc aag gtg cag ccc tac ctg gac gac  498
Lys Asp Leu Glu Glu Val Lys Ala Lys Val Gln Pro Tyr Leu Asp Asp
        120                 125                 130 ttc cag aag aag tgg cag gag gag atg gag ctc tac cgc cag aag gtg  546
Phe Gln Lys Lys Trp Gln Glu Glu Met Glu Leu Tyr Arg Gln Lys Val
    135                 140                 145 gag ccg ctg cgc gca gag ctc caa gag ggc gcg cgc cag aag ctg cac  594
Glu Pro Leu Arg Ala Glu Leu Gln Glu Gly Ala Arg Gln Lys Leu His
150                 155                 160                 165 gag ctg caa gag aag ctg agc cca ctg ggc gag gag atg cgc gac cgc  642
Glu Leu Gln Glu Lys Leu Ser Pro Leu Gly Glu Glu Met Arg Asp Arg
                170                 175                 180 gcg cgc gcc cat gtg gac gcg ctg cgc acg cat ctg gcc ccc tac agc  690
Ala Arg Ala His Val Asp Ala Leu Arg Thr His Leu Ala Pro Tyr Ser
            185                 190                 195 gac gag ctg cgc cag cgc ttg gcc gcg cgc ctt gag gct ctc aag gag  738
Asp Glu Leu Arg Gln Arg Leu Ala Ala Arg Leu Glu Ala Leu Lys Glu
        200                 205                 210 aac ggc ggc gcc aga ctg gcc gag tac cac gcc aag gcc acc gag cat  786
Asn Gly Gly Ala Arg Leu Ala Glu Tyr His Ala Lys Ala Thr Glu His
    215                 220                 225 ctg agc acg ctc agc gag aag gcc aag ccc gcg ctc gag gac ctc cgc  834
Leu Ser Thr Leu Ser Glu Lys Ala Lys Pro Ala Leu Glu Asp Leu Arg
230                 235                 240                 245 caa ggc ctg ctg ccc gtg ctg gag agc ttc aag gtc agc ttc ctg agc  882
Gln Gly Leu Leu Pro Val Leu Glu Ser Phe Lys Val Ser Phe Leu Ser
                250                 255                 260 gct ctc gag gag tac act aag aag ctc aac acc cag taataagctt       928
Ala Leu Glu Glu Tyr Thr Lys Lys Leu Asn Thr Gln
            265                 270
```

―continued

```
gaattccgat ccggctgcta acaaagcccg aaaggaagct gagttggctg cctgccaccg      988
ctgagctgag caataactag cataacccct ctgccaccgc tgtggggcct ctaaacgggt     1048 cttgagggt tttttgctga aggaggaac tatatccgat                             1088
```

<210> SEQ ID NO 50
<211> LENGTH: 273
<212> TYPE: PRT
<213> ORGANISM: Artificial Sequence
<220> FEATURE:
<223> OTHER INFORMATION: pT7H6 Trip-A-Apo A-1-del 43 - AmpR plasmid

<400> SEQUENCE: 50

```
Met Gly Ser His His His His His His Gly Ser Ile Gln Gly Arg Ser
1               5                   10                  15

Pro Gly Thr Glu Pro Pro Thr Gln Lys Pro Lys Lys Ile Val Asn Ala
            20                  25                  30

Lys Lys Asp Val Val Asn Thr Lys Met Phe Glu Glu Leu Lys Ser Arg
        35                  40                  45

Leu Asp Thr Leu Ala Gln Glu Val Ala Leu Leu Lys Glu Gln Gln Ala
    50                  55                  60

Leu Gln Thr Val Ser Leu Lys Gly Ser Leu Lys Leu Leu Asp Asn Trp
65                  70                  75                  80

Asp Ser Val Thr Ser Thr Phe Ser Lys Leu Arg Glu Gln Leu Gly Pro
                85                  90                  95

Val Thr Gln Glu Phe Trp Asp Asn Leu Glu Lys Glu Thr Glu Gly Leu
            100                 105                 110

Arg Gln Glu Met Ser Lys Asp Leu Glu Glu Val Lys Ala Lys Val Gln
        115                 120                 125

Pro Tyr Leu Asp Asp Phe Gln Lys Lys Trp Gln Glu Glu Met Glu Leu
    130                 135                 140

Tyr Arg Gln Lys Val Glu Pro Leu Arg Ala Glu Leu Gln Glu Gly Ala
145                 150                 155                 160

Arg Gln Lys Leu His Glu Leu Gln Glu Lys Leu Ser Pro Leu Gly Glu
                165                 170                 175

Glu Met Arg Asp Arg Ala Arg Ala His Val Asp Ala Leu Arg Thr His
            180                 185                 190

Leu Ala Pro Tyr Ser Asp Glu Leu Arg Gln Arg Leu Ala Ala Arg Leu
        195                 200                 205

Glu Ala Leu Lys Glu Asn Gly Gly Ala Arg Leu Ala Glu Tyr His Ala
    210                 215                 220

Lys Ala Thr Glu His Leu Ser Thr Leu Ser Glu Lys Ala Lys Pro Ala
225                 230                 235                 240

Leu Glu Asp Leu Arg Gln Gly Leu Leu Pro Val Leu Glu Ser Phe Lys
                245                 250                 255

Val Ser Phe Leu Ser Ala Leu Glu Glu Tyr Thr Lys Lys Leu Asn Thr
            260                 265                 270

Gln
```

<210> SEQ ID NO 51
<211> LENGTH: 1057
<212> TYPE: DNA
<213> ORGANISM: Artificial Sequence
<220> FEATURE:
<223> OTHER INFORMATION: pT7 H6 Fx Cys-Apo A1 plasmid
<221> NAME/KEY: CDS
<222> LOCATION: (100)..(882)
<223> OTHER INFORMATION:

<400> SEQUENCE: 51

```
gatctcgatc cgcgaaatt aatacgatac actataggga gaccacaacg gtttccctct        60
agaaataatt tgtttaact ttaagaagga gatatacat atg gga tcg cat cac         114
                                            Met Gly Ser His His
                                            1               5 cat cac cat cac gga tcc atc gag ggt agg ggt gga tgt gat gaa ccc        162
His His His His Gly Ser Ile Glu Gly Arg Gly Gly Cys Asp Glu Pro
            10                  15                  20 ccc cag agc ccc tgg gat cga gtg aag gac ctg gcc act gtg tac gtg       210
Pro Gln Ser Pro Trp Asp Arg Val Lys Asp Leu Ala Thr Val Tyr Val
        25                  30                  35 gat gtg ctc aaa gac agc ggc aga gac tat gtg tcc cag ttt gaa ggc       258
Asp Val Leu Lys Asp Ser Gly Arg Asp Tyr Val Ser Gln Phe Glu Gly
    40                  45                  50 tcc gcc ttg gga aaa cag cta aac cta aag ctc ctt gac aac tgg gac       306
Ser Ala Leu Gly Lys Gln Leu Asn Leu Lys Leu Leu Asp Asn Trp Asp
55                  60                  65 agc gtg acc tcc acc ttc agc aag ctg cgc gaa cag ctc ggc cct gtg       354
Ser Val Thr Ser Thr Phe Ser Lys Leu Arg Glu Gln Leu Gly Pro Val
70                  75                  80                  85 acc cag gag ttc tgg gat aac ctg gaa aag gag aca gag ggc ctg agg       402
Thr Gln Glu Phe Trp Asp Asn Leu Glu Lys Glu Thr Glu Gly Leu Arg
            90                  95                  100 cag gag atg agc aag gat ctg gag gag gtg aag gcc aag gtg cag ccc       450
Gln Glu Met Ser Lys Asp Leu Glu Glu Val Lys Ala Lys Val Gln Pro
        105                 110                 115 tac ctg gac gac ttc cag aag aag tgg cag gag gag atg gag ctc tac       498
Tyr Leu Asp Asp Phe Gln Lys Lys Trp Gln Glu Glu Met Glu Leu Tyr
    120                 125                 130 cgc cag aag gtg gag ccg ctg cgc gca gag ctc caa gag ggc gcg cgc       546
Arg Gln Lys Val Glu Pro Leu Arg Ala Glu Leu Gln Glu Gly Ala Arg
135                 140                 145 cag aag ctg cac gag ctg caa gag aag ctg agc cca ctg ggc gag gag       594
Gln Lys Leu His Glu Leu Gln Glu Lys Leu Ser Pro Leu Gly Glu Glu
150                 155                 160                 165 atg cgc gac cgc gcg cgc gcc cat gtg gac gcg ctg cgc acg cat ctg       642
Met Arg Asp Arg Ala Arg Ala His Val Asp Ala Leu Arg Thr His Leu
            170                 175                 180 gcc ccc tac agc gac gag ctg cgc cag cgc ttg gcc gcg cgc ctt gag       690
Ala Pro Tyr Ser Asp Glu Leu Arg Gln Arg Leu Ala Ala Arg Leu Glu
        185                 190                 195 gct ctc aag gag aac ggc ggc gcc aga ctg gcc gag tac cac gcc aag       738
Ala Leu Lys Glu Asn Gly Gly Ala Arg Leu Ala Glu Tyr His Ala Lys
    200                 205                 210 gcc acc gag cat ctg agc acg ctc agc gag aag gcc aag ccc gcg ctc       786
Ala Thr Glu His Leu Ser Thr Leu Ser Glu Lys Ala Lys Pro Ala Leu
215                 220                 225 gag gac ctc cgc caa ggc ctg ctg ccc gtg ctg gag agc ttc aag gtc       834
Glu Asp Leu Arg Gln Gly Leu Leu Pro Val Leu Glu Ser Phe Lys Val
230                 235                 240                 245 agc ttc ctg agc gct ctc gag gag tac act aag aag ctc aac acc cag       882
Ser Phe Leu Ser Ala Leu Glu Glu Tyr Thr Lys Lys Leu Asn Thr Gln
            250                 255                 260 taagcatgca agcttgaatt ccgatccggc tgctaacaaa gcccgaaagg aagctgagtt       942
ggctgcctgc caccgctgag ctgagcaata actagcataa cccctctgcc accgctgtgg      1002
ggcctctaaa cgggtcttga ggggtttttt gctgaaagga ggaactatat ccgat           1057
```

<210> SEQ ID NO 52
<211> LENGTH: 261
<212> TYPE: PRT
<213> ORGANISM: Artificial Sequence
<220> FEATURE:
<223> OTHER INFORMATION: pT7 H6 Fx Cys-Apo A1 plasmid

<400> SEQUENCE: 52

```
Met Gly Ser His His His His His Gly Ser Ile Glu Gly Arg Gly
1               5                   10                  15

Gly Cys Asp Glu Pro Pro Gln Ser Pro Trp Asp Arg Val Lys Asp Leu
                20              25                  30

Ala Thr Val Tyr Val Asp Val Leu Lys Asp Ser Gly Arg Asp Tyr Val
                35              40                  45

Ser Gln Phe Glu Gly Ser Ala Leu Gly Lys Gln Leu Asn Leu Lys Leu
50              55                  60

Leu Asp Asn Trp Asp Ser Val Thr Ser Thr Phe Ser Lys Leu Arg Glu
65              70                  75                  80

Gln Leu Gly Pro Val Thr Gln Glu Phe Trp Asp Asn Leu Glu Lys Glu
                85                  90                  95

Thr Glu Gly Leu Arg Gln Glu Met Ser Lys Asp Leu Glu Glu Val Lys
                100                 105                 110

Ala Lys Val Gln Pro Tyr Leu Asp Asp Phe Gln Lys Lys Trp Gln Glu
                115                 120                 125

Glu Met Glu Leu Tyr Arg Gln Lys Val Glu Pro Leu Arg Ala Glu Leu
130                 135                 140

Gln Glu Gly Ala Arg Gln Lys Leu His Glu Leu Gln Glu Lys Leu Ser
145                 150                 155                 160

Pro Leu Gly Glu Glu Met Arg Asp Arg Ala Arg Ala His Val Asp Ala
                165                 170                 175

Leu Arg Thr His Leu Ala Pro Tyr Ser Asp Glu Leu Arg Gln Arg Leu
                180                 185                 190

Ala Ala Arg Leu Glu Ala Leu Lys Glu Asn Gly Gly Ala Arg Leu Ala
                195                 200                 205

Glu Tyr His Ala Lys Ala Thr Glu His Leu Ser Thr Leu Ser Glu Lys
                210                 215                 220

Ala Lys Pro Ala Leu Glu Asp Leu Arg Gln Gly Leu Leu Pro Val Leu
225                 230                 235                 240

Glu Ser Phe Lys Val Ser Phe Leu Ser Ala Leu Glu Glu Tyr Thr Lys
                245                 250                 255

Lys Leu Asn Thr Gln
                260
```

<210> SEQ ID NO 53
<211> LENGTH: 1217
<212> TYPE: DNA
<213> ORGANISM: Artificial Sequence
<220> FEATURE:
<223> OTHER INFORMATION: pT7H6 Trip-A-Apo A1 K9A K15A - AmpR plasmid
<221> NAME/KEY: CDS
<222> LOCATION: (100)..(1047)
<223> OTHER INFORMATION:

<400> SEQUENCE: 53

```
gatctcgatc ccgcgaaatt aatacgatac actataggga gaccacaacg gtttccctct      60
agaaataatt ttgtttaact ttaagaagga gatatacat atg gga tcg cat cac        114
                                            Met Gly Ser His His
                                            1               5
```

| | |
|---|---|
| cat cac cat cac gga tcg atc cag ggt aga tct cct ggt acc gag cca<br>His His His His Gly Ser Ile Gln Gly Arg Ser Pro Gly Thr Glu Pro<br>                     10                  15                20 | 162 |
| cca acc cag aag ccc aag gcg att gta aat gcc aag gca gat gtt gtg<br>Pro Thr Gln Lys Pro Lys Ala Ile Val Asn Ala Lys Ala Asp Val Val<br>          25                      30                    35 | 210 |
| aac aca aag atg ttt gag gag ctc aag agc cgt ctg gac acc ctg gcc<br>Asn Thr Lys Met Phe Glu Glu Leu Lys Ser Arg Leu Asp Thr Leu Ala<br>40                     45                    50 | 258 |
| cag gag gtg gcc ctg ctg aag gag cag cag gcc ctg cag acg gtc tcc<br>Gln Glu Val Ala Leu Leu Lys Glu Gln Gln Ala Leu Gln Thr Val Ser<br>    55                      60                    65 | 306 |
| ctg aag gga tcc gat gaa ccc ccc cag agc ccc tgg gat cga gtg aag<br>Leu Lys Gly Ser Asp Glu Pro Pro Gln Ser Pro Trp Asp Arg Val Lys<br>70                 75                    80                85 | 354 |
| gac ctg gcc act gtg tac gtg gat gtg ctc aaa gac agc ggc aga gac<br>Asp Leu Ala Thr Val Tyr Val Asp Val Leu Lys Asp Ser Gly Arg Asp<br>                     90                  95                100 | 402 |
| tat gtg tcc cag ttt gaa ggc tcc gcc ttg gga aaa cag cta aac cta<br>Tyr Val Ser Gln Phe Glu Gly Ser Ala Leu Gly Lys Gln Leu Asn Leu<br>          105                    110                  115 | 450 |
| aag ctc ctt gac aac tgg gac agc gtg acc tcc acc ttc agc aag ctg<br>Lys Leu Leu Asp Asn Trp Asp Ser Val Thr Ser Thr Phe Ser Lys Leu<br>          120                    125                  130 | 498 |
| cgc gaa cag ctc ggc cct gtg acc cag gag ttc tgg gat aac ctg gaa<br>Arg Glu Gln Leu Gly Pro Val Thr Gln Glu Phe Trp Asp Asn Leu Glu<br>      135                    140                  145 | 546 |
| aag gag aca gag ggc ctg agg cag gag atg agc aag gat ctg gag gag<br>Lys Glu Thr Glu Gly Leu Arg Gln Glu Met Ser Lys Asp Leu Glu Glu<br>150                  155                    160                165 | 594 |
| gtg aag gcc aag gtg cag ccc tac ctg gac gac ttc cag aag aag tgg<br>Val Lys Ala Lys Val Gln Pro Tyr Leu Asp Asp Phe Gln Lys Lys Trp<br>              170                    175                  180 | 642 |
| cag gag gag atg gag ctc tac cgc cag aag gtg gag ccg ctg cgc gca<br>Gln Glu Glu Met Glu Leu Tyr Arg Gln Lys Val Glu Pro Leu Arg Ala<br>                  185                    190                195 | 690 |
| gag ctc caa gag ggc gcg cgc cag aag ctg cac gag ctg caa gag aag<br>Glu Leu Gln Glu Gly Ala Arg Gln Lys Leu His Glu Leu Gln Glu Lys<br>          200                    205                  210 | 738 |
| ctg agc cca ctg ggc gag gag atg cgc gac cgc gcg cgc gcc cat gtg<br>Leu Ser Pro Leu Gly Glu Glu Met Arg Asp Arg Ala Arg Ala His Val<br>      215                    220                  225 | 786 |
| gac gcg ctg cgc acg cat ctg gcc ccc tac agc gac gag ctg cgc cag<br>Asp Ala Leu Arg Thr His Leu Ala Pro Tyr Ser Asp Glu Leu Arg Gln<br>230                  235                    240                245 | 834 |
| cgc ttg gcc gcg cgc ctt gag gct ctc aag gag aac ggc ggc gcc aga<br>Arg Leu Ala Ala Arg Leu Glu Ala Leu Lys Glu Asn Gly Gly Ala Arg<br>              250                    255                  260 | 882 |
| ctg gcc gag tac cac gcc aag gcc acc gag cat ctg agc acg ctc agc<br>Leu Ala Glu Tyr His Ala Lys Ala Thr Glu His Leu Ser Thr Leu Ser<br>                  265                    270                275 | 930 |
| gag aag gcc aag ccc gcg ctc gag gac ctc cgc caa ggc ctg ctg ccc<br>Glu Lys Ala Lys Pro Ala Leu Glu Asp Leu Arg Gln Gly Leu Leu Pro<br>          280                    285                  290 | 978 |
| gtg ctg gag agc ttc aag gtc agc ttc ctg agc gct ctc gag gag tac<br>Val Leu Glu Ser Phe Lys Val Ser Phe Leu Ser Ala Leu Glu Glu Tyr<br>295                  300                    305 | 1026 |
| act aag aag ctc aac acc cag taataagctt gaattccgat ccggctgcta<br>Thr Lys Lys Leu Asn Thr Gln<br>310                  315 | 1077 |

```
acaaagcccg aaaggaagct gagttggctg cctgccaccg ctgagctgag caataactag   1137
cataacccct ctgccaccgc tgtggggcct ctaaacgggt cttgagggt ttttttgctga   1197 aaggaggaac tatatccgat                                              1217
```

<210> SEQ ID NO 54
<211> LENGTH: 316
<212> TYPE: PRT
<213> ORGANISM: Artificial Sequence
<220> FEATURE:
<223> OTHER INFORMATION: pT7H6 Trip-A-Apo A1 K9A K15A - AmpR plasmid

<400> SEQUENCE: 54

```
Met Gly Ser His His His His His His Gly Ser Ile Gln Gly Arg Ser
1               5                   10                  15

Pro Gly Thr Glu Pro Pro Thr Gln Lys Pro Lys Ala Ile Val Asn Ala
            20                  25                  30

Lys Ala Asp Val Val Asn Thr Lys Met Phe Glu Glu Leu Lys Ser Arg
        35                  40                  45

Leu Asp Thr Leu Ala Gln Glu Val Ala Leu Leu Lys Glu Gln Gln Ala
    50                  55                  60

Leu Gln Thr Val Ser Leu Lys Gly Ser Asp Glu Pro Pro Gln Ser Pro
65                  70                  75                  80

Trp Asp Arg Val Lys Asp Leu Ala Thr Val Tyr Val Asp Val Leu Lys
                85                  90                  95

Asp Ser Gly Arg Asp Tyr Val Ser Gln Phe Glu Gly Ser Ala Leu Gly
            100                 105                 110

Lys Gln Leu Asn Leu Lys Leu Leu Asp Asn Trp Asp Ser Val Thr Ser
        115                 120                 125

Thr Phe Ser Lys Leu Arg Glu Gln Leu Gly Pro Val Thr Gln Glu Phe
    130                 135                 140

Trp Asp Asn Leu Glu Lys Glu Thr Glu Gly Leu Arg Gln Glu Met Ser
145                 150                 155                 160

Lys Asp Leu Glu Glu Val Lys Ala Lys Val Gln Pro Tyr Leu Asp Asp
                165                 170                 175

Phe Gln Lys Lys Trp Gln Glu Glu Met Glu Leu Tyr Arg Gln Lys Val
            180                 185                 190

Glu Pro Leu Arg Ala Glu Leu Gln Glu Gly Ala Arg Gln Lys Leu His
        195                 200                 205

Glu Leu Gln Glu Lys Leu Ser Pro Leu Gly Glu Glu Met Arg Asp Arg
    210                 215                 220

Ala Arg Ala His Val Asp Ala Leu Arg Thr His Leu Ala Pro Tyr Ser
225                 230                 235                 240

Asp Glu Leu Arg Gln Arg Leu Ala Ala Arg Leu Glu Ala Leu Lys Glu
                245                 250                 255

Asn Gly Gly Ala Arg Leu Ala Glu Tyr His Ala Lys Ala Thr Glu His
            260                 265                 270

Leu Ser Thr Leu Ser Glu Lys Ala Lys Pro Ala Leu Glu Asp Leu Arg
        275                 280                 285

Gln Gly Leu Leu Pro Val Leu Glu Ser Phe Lys Val Ser Phe Leu Ser
    290                 295                 300

Ala Leu Glu Glu Tyr Thr Lys Lys Leu Asn Thr Gln
305                 310                 315
```

<210> SEQ ID NO 55
<211> LENGTH: 1238
<212> TYPE: DNA
<213> ORGANISM: Artificial Sequence
<220> FEATURE:
<223> OTHER INFORMATION: pT7H6 Trip-A-Fn-Apo A1 - AmpR plasmid
<221> NAME/KEY: CDS
<222> LOCATION: (100)..(1068)
<223> OTHER INFORMATION:

<400> SEQUENCE: 55

```
gatctcgatc ccgcgaaatt aatacgatac actataggga gaccacaacg gtttccctct      60
agaaataatt ttgtttaact ttaagaagga gatatacat atg gga tcg cat cac       114
                                            Met Gly Ser His His
                                            1               5 cat cac cat cac ggt agt ggt agt gga tca atc cag ggt aga tct cct      162
His His His His Gly Ser Gly Ser Gly Ser Ile Gln Gly Arg Ser Pro
             10                  15                  20 ggt acc gag cca cca acc cag aag ccc aag aag att gta aat gcc aag      210
Gly Thr Glu Pro Pro Thr Gln Lys Pro Lys Lys Ile Val Asn Ala Lys
         25                  30                  35 aaa gat gtt gtg aac aca aag atg ttt gag gag ctc aag agc cgt ctg      258
Lys Asp Val Val Asn Thr Lys Met Phe Glu Glu Leu Lys Ser Arg Leu
     40                  45                  50 gac acc ctg gcc cag gag gtg gcc ctg ctg aag gag cag cag gcc ctg      306
Asp Thr Leu Ala Gln Glu Val Ala Leu Leu Lys Glu Gln Gln Ala Leu
 55                  60                  65 cag acg gtc tcc ctg aag gga tcc tcg ggt cat gat gaa ccc ccc cag      354
Gln Thr Val Ser Leu Lys Gly Ser Ser Gly His Asp Glu Pro Pro Gln
 70                  75                  80                  85 agc ccc tgg gat cga gtg aag gac ctg gcc act gtg tac gtg gat gtg      402
Ser Pro Trp Asp Arg Val Lys Asp Leu Ala Thr Val Tyr Val Asp Val
                 90                  95                 100 ctc aaa gac agc ggc aga gac tat gtg tcc cag ttt gaa ggc tcc gcc      450
Leu Lys Asp Ser Gly Arg Asp Tyr Val Ser Gln Phe Glu Gly Ser Ala
            105                 110                 115 ttg gga aaa cag cta aac cta aag ctc ctt gac aac tgg gac agc gtg      498
Leu Gly Lys Gln Leu Asn Leu Lys Leu Leu Asp Asn Trp Asp Ser Val
        120                 125                 130 acc tcc acc ttc agc aag ctg cgc gaa cag ctc ggc cct gtg acc cag      546
Thr Ser Thr Phe Ser Lys Leu Arg Glu Gln Leu Gly Pro Val Thr Gln
    135                 140                 145 gag ttc tgg gat aac ctg gaa aag gag aca gag ggc ctg agg cag gag      594
Glu Phe Trp Asp Asn Leu Glu Lys Glu Thr Glu Gly Leu Arg Gln Glu
150                 155                 160                 165 atg agc aag gat ctg gag gag gtg aag gcc aag gtg cag ccc tac ctg      642
Met Ser Lys Asp Leu Glu Glu Val Lys Ala Lys Val Gln Pro Tyr Leu
                170                 175                 180 gac gac ttc cag aag aag tgg cag gag gag atg gag ctc tac cgc cag      690
Asp Asp Phe Gln Lys Lys Trp Gln Glu Glu Met Glu Leu Tyr Arg Gln
            185                 190                 195 aag gtg gag ccg ctg cgc gca gag ctc caa gag ggc gcg cgc cag aag      738
Lys Val Glu Pro Leu Arg Ala Glu Leu Gln Glu Gly Ala Arg Gln Lys
        200                 205                 210 ctg cac gag ctg caa gag aag ctg agc cca ctg ggc gag gag atg cgc      786
Leu His Glu Leu Gln Glu Lys Leu Ser Pro Leu Gly Glu Glu Met Arg
    215                 220                 225 gac cgc gcg cgc gcc cat gtg gac gcg ctg cgc acg cat ctg gcc ccc      834
Asp Arg Ala Arg Ala His Val Asp Ala Leu Arg Thr His Leu Ala Pro
230                 235                 240                 245
```

```
tac agc gac gag ctg cgc cag cgc ttg gcc gcg cgc ctt gag gct ctc        882
Tyr Ser Asp Glu Leu Arg Gln Arg Leu Ala Ala Arg Leu Glu Ala Leu
            250                 255                 260 aag gag aac ggc ggc gcc aga ctg gcc gag tac cac gcc aag gcc acc        930
Lys Glu Asn Gly Gly Ala Arg Leu Ala Glu Tyr His Ala Lys Ala Thr
        265                 270                 275 gag cat ctg agc acg ctc agc gag aag gcc aag ccc gcg ctc gag gac        978
Glu His Leu Ser Thr Leu Ser Glu Lys Ala Lys Pro Ala Leu Glu Asp
    280                 285                 290 ctc cgc caa ggc ctg ctg ccc gtg ctg gag agc ttc aag gtc agc ttc       1026
Leu Arg Gln Gly Leu Leu Pro Val Leu Glu Ser Phe Lys Val Ser Phe
295                 300                 305 ctg agc gct ctc gag gag tac act aag aag ctc aac acc cag                1068
Leu Ser Ala Leu Glu Glu Tyr Thr Lys Lys Leu Asn Thr Gln
310                 315                 320 taataagctt gaattccgat ccggctgcta acaaagcccg aaaggaagct gagttggctg     1128
cctgccaccg ctgagctgag caataactag cataaccct ctgccaccgc tgtgggcct      1188 ctaaacgggt cttgaggggt tttttgctga aggaggaac tatatccgat                 1238

<210> SEQ ID NO 56
<211> LENGTH: 323
<212> TYPE: PRT
<213> ORGANISM: Artificial Sequence
<220> FEATURE:
<223> OTHER INFORMATION: pT7H6 Trip-A-Fn-Apo A1 - AmpR plasmid

<400> SEQUENCE: 56

Met Gly Ser His His His His His His Gly Ser Gly Ser Gly Ser Ile
1               5                   10                  15

Gln Gly Arg Ser Pro Gly Thr Glu Pro Pro Thr Gln Lys Pro Lys Lys
            20                  25                  30

Ile Val Asn Ala Lys Lys Asp Val Val Asn Thr Lys Met Phe Glu Glu
        35                  40                  45

Leu Lys Ser Arg Leu Asp Thr Leu Ala Gln Glu Val Ala Leu Leu Lys
    50                  55                  60

Glu Gln Gln Ala Leu Gln Thr Val Ser Leu Lys Gly Ser Ser Gly His
65                  70                  75                  80

Asp Glu Pro Pro Gln Ser Pro Trp Asp Arg Val Lys Asp Leu Ala Thr
                85                  90                  95

Val Tyr Val Asp Val Leu Lys Asp Ser Gly Arg Asp Tyr Val Ser Gln
            100                 105                 110

Phe Glu Gly Ser Ala Leu Gly Lys Gln Leu Asn Leu Lys Leu Leu Asp
        115                 120                 125

Asn Trp Asp Ser Val Thr Ser Thr Phe Ser Lys Leu Arg Glu Gln Leu
    130                 135                 140

Gly Pro Val Thr Gln Glu Phe Trp Asp Asn Leu Glu Lys Glu Thr Glu
145                 150                 155                 160

Gly Leu Arg Gln Glu Met Ser Lys Asp Leu Glu Glu Val Lys Ala Lys
                165                 170                 175

Val Gln Pro Tyr Leu Asp Asp Phe Gln Lys Lys Trp Gln Glu Glu Met
            180                 185                 190

Glu Leu Tyr Arg Gln Lys Val Glu Pro Leu Arg Ala Glu Leu Gln Glu
        195                 200                 205

Gly Ala Arg Gln Lys Leu His Glu Leu Gln Glu Lys Leu Ser Pro Leu
    210                 215                 220
```

-continued

```
Gly Glu Glu Met Arg Asp Arg Ala Arg Ala His Val Asp Ala Leu Arg
225                 230                 235                 240

Thr His Leu Ala Pro Tyr Ser Asp Glu Leu Arg Gln Arg Leu Ala Ala
                245                 250                 255

Arg Leu Glu Ala Leu Lys Glu Asn Gly Gly Ala Arg Leu Ala Glu Tyr
            260                 265                 270

His Ala Lys Ala Thr Glu His Leu Ser Thr Leu Ser Glu Lys Ala Lys
        275                 280                 285

Pro Ala Leu Glu Asp Leu Arg Gln Gly Leu Leu Pro Val Leu Glu Ser
    290                 295                 300

Phe Lys Val Ser Phe Leu Ser Ala Leu Glu Glu Tyr Thr Lys Lys Leu
305                 310                 315                 320

Asn Thr Gln
```

<210> SEQ ID NO 57
<211> LENGTH: 1238
<212> TYPE: DNA
<213> ORGANISM: Artificial Sequence
<220> FEATURE:
<223> OTHER INFORMATION: pT7H6 Trip-A-Fn-Apo A1-final - AmpR plasmid
<221> NAME/KEY: CDS
<222> LOCATION: (100)..(1068)
<223> OTHER INFORMATION:

<400> SEQUENCE: 57

```
gatctcgatc ccgcgaaatt aatacgatac actataggga gaccacaacg gtttccctct      60
agaaataatt ttgtttaact ttaagaagga gatatacat atg gga tcg cat cac        114
                                            Met Gly Ser His His
                                              1               5 cat cac cat cac ggt agt ggt agt gga tca atc cag ggt aga tct cct       162
His His His His Gly Ser Gly Ser Gly Ser Ile Gln Gly Arg Ser Pro
             10                  15                  20 ggt acc gag cca cca acc cag aag ccc aag aag att gta aat gcc aag       210
Gly Thr Glu Pro Pro Thr Gln Lys Pro Lys Lys Ile Val Asn Ala Lys
         25                  30                  35 aaa gat gtt gtg aac aca aag atg ttt gag gag ctc aag agc cgt ctg       258
Lys Asp Val Val Asn Thr Lys Met Phe Glu Glu Leu Lys Ser Arg Leu
     40                  45                  50 gac acc ctg gcc cag gag gtg gcc ctg ctg aag gag cag cag gcc ctg       306
Asp Thr Leu Ala Gln Glu Val Ala Leu Leu Lys Glu Gln Gln Ala Leu
 55                  60                  65 cag acg gtc tcc ctg aag gga acc tcg ggt cag gat gaa ccc ccc cag       354
Gln Thr Val Ser Leu Lys Gly Thr Ser Gly Gln Asp Glu Pro Pro Gln
 70                  75                  80                  85 agc ccc tgg gat cga gtg aag gac ctg gcc act gtg tac gtg gat gtg       402
Ser Pro Trp Asp Arg Val Lys Asp Leu Ala Thr Val Tyr Val Asp Val
                 90                  95                 100 ctc aaa gac agc ggc aga gac tat gtg tcc cag ttt gaa ggc tcc gcc       450
Leu Lys Asp Ser Gly Arg Asp Tyr Val Ser Gln Phe Glu Gly Ser Ala
            105                 110                 115 ttg gga aaa cag cta aac cta aag ctc ctt gac aac tgg gac agc gtg       498
Leu Gly Lys Gln Leu Asn Leu Lys Leu Leu Asp Asn Trp Asp Ser Val
        120                 125                 130 acc tcc acc ttc agc aag ctg cgc gaa cag ctc ggc cct gtg acc cag       546
Thr Ser Thr Phe Ser Lys Leu Arg Glu Gln Leu Gly Pro Val Thr Gln
    135                 140                 145 gag ttc tgg gat aac ctg gaa aag gag aca gag ggc ctg agg cag gag       594
Glu Phe Trp Asp Asn Leu Glu Lys Glu Thr Glu Gly Leu Arg Gln Glu
150                 155                 160                 165
```

```
atg agc aag gat ctg gag gag gtg aag gcc aag gtg cag ccc tac ctg     642
Met Ser Lys Asp Leu Glu Glu Val Lys Ala Lys Val Gln Pro Tyr Leu
            170                 175                 180 gac gac ttc cag aag aag tgg cag gag gag atg gag ctc tac cgc cag     690
Asp Asp Phe Gln Lys Lys Trp Gln Glu Glu Met Glu Leu Tyr Arg Gln
                185                 190                 195 aag gtg gag ccg ctg cgc gca gag ctc caa gag ggc gcg cgc cag aag     738
Lys Val Glu Pro Leu Arg Ala Glu Leu Gln Glu Gly Ala Arg Gln Lys
            200                 205                 210 ctg cac gag ctg caa gag aag ctg agc cca ctg ggc gag gag atg cgc     786
Leu His Glu Leu Gln Glu Lys Leu Ser Pro Leu Gly Glu Glu Met Arg
            215                 220                 225 gac cgc gcg cgc gcc cat gtg gac gcg ctg cgc acg cat ctg gcc ccc     834
Asp Arg Ala Arg Ala His Val Asp Ala Leu Arg Thr His Leu Ala Pro
230                 235                 240                 245 tac agc gac gag ctg cgc cag cgc ttg gcc gcg cgc ctt gag gct ctc     882
Tyr Ser Asp Glu Leu Arg Gln Arg Leu Ala Ala Arg Leu Glu Ala Leu
                250                 255                 260 aag gag aac ggc ggc gcc aga ctg gcc gag tac cac gcc aag gcc acc     930
Lys Glu Asn Gly Gly Ala Arg Leu Ala Glu Tyr His Ala Lys Ala Thr
                265                 270                 275 gag cat ctg agc acg ctc agc gag aag gcc aag ccc gcg ctc gag gac     978
Glu His Leu Ser Thr Leu Ser Glu Lys Ala Lys Pro Ala Leu Glu Asp
            280                 285                 290 ctc cgc caa ggc ctg ctg ccc gtg ctg gag agc ttc aag gtc agc ttc    1026
Leu Arg Gln Gly Leu Leu Pro Val Leu Glu Ser Phe Lys Val Ser Phe
295                 300                 305 ctg agc gct ctc gag gag tac act aag aag ctc aac acc cag             1068
Leu Ser Ala Leu Glu Glu Tyr Thr Lys Lys Leu Asn Thr Gln
            310                 315                 320 taataagctt gaattccgat ccggctgcta acaaagcccg aaaggaagct gagttggctg   1128
cctgccaccg ctgagctgag caataactag cataacccct ctgccaccgc tgtggggcct   1188
ctaaacgggt cttgaggggt ttttgctga aaggaggaac tatatccgat               1238

<210> SEQ ID NO 58
<211> LENGTH: 323
<212> TYPE: PRT
<213> ORGANISM: Artificial Sequence
<220> FEATURE:
<223> OTHER INFORMATION: pT7H6 Trip-A-Fn-Apo A1-final - AmpR plasmid

<400> SEQUENCE: 58

Met Gly Ser His His His His His His Gly Ser Gly Ser Gly Ser Ile
1               5                   10                  15

Gln Gly Arg Ser Pro Gly Thr Glu Pro Pro Thr Gln Lys Pro Lys Lys
            20                  25                  30

Ile Val Asn Ala Lys Lys Asp Val Val Asn Thr Lys Met Phe Glu Glu
        35                  40                  45

Leu Lys Ser Arg Leu Asp Thr Leu Ala Gln Glu Val Ala Leu Leu Lys
    50                  55                  60

Glu Gln Gln Ala Leu Gln Thr Val Ser Leu Lys Gly Thr Ser Gly Gln
65                  70                  75                  80

Asp Glu Pro Pro Gln Ser Pro Trp Asp Arg Val Lys Asp Leu Ala Thr
                85                  90                  95

Val Tyr Val Asp Val Leu Lys Asp Ser Gly Arg Asp Tyr Val Ser Gln
            100                 105                 110

Phe Glu Gly Ser Ala Leu Gly Lys Gln Leu Asn Leu Lys Leu Leu Asp
        115                 120                 125
```

```
Asn Trp Asp Ser Val Thr Ser Thr Phe Ser Lys Leu Arg Glu Gln Leu
130                 135                 140

Gly Pro Val Thr Gln Glu Phe Trp Asp Asn Leu Glu Lys Glu Thr Glu
145                 150                 155                 160

Gly Leu Arg Gln Glu Met Ser Lys Asp Leu Glu Glu Val Lys Ala Lys
                165                 170                 175

Val Gln Pro Tyr Leu Asp Asp Phe Gln Lys Lys Trp Gln Glu Glu Met
            180                 185                 190

Glu Leu Tyr Arg Gln Lys Val Glu Pro Leu Arg Ala Glu Leu Gln Glu
        195                 200                 205

Gly Ala Arg Gln Lys Leu His Glu Leu Gln Glu Lys Leu Ser Pro Leu
210                 215                 220

Gly Glu Glu Met Arg Asp Arg Ala Arg Ala His Val Asp Ala Leu Arg
225                 230                 235                 240

Thr His Leu Ala Pro Tyr Ser Asp Glu Leu Arg Gln Arg Leu Ala Ala
                245                 250                 255

Arg Leu Glu Ala Leu Lys Glu Asn Gly Gly Ala Arg Leu Ala Glu Tyr
            260                 265                 270

His Ala Lys Ala Thr Glu His Leu Ser Thr Leu Ser Glu Lys Ala Lys
        275                 280                 285

Pro Ala Leu Glu Asp Leu Arg Gln Gly Leu Leu Pro Val Leu Glu Ser
290                 295                 300

Phe Lys Val Ser Phe Leu Ser Ala Leu Glu Glu Tyr Thr Lys Lys Leu
305                 310                 315                 320

Asn Thr Gln

<210> SEQ ID NO 59
<211> LENGTH: 1238
<212> TYPE: DNA
<213> ORGANISM: Artificial Sequence
<220> FEATURE:
<223> OTHER INFORMATION: pT7H6 Trip-A-Fn-Apo A1 final K9AK15A - AmpR
      plasmid
<221> NAME/KEY: CDS
<222> LOCATION: (100)..(1068)
<223> OTHER INFORMATION:

<400> SEQUENCE: 59
gatctcgatc ccgcgaaatt aatacgatac actatagggga gaccacaacg gtttccctct     60
agaaataatt ttgtttaact ttaagaagga gatatacat atg gga tcg cat cac       114
                                            Met Gly Ser His His
                                             1               5 cat cac cat cac ggt agt ggt agt gga tca atc cag ggt aga tct cct       162
His His His His Gly Ser Gly Ser Gly Ser Ile Gln Gly Arg Ser Pro
             10                  15                  20 ggt acc gag cca cca acc cag aag ccc aag gcg att gta aat gcc aag       210
Gly Thr Glu Pro Pro Thr Gln Lys Pro Lys Ala Ile Val Asn Ala Lys
         25                  30                  35 gca gat gtt gtg aac aca aag atg ttt gag gag ctc aag agc cgt ctg       258
Ala Asp Val Val Asn Thr Lys Met Phe Glu Glu Leu Lys Ser Arg Leu
         40                  45                  50 gac acc ctg gcc cag gag gtg gcc ctg ctg aag gag cag cag gcc ctg       306
Asp Thr Leu Ala Gln Glu Val Ala Leu Leu Lys Glu Gln Gln Ala Leu
     55                  60                  65 cag acg gtc tcc ctg aag gga acc tcg ggt cag gat gaa ccc ccc cag       354
Gln Thr Val Ser Leu Lys Gly Thr Ser Gly Gln Asp Glu Pro Pro Gln
 70                  75                  80                  85
```

```
agc ccc tgg gat cga gtg aag gac ctg gcc act gtg tac gtg gat gtg      402
Ser Pro Trp Asp Arg Val Lys Asp Leu Ala Thr Val Tyr Val Asp Val
             90                  95                 100 ctc aaa gac agc ggc aga gac tat gtg tcc cag ttt gaa ggc tcc gcc      450
Leu Lys Asp Ser Gly Arg Asp Tyr Val Ser Gln Phe Glu Gly Ser Ala
            105                 110                 115 ttg gga aaa cag cta aac cta aag ctc ctt gac aac tgg gac agc gtg      498
Leu Gly Lys Gln Leu Asn Leu Lys Leu Leu Asp Asn Trp Asp Ser Val
        120                 125                 130 acc tcc acc ttc agc aag ctg cgc gaa cag ctc ggc cct gtg acc cag      546
Thr Ser Thr Phe Ser Lys Leu Arg Glu Gln Leu Gly Pro Val Thr Gln
        135                 140                 145 gag ttc tgg gat aac ctg gaa aag gag aca gag ggc ctg agg cag gag      594
Glu Phe Trp Asp Asn Leu Glu Lys Glu Thr Glu Gly Leu Arg Gln Glu
150                 155                 160                 165 atg agc aag gat ctg gag gag gtg aag gcc aag gtg cag ccc tac ctg      642
Met Ser Lys Asp Leu Glu Glu Val Lys Ala Lys Val Gln Pro Tyr Leu
                170                 175                 180 gac gac ttc cag aag aag tgg cag gag gag atg gag ctc tac cgc cag      690
Asp Asp Phe Gln Lys Lys Trp Gln Glu Glu Met Glu Leu Tyr Arg Gln
            185                 190                 195 aag gtg gag ccg ctg cgc gca gag ctc caa gag ggc gcg cgc cag aag      738
Lys Val Glu Pro Leu Arg Ala Glu Leu Gln Glu Gly Ala Arg Gln Lys
        200                 205                 210 ctg cac gag ctg caa gag aag ctg agc cca ctg ggc gag gag atg cgc      786
Leu His Glu Leu Gln Glu Lys Leu Ser Pro Leu Gly Glu Glu Met Arg
        215                 220                 225 gac cgc gcg cgc gcc cat gtg gac gcg ctg cgc acg cat ctg gcc ccc      834
Asp Arg Ala Arg Ala His Val Asp Ala Leu Arg Thr His Leu Ala Pro
230                 235                 240                 245 tac agc gac gag ctg cgc cag cgc ttg gcc gcg cgc ctt gag gct ctc      882
Tyr Ser Asp Glu Leu Arg Gln Arg Leu Ala Ala Arg Leu Glu Ala Leu
                250                 255                 260 aag gag aac ggc ggc gcc aga ctg gcc gag tac cac gcc aag gcc acc      930
Lys Glu Asn Gly Gly Ala Arg Leu Ala Glu Tyr His Ala Lys Ala Thr
            265                 270                 275 gag cat ctg agc acg ctc agc gag aag gcc aag ccc gcg ctc gag gac      978
Glu His Leu Ser Thr Leu Ser Glu Lys Ala Lys Pro Ala Leu Glu Asp
        280                 285                 290 ctc cgc caa ggc ctg ctg ccc gtg ctg gag agc ttc aag gtc agc ttc     1026
Leu Arg Gln Gly Leu Leu Pro Val Leu Glu Ser Phe Lys Val Ser Phe
        295                 300                 305 ctg agc gct ctc gag gag tac act aag aag ctc aac acc cag              1068
Leu Ser Ala Leu Glu Glu Tyr Thr Lys Lys Leu Asn Thr Gln
310                 315                 320 taataagctt gaattccgat ccggctgcta acaaagcccg aaaggaagct gagttggctg   1128
cctgccaccg ctgagctgag caataactag cataacccct ctgccaccgc tgtgggggcct  1188 ctaaacgggt cttgaggggt ttttgctga aggaggaac tatatccgat               1238

<210> SEQ ID NO 60
<211> LENGTH: 323
<212> TYPE: PRT
<213> ORGANISM: Artificial Sequence
<220> FEATURE:
<223> OTHER INFORMATION: pT7H6 Trip-A-Fn-Apo A1 final K9AK15A - AmpR
      plasmid
```

```
<400> SEQUENCE: 60

Met Gly Ser His His His His His Gly Ser Gly Ser Gly Ser Ile
1               5                   10                  15

Gln Gly Arg Ser Pro Gly Thr Glu Pro Pro Thr Gln Lys Pro Lys Ala
            20                  25                  30

Ile Val Asn Ala Lys Ala Asp Val Val Asn Thr Lys Met Phe Glu Glu
            35                  40                  45

Leu Lys Ser Arg Leu Asp Thr Leu Ala Gln Glu Val Ala Leu Leu Lys
50                  55                      60

Glu Gln Gln Ala Leu Gln Thr Val Ser Leu Lys Gly Thr Ser Gly Gln
65                  70                  75                  80

Asp Glu Pro Pro Gln Ser Pro Trp Asp Arg Val Lys Asp Leu Ala Thr
                85                  90                  95

Val Tyr Val Asp Val Leu Lys Asp Ser Gly Arg Asp Tyr Val Ser Gln
                100                 105                 110

Phe Glu Gly Ser Ala Leu Gly Lys Gln Leu Asn Leu Lys Leu Leu Asp
            115                 120                 125

Asn Trp Asp Ser Val Thr Ser Thr Phe Ser Lys Leu Arg Glu Gln Leu
130                 135                 140

Gly Pro Val Thr Gln Glu Phe Trp Asp Asn Leu Glu Lys Glu Thr Glu
145                 150                 155                 160

Gly Leu Arg Gln Glu Met Ser Lys Asp Leu Glu Glu Val Lys Ala Lys
                165                 170                 175

Val Gln Pro Tyr Leu Asp Asp Phe Gln Lys Lys Trp Gln Glu Glu Met
            180                 185                 190

Glu Leu Tyr Arg Gln Lys Val Glu Pro Leu Arg Ala Glu Leu Gln Glu
            195                 200                 205

Gly Ala Arg Gln Lys Leu His Glu Leu Gln Glu Lys Leu Ser Pro Leu
210                 215                 220

Gly Glu Glu Met Arg Asp Arg Ala Arg Ala His Val Asp Ala Leu Arg
225                 230                 235                 240

Thr His Leu Ala Pro Tyr Ser Asp Glu Leu Arg Gln Arg Leu Ala Ala
                245                 250                 255

Arg Leu Glu Ala Leu Lys Glu Asn Gly Gly Ala Arg Leu Ala Glu Tyr
            260                 265                 270

His Ala Lys Ala Thr Glu His Leu Ser Thr Leu Ser Glu Lys Ala Lys
            275                 280                 285

Pro Ala Leu Glu Asp Leu Arg Gln Gly Leu Leu Pro Val Leu Glu Ser
            290                 295                 300

Phe Lys Val Ser Phe Leu Ser Ala Leu Glu Glu Tyr Thr Lys Lys Leu
305                 310                 315                 320

Asn Thr Gln

<210> SEQ ID NO 61
<211> LENGTH: 1241
<212> TYPE: DNA
<213> ORGANISM: Artificial Sequence
<220> FEATURE:
<223> OTHER INFORMATION: pT7H6 (GS)3 Trip-A-Tn-Apo A1 AmpR plasmid
<221> NAME/KEY: CDS
<222> LOCATION: (100)..(1071)
<223> OTHER INFORMATION:
```

-continued

```
<400> SEQUENCE: 61
gatctcgatc cgcgaaatt aatacgatac actatagggga gaccacaacg gtttccctct        60
agaaataatt tgtttaact ttaagaagga gatatacat atg gga tcg cat cac          114
                                           Met Gly Ser His His
                                            1               5 cat cac cat cac ggt agt ggt agt gga tca atc cag ggt aga tct cct        162
His His His His Gly Ser Gly Ser Gly Ser Ile Gln Gly Arg Ser Pro
             10                  15                  20 ggt acc gag cca cca acc cag aag ccc aag aag att gta aat gcc aag        210
Gly Thr Glu Pro Pro Thr Gln Lys Pro Lys Lys Ile Val Asn Ala Lys
         25                  30                  35 aaa gat gtt gtg aac aca aag atg ttt gag gag ctc aag agc cgt ctg        258
Lys Asp Val Val Asn Thr Lys Met Phe Glu Glu Leu Lys Ser Arg Leu
     40                  45                  50 gac acc ctg gcc cag gag gtg gcc ctg ctg aag gag cag cag gcc ctg        306
Asp Thr Leu Ala Gln Glu Val Ala Leu Leu Lys Glu Gln Gln Ala Leu
 55                  60                  65 cag acg gtc tcc ctg aag gga tcc aag gtg cac atg aag gaa ccc ccc        354
Gln Thr Val Ser Leu Lys Gly Ser Lys Val His Met Lys Glu Pro Pro
70                  75                  80                  85 cag agc ccc tgg gat cga gtg aag gac ctg gcc act gtg tac gtg gat        402
Gln Ser Pro Trp Asp Arg Val Lys Asp Leu Ala Thr Val Tyr Val Asp
                 90                  95                 100 gtg ctc aaa gac agc ggc aga gac tat gtg tcc cag ttt gaa ggc tcc        450
Val Leu Lys Asp Ser Gly Arg Asp Tyr Val Ser Gln Phe Glu Gly Ser
            105                 110                 115 gcc ttg gga aaa cag cta aac cta aag ctc ctt gac aac tgg gac agc        498
Ala Leu Gly Lys Gln Leu Asn Leu Lys Leu Leu Asp Asn Trp Asp Ser
        120                 125                 130 gtg acc tcc acc ttc agc aag ctg cgc gaa cag ctc ggc cct gtg acc        546
Val Thr Ser Thr Phe Ser Lys Leu Arg Glu Gln Leu Gly Pro Val Thr
    135                 140                 145 cag gag ttc tgg gat aac ctg gaa aag gag aca gag ggc ctg agg cag        594
Gln Glu Phe Trp Asp Asn Leu Glu Lys Glu Thr Glu Gly Leu Arg Gln
150                 155                 160                 165 gag atg agc aag gat ctg gag gag gtg aag gcc aag gtg cag ccc tac        642
Glu Met Ser Lys Asp Leu Glu Glu Val Lys Ala Lys Val Gln Pro Tyr
                170                 175                 180 ctg gac gac ttc cag aag aag tgg cag gag gag atg gag ctc tac cgc        690
Leu Asp Asp Phe Gln Lys Lys Trp Gln Glu Glu Met Glu Leu Tyr Arg
            185                 190                 195 cag aag gtg gag ccg ctg cgc gca gag ctc caa gag ggc gcg cgc cag        738
Gln Lys Val Glu Pro Leu Arg Ala Glu Leu Gln Glu Gly Ala Arg Gln
        200                 205                 210 aag ctg cac gag ctg caa gag aag ctg agc cca ctg ggc gag gag atg        786
Lys Leu His Glu Leu Gln Glu Lys Leu Ser Pro Leu Gly Glu Glu Met
215                 220                 225 cgc gac cgc gcg cgc gcc cat gtg gac gcg ctg cgc acg cat ctg gcc        834
Arg Asp Arg Ala Arg Ala His Val Asp Ala Leu Arg Thr His Leu Ala
230                 235                 240                 245 ccc tac agc gac gag ctg cgc cag cgc ttg gcc gcg cgc ctt gag gct        882
Pro Tyr Ser Asp Glu Leu Arg Gln Arg Leu Ala Ala Arg Leu Glu Ala
                250                 255                 260 ctc aag gag aac ggc ggc gcc aga ctg gcc gag tac cac gcc aag gcc        930
Leu Lys Glu Asn Gly Gly Ala Arg Leu Ala Glu Tyr His Ala Lys Ala
            265                 270                 275 acc gag cat ctg agc acg ctc agc gag aag gcc aag ccc gcg ctc gag        978
Thr Glu His Leu Ser Thr Leu Ser Glu Lys Ala Lys Pro Ala Leu Glu
        280                 285                 290
```

-continued

```
gac ctc cgc caa ggc ctg ctg ccc gtg ctg gag agc ttc aag gtc agc    1026
Asp Leu Arg Gln Gly Leu Leu Pro Val Leu Glu Ser Phe Lys Val Ser
    295                 300                 305 ttc ctg agc gct ctc gag gag tac act aag aag ctc aac acc cag        1071
Phe Leu Ser Ala Leu Glu Glu Tyr Thr Lys Lys Leu Asn Thr Gln
310                 315                 320 taataagctt gaattccgat ccggctgcta acaaagcccg aaaggaagct gagttggctg   1131
cctgccaccg ctgagctgag caataactag cataacccct ctgccaccgc tgtggggcct   1191
ctaaacgggt cttgaggggt tttttgctga aggaggaac tatatccgat              1241
```

<210> SEQ ID NO 62
<211> LENGTH: 324
<212> TYPE: PRT
<213> ORGANISM: Artificial Sequence
<220> FEATURE:
<223> OTHER INFORMATION: pT7H6 (GS)3 Trip-A-Tn-Apo A1 AmpR plasmid

<400> SEQUENCE: 62

```
Met Gly Ser His His His His His Gly Ser Gly Ser Gly Ser Ile
1               5                   10                  15

Gln Gly Arg Ser Pro Gly Thr Glu Pro Thr Gln Lys Pro Lys Lys
                20                  25                  30

Ile Val Asn Ala Lys Lys Asp Val Val Asn Thr Lys Met Phe Glu Glu
            35                  40                  45

Leu Lys Ser Arg Leu Asp Thr Leu Ala Gln Glu Val Ala Leu Leu Lys
50                  55                  60

Glu Gln Gln Ala Leu Gln Thr Val Ser Leu Lys Gly Ser Lys Val His
65                  70                  75                  80

Met Lys Glu Pro Pro Gln Ser Pro Trp Asp Arg Val Lys Asp Leu Ala
                85                  90                  95

Thr Val Tyr Val Asp Val Leu Lys Asp Ser Gly Arg Asp Tyr Val Ser
            100                 105                 110

Gln Phe Glu Gly Ser Ala Leu Gly Lys Gln Leu Asn Leu Lys Leu Leu
        115                 120                 125

Asp Asn Trp Asp Ser Val Thr Ser Thr Phe Ser Lys Leu Arg Glu Gln
    130                 135                 140

Leu Gly Pro Val Thr Gln Glu Phe Trp Asp Asn Leu Glu Lys Glu Thr
145                 150                 155                 160

Glu Gly Leu Arg Gln Glu Met Ser Lys Asp Leu Glu Glu Val Lys Ala
                165                 170                 175

Lys Val Gln Pro Tyr Leu Asp Asp Phe Gln Lys Lys Trp Gln Glu Glu
            180                 185                 190

Met Glu Leu Tyr Arg Gln Lys Val Glu Pro Leu Arg Ala Glu Leu Gln
        195                 200                 205

Glu Gly Ala Arg Gln Lys Leu His Glu Leu Gln Glu Lys Leu Ser Pro
    210                 215                 220

Leu Gly Glu Glu Met Arg Asp Arg Ala Arg Ala His Val Asp Ala Leu
225                 230                 235                 240

Arg Thr His Leu Ala Pro Tyr Ser Asp Glu Leu Arg Gln Arg Leu Ala
                245                 250                 255

Ala Arg Leu Glu Ala Leu Lys Glu Asn Gly Gly Ala Arg Leu Ala Glu
            260                 265                 270

Tyr His Ala Lys Ala Thr Glu His Leu Ser Thr Leu Ser Glu Lys Ala
        275                 280                 285
```

```
Lys Pro Ala Leu Glu Asp Leu Arg Gln Gly Leu Leu Pro Val Leu Glu
    290                 295                 300

Ser Phe Lys Val Ser Phe Leu Ser Ala Leu Glu Glu Tyr Thr Lys Lys
305                 310                 315                 320

Leu Asn Thr Gln

<210> SEQ ID NO 63
<211> LENGTH: 1241
<212> TYPE: DNA
<213> ORGANISM: Artificial Sequence
<220> FEATURE:
<223> OTHER INFORMATION: pT7H6 Trip-A-Tn-Apo A1-final - AmpR plasmid
<221> NAME/KEY: CDS
<222> LOCATION: (100)..(1071)
<223> OTHER INFORMATION:

<400> SEQUENCE: 63
gatctcgatc ccgcgaaatt aatacgatac actataggga gaccacaacg gtttccctct      60
agaaataatt ttgtttaact ttaagaagga gatatacat atg gga tcg cat cac       114
                                            Met Gly Ser His His
                                              1               5 cat cac cat cac ggt agt ggt agt gga tca atc cag ggt aga tct cct      162
His His His His Gly Ser Gly Ser Gly Ser Ile Gln Gly Arg Ser Pro
             10                  15                  20 ggt acc gag cca cca acc cag aag ccc aag aag att gta aat gcc aag      210
Gly Thr Glu Pro Pro Thr Gln Lys Pro Lys Lys Ile Val Asn Ala Lys
         25                  30                  35 aaa gat gtt gtg aac aca aag atg ttt gag gag ctc aag agc cgt ctg      258
Lys Asp Val Val Asn Thr Lys Met Phe Glu Glu Leu Lys Ser Arg Leu
     40                  45                  50 gac acc ctg gcc cag gag gtg gcc ctg ctg aag gag cag cag gcc ctg      306
Asp Thr Leu Ala Gln Glu Val Ala Leu Leu Lys Glu Gln Gln Ala Leu
 55                  60                  65 cag acg gtc tcc ctg aag gga acc aag gtg cac atg aag gaa ccc ccc      354
Gln Thr Val Ser Leu Lys Gly Thr Lys Val His Met Lys Glu Pro Pro
 70                  75                  80                  85 cag agc ccc tgg gat cga gtg aag gac ctg gcc act gtg tac gtg gat      402
Gln Ser Pro Trp Asp Arg Val Lys Asp Leu Ala Thr Val Tyr Val Asp
             90                  95                 100 gtg ctc aaa gac agc ggc aga gac tat gtg tcc cag ttt gaa ggc tcc      450
Val Leu Lys Asp Ser Gly Arg Asp Tyr Val Ser Gln Phe Glu Gly Ser
        105                 110                 115 gcc ttg gga aaa cag cta aac cta aag ctc ctt gac aac tgg gac agc      498
Ala Leu Gly Lys Gln Leu Asn Leu Lys Leu Leu Asp Asn Trp Asp Ser
    120                 125                 130 gtg acc tcc acc ttc agc aag ctg cgc gaa cag ctc ggc cct gtg acc      546
Val Thr Ser Thr Phe Ser Lys Leu Arg Glu Gln Leu Gly Pro Val Thr
135                 140                 145 cag gag ttc tgg gat aac ctg gaa aag gag aca gag ggc ctg agg cag      594
Gln Glu Phe Trp Asp Asn Leu Glu Lys Glu Thr Glu Gly Leu Arg Gln
150                 155                 160                 165 gag atg agc aag gat ctg gag gag gtg aag gcc aag gtg cag ccc tac      642
Glu Met Ser Lys Asp Leu Glu Glu Val Lys Ala Lys Val Gln Pro Tyr
            170                 175                 180 ctg gac gac ttc cag aag aag tgg cag gag gag atg gag ctc tac cgc      690
Leu Asp Asp Phe Gln Lys Lys Trp Gln Glu Glu Met Glu Leu Tyr Arg
        185                 190                 195 cag aag gtg gag ccg ctg cgc gca gag ctc caa gag ggc gcg cgc cag      738
Gln Lys Val Glu Pro Leu Arg Ala Glu Leu Gln Glu Gly Ala Arg Gln
    200                 205                 210
```

-continued

```
aag ctg cac gag ctg caa gag aag ctg agc cca ctg ggc gag gag atg      786
Lys Leu His Glu Leu Gln Glu Lys Leu Ser Pro Leu Gly Glu Glu Met
215                 220                 225 cgc gac cgc gcg cgc gcc cat gtg gac gcg ctg cgc acg cat ctg gcc      834
Arg Asp Arg Ala Arg Ala His Val Asp Ala Leu Arg Thr His Leu Ala
230                 235                 240                 245 ccc tac agc gac gag ctg cgc cag cgc ttg gcc gcg cgc ctt gag gct      882
Pro Tyr Ser Asp Glu Leu Arg Gln Arg Leu Ala Ala Arg Leu Glu Ala
                250                 255                 260 ctc aag gag aac ggc ggc gcc aga ctg gcc gag tac cac gcc aag gcc      930
Leu Lys Glu Asn Gly Gly Ala Arg Leu Ala Glu Tyr His Ala Lys Ala
            265                 270                 275 acc gag cat ctg agc acg ctc agc gag aag gcc aag ccc gcg ctc gag      978
Thr Glu His Leu Ser Thr Leu Ser Glu Lys Ala Lys Pro Ala Leu Glu
        280                 285                 290 gac ctc cgc caa ggc ctg ctg ccc gtg ctg gag agc ttc aag gtc agc     1026
Asp Leu Arg Gln Gly Leu Leu Pro Val Leu Glu Ser Phe Lys Val Ser
    295                 300                 305 ttc ctg agc gct ctc gag gag tac act aag aag ctc aac acc cag         1071
Phe Leu Ser Ala Leu Glu Glu Tyr Thr Lys Lys Leu Asn Thr Gln
310                 315                 320 taataagctt gaattccgat ccggctgcta acaaagcccg aaaggaagct gagttggctg   1131
cctgccaccg ctgagctgag caataactag cataacccct ctgccaccgc tgtggggcct   1191
ctaaacgggt cttgaggggt tttttgctga aggaggaac tatatccgat               1241

<210> SEQ ID NO 64
<211> LENGTH: 324
<212> TYPE: PRT
<213> ORGANISM: Artificial Sequence
<220> FEATURE:
<223> OTHER INFORMATION: pT7H6 Trip-A-Tn-Apo A1-final - AmpR plasmid

<400> SEQUENCE: 64

Met Gly Ser His His His His His His Gly Ser Gly Ser Gly Ser Ile
1               5                   10                  15

Gln Gly Arg Ser Pro Gly Thr Glu Pro Pro Thr Gln Lys Pro Lys Lys
            20                  25                  30

Ile Val Asn Ala Lys Lys Asp Val Val Asn Thr Lys Met Phe Glu Glu
        35                  40                  45

Leu Lys Ser Arg Leu Asp Thr Leu Ala Gln Glu Val Ala Leu Leu Lys
    50                  55                  60

Glu Gln Gln Ala Leu Gln Thr Val Ser Leu Lys Gly Thr Lys Val His
65                  70                  75                  80

Met Lys Glu Pro Pro Gln Ser Pro Trp Asp Arg Val Lys Asp Leu Ala
                85                  90                  95

Thr Val Tyr Val Asp Val Leu Lys Asp Ser Gly Arg Asp Tyr Val Ser
            100                 105                 110

Gln Phe Glu Gly Ser Ala Leu Gly Lys Gln Leu Asn Leu Lys Leu Leu
        115                 120                 125

Asp Asn Trp Asp Ser Val Thr Ser Thr Phe Ser Lys Leu Arg Glu Gln
    130                 135                 140

Leu Gly Pro Val Thr Gln Glu Phe Trp Asp Asn Leu Glu Lys Glu Thr
145                 150                 155                 160

Glu Gly Leu Arg Gln Glu Met Ser Lys Asp Leu Glu Glu Val Lys Ala
                165                 170                 175

Lys Val Gln Pro Tyr Leu Asp Asp Phe Gln Lys Lys Trp Gln Glu Glu
            180                 185                 190
```

```
Met Glu Leu Tyr Arg Gln Lys Val Glu Pro Leu Arg Ala Glu Leu Gln
        195                 200                 205

Glu Gly Ala Arg Gln Lys Leu His Glu Leu Gln Glu Lys Leu Ser Pro
    210                 215                 220

Leu Gly Glu Glu Met Arg Asp Arg Ala Arg Ala His Val Asp Ala Leu
225                 230                 235                 240

Arg Thr His Leu Ala Pro Tyr Ser Asp Glu Leu Arg Gln Arg Leu Ala
                245                 250                 255

Ala Arg Leu Glu Ala Leu Lys Glu Asn Gly Gly Ala Arg Leu Ala Glu
            260                 265                 270

Tyr His Ala Lys Ala Thr Glu His Leu Ser Thr Leu Ser Glu Lys Ala
        275                 280                 285

Lys Pro Ala Leu Glu Asp Leu Arg Gln Gly Leu Leu Pro Val Leu Glu
    290                 295                 300

Ser Phe Lys Val Ser Phe Leu Ser Ala Leu Glu Glu Tyr Thr Lys Lys
305                 310                 315                 320

Leu Asn Thr Gln
```

<210> SEQ ID NO 65
<211> LENGTH: 1241
<212> TYPE: DNA
<213> ORGANISM: Artificial Sequence
<220> FEATURE:
<223> OTHER INFORMATION: pT7H6 Trip-A-Tn-Apo A1 final K9AK15A - AmpR
      plasmid
<221> NAME/KEY: CDS
<222> LOCATION: (100)..(1071)
<223> OTHER INFORMATION:

<400> SEQUENCE: 65

```
gatctcgatc ccgcgaaatt aatacgatac actatagga gaccacaacg gtttccctct      60
agaaataatt ttgtttaact ttaagaagga gatatacat atg gga tcg cat cac      114
                                             Met Gly Ser His His
                                               1               5 cat cac cat cac ggt agt ggt agt gga tca atc cag ggt aga tct cct      162
His His His His Gly Ser Gly Ser Gly Ser Ile Gln Gly Arg Ser Pro
             10                  15                  20 ggt acc gag cca cca acc cag aag ccc aag gcg att gta aat gcc aag      210
Gly Thr Glu Pro Pro Thr Gln Lys Pro Lys Ala Ile Val Asn Ala Lys
         25                  30                  35 gca gat gtt gtg aac aca aag atg ttt gag gag ctc aag agc cgt ctg      258
Ala Asp Val Val Asn Thr Lys Met Phe Glu Glu Leu Lys Ser Arg Leu
     40                  45                  50 gac acc ctg gcc cag gag gtg gcc ctg ctg aag gag cag cag gcc ctg      306
Asp Thr Leu Ala Gln Glu Val Ala Leu Leu Lys Glu Gln Gln Ala Leu
 55                  60                  65 cag acg gtc tcc ctg aag gga acc aag gtg cac atg aag gaa ccc ccc      354
Gln Thr Val Ser Leu Lys Gly Thr Lys Val His Met Lys Glu Pro Pro
70                  75                  80                  85 cag agc ccc tgg gat cga gtg aag gac ctg gcc act gtg tac gtg gat      402
Gln Ser Pro Trp Asp Arg Val Lys Asp Leu Ala Thr Val Tyr Val Asp
                 90                  95                 100 gtg ctc aaa gac agc ggc aga gac tat gtg tcc cag ttt gaa ggc tcc      450
Val Leu Lys Asp Ser Gly Arg Asp Tyr Val Ser Gln Phe Glu Gly Ser
            105                 110                 115 gcc ttg gga aaa cag cta aac cta aag ctc ctt gac aac tgg gac agc      498
Ala Leu Gly Lys Gln Leu Asn Leu Lys Leu Leu Asp Asn Trp Asp Ser
        120                 125                 130
```

| | | |
|---|---|---|
| gtg acc tcc acc ttc agc aag ctg cgc gaa cag ctc ggc cct gtg acc<br>Val Thr Ser Thr Phe Ser Lys Leu Arg Glu Gln Leu Gly Pro Val Thr<br>135                    140                    145 | | 546 |
| cag gag ttc tgg gat aac ctg gaa aag gag aca gag ggc ctg agg cag<br>Gln Glu Phe Trp Asp Asn Leu Glu Lys Glu Thr Glu Gly Leu Arg Gln<br>150                    155                    160                    165 | | 594 |
| gag atg agc aag gat ctg gag gag gtg aag gcc aag gtg cag ccc tac<br>Glu Met Ser Lys Asp Leu Glu Glu Val Lys Ala Lys Val Gln Pro Tyr<br>                    170                    175                    180 | | 642 |
| ctg gac gac ttc cag aag aag tgg cag gag gag atg gag ctc tac cgc<br>Leu Asp Asp Phe Gln Lys Lys Trp Gln Glu Glu Met Glu Leu Tyr Arg<br>185                    190                    195 | | 690 |
| cag aag gtg gag ccg ctg cgc gca gag ctc caa gag ggc gcg cgc cag<br>Gln Lys Val Glu Pro Leu Arg Ala Glu Leu Gln Glu Gly Ala Arg Gln<br>                    200                    205                    210 | | 738 |
| aag ctg cac gag ctg caa gag aag ctg agc cca ctg ggc gag gag atg<br>Lys Leu His Glu Leu Gln Glu Lys Leu Ser Pro Leu Gly Glu Glu Met<br>215                    220                    225 | | 786 |
| cgc gac cgc gcg cgc gcc cat gtg gac gcg ctg cgc acg cat ctg gcc<br>Arg Asp Arg Ala Arg Ala His Val Asp Ala Leu Arg Thr His Leu Ala<br>230                    235                    240                    245 | | 834 |
| ccc tac agc gac gag ctg cgc cag cgc ttg gcc gcg cgc ctt gag gct<br>Pro Tyr Ser Asp Glu Leu Arg Gln Arg Leu Ala Ala Arg Leu Glu Ala<br>                    250                    255                    260 | | 882 |
| ctc aag gag aac ggc ggc gcc aga ctg gcc gag tac cac gcc aag gcc<br>Leu Lys Glu Asn Gly Gly Ala Arg Leu Ala Glu Tyr His Ala Lys Ala<br>                    265                    270                    275 | | 930 |
| acc gag cat ctg agc acg ctc agc gag aag gcc aag ccc gcg ctc gag<br>Thr Glu His Leu Ser Thr Leu Ser Glu Lys Ala Lys Pro Ala Leu Glu<br>280                    285                    290 | | 978 |
| gac ctc cgc caa ggc ctg ctg ccc gtg ctg gag agc ttc aag gtc agc<br>Asp Leu Arg Gln Gly Leu Leu Pro Val Leu Glu Ser Phe Lys Val Ser<br>295                    300                    305 | | 1026 |
| ttc ctg agc gct ctc gag gag tac act aag aag ctc aac acc cag<br>Phe Leu Ser Ala Leu Glu Glu Tyr Thr Lys Lys Leu Asn Thr Gln<br>310                    315                    320 | | 1071 |
| taataagctt gaattccgat ccggctgcta acaaagcccg aaaggaagct gagttggctg | | 1131 |
| cctgccaccg ctgagctgag caataactag cataacccct ctgccaccgc tgtgggggcct | | 1191 |
| ctaaacgggt cttgaggggt ttttgctga aggaggaac tatatccgat | | 1241 |

<210> SEQ ID NO 66
<211> LENGTH: 324
<212> TYPE: PRT
<213> ORGANISM: Artificial Sequence
<220> FEATURE:
<223> OTHER INFORMATION: pT7H6 Trip-A-Tn-Apo A1 final K9AK15A - AmpR
    plasmid

<400> SEQUENCE: 66

Met Gly Ser His His His His His His Gly Ser Gly Ser Gly Ser Ile
1                 5                    10                  15

Gln Gly Arg Ser Pro Gly Thr Glu Pro Pro Thr Gln Lys Pro Lys Ala
              20                    25                    30

Ile Val Asn Ala Lys Ala Asp Val Val Asn Thr Lys Met Phe Glu Glu
        35                    40                    45

Leu Lys Ser Arg Leu Asp Thr Leu Ala Gln Glu Val Ala Leu Leu Lys
    50                    55                    60

Glu Gln Gln Ala Leu Gln Thr Val Ser Leu Lys Gly Thr Lys Val His
65                    70                    75                    80

-continued

```
Met Lys Glu Pro Pro Gln Ser Pro Trp Asp Arg Val Lys Asp Leu Ala
                85                  90                  95

Thr Val Tyr Val Asp Val Leu Lys Asp Ser Gly Arg Asp Tyr Val Ser
            100                 105                 110

Gln Phe Glu Gly Ser Ala Leu Gly Lys Gln Leu Asn Leu Lys Leu Leu
        115                 120                 125

Asp Asn Trp Asp Ser Val Thr Ser Thr Phe Ser Lys Leu Arg Glu Gln
130                 135                 140

Leu Gly Pro Val Thr Gln Glu Phe Trp Asp Asn Leu Glu Lys Glu Thr
145                 150                 155                 160

Glu Gly Leu Arg Gln Glu Met Ser Lys Asp Leu Glu Glu Val Lys Ala
                165                 170                 175

Lys Val Gln Pro Tyr Leu Asp Asp Phe Gln Lys Lys Trp Gln Glu Glu
            180                 185                 190

Met Glu Leu Tyr Arg Gln Lys Val Glu Pro Leu Arg Ala Glu Leu Gln
        195                 200                 205

Glu Gly Ala Arg Gln Lys Leu His Glu Leu Gln Glu Lys Leu Ser Pro
    210                 215                 220

Leu Gly Glu Glu Met Arg Asp Arg Ala Arg Ala His Val Asp Ala Leu
225                 230                 235                 240

Arg Thr His Leu Ala Pro Tyr Ser Asp Glu Leu Arg Gln Arg Leu Ala
                245                 250                 255

Ala Arg Leu Glu Ala Leu Lys Glu Asn Gly Gly Ala Arg Leu Ala Glu
            260                 265                 270

Tyr His Ala Lys Ala Thr Glu His Leu Ser Thr Leu Ser Glu Lys Ala
        275                 280                 285

Lys Pro Ala Leu Glu Asp Leu Arg Gln Gly Leu Leu Pro Val Leu Glu
    290                 295                 300

Ser Phe Lys Val Ser Phe Leu Ser Ala Leu Glu Glu Tyr Thr Lys Lys
305                 310                 315                 320

Leu Asn Thr Gln
```

<210> SEQ ID NO 67
<211> LENGTH: 1301
<212> TYPE: DNA
<213> ORGANISM: Artificial Sequence
<220> FEATURE:
<223> OTHER INFORMATION: pT7H6 Hp-alpha-Apo A1 - AmpR plasmid
<221> NAME/KEY: CDS
<222> LOCATION: (100)..(1131)
<223> OTHER INFORMATION:

<400> SEQUENCE: 67

```
gatctcgatc ccgcgaaatt aatacgatac actatagggaa gaccacaacg gtttccctct      60
agaaataatt ttgtttaact ttaagaagga gatatacat atg gga tcg cat cac       114
                                            Met Gly Ser His His
                                              1               5 cat cac cat cac gga tcg atc cag ggt aga ggt gtg gac tca ggc aat     162
His His His His Gly Ser Ile Gln Gly Arg Gly Val Asp Ser Gly Asn
             10                  15                  20 gat gtc acg gat atc gca gat gac ggc tgc ccg aag ccc ccc gag att     210
Asp Val Thr Asp Ile Ala Asp Asp Gly Cys Pro Lys Pro Pro Glu Ile
         25                  30                  35 gca cat ggc tat gtg gag cac tcg gtt cgc tac cag tgt aag aac tac     258
Ala His Gly Tyr Val Glu His Ser Val Arg Tyr Gln Cys Lys Asn Tyr
     40                  45                  50
```

| | | |
|---|---|---|
| tac aaa ctg cgc aca gaa gga gat gga gta tac acc tta aac aat gag<br>Tyr Lys Leu Arg Thr Glu Gly Asp Gly Val Tyr Thr Leu Asn Asn Glu<br>     55                    60                   65 | | 306 |
| aag cag tgg ata aat aag gct gtt gga gat aaa ctt cct gaa tgt gaa<br>Lys Gln Trp Ile Asn Lys Ala Val Gly Asp Lys Leu Pro Glu Cys Glu<br>70                 75                    80                  85 | | 354 |
| gca gta gct ggg aag ccc aag aat ccg gca aac cca gtg cag aga tcc<br>Ala Val Ala Gly Lys Pro Lys Asn Pro Ala Asn Pro Val Gln Arg Ser<br>                  90                    95                  100 | | 402 |
| gat gaa ccc ccc cag agc ccc tgg gat cga gtg aag gac ctg gcc act<br>Asp Glu Pro Pro Gln Ser Pro Trp Asp Arg Val Lys Asp Leu Ala Thr<br>               105                    110                115 | | 450 |
| gtg tac gtg gat gtg ctc aaa gac agc ggc aga gac tat gtg tcc cag<br>Val Tyr Val Asp Val Leu Lys Asp Ser Gly Arg Asp Tyr Val Ser Gln<br>         120                    125                  130 | | 498 |
| ttt gaa ggc tcc gcc ttg gga aaa cag cta aac cta aag ctc ctt gac<br>Phe Glu Gly Ser Ala Leu Gly Lys Gln Leu Asn Leu Lys Leu Leu Asp<br>       135                  140                 145 | | 546 |
| aac tgg gac agc gtg acc tcc acc ttc agc aag ctg cgc gaa cag ctc<br>Asn Trp Asp Ser Val Thr Ser Thr Phe Ser Lys Leu Arg Glu Gln Leu<br>150                155                  160              165 | | 594 |
| ggc cct gtg acc cag gag ttc tgg gat aac ctg gaa aag gag aca gag<br>Gly Pro Val Thr Gln Glu Phe Trp Asp Asn Leu Glu Lys Glu Thr Glu<br>                 170                  175              180 | | 642 |
| ggc ctg agg cag gag atg agc aag gat ctg gag gag gtg aag gcc aag<br>Gly Leu Arg Gln Glu Met Ser Lys Asp Leu Glu Glu Val Lys Ala Lys<br>             185                  190                195 | | 690 |
| gtg cag ccc tac ctg gac gac ttc cag aag aag tgg cag gag gag atg<br>Val Gln Pro Tyr Leu Asp Asp Phe Gln Lys Lys Trp Gln Glu Glu Met<br>         200                    205                210 | | 738 |
| gag ctc tac cgc cag aag gtg gag ccg ctg cgc gca gag ctc caa gag<br>Glu Leu Tyr Arg Gln Lys Val Glu Pro Leu Arg Ala Glu Leu Gln Glu<br>       215                  220               225 | | 786 |
| ggc gcg cgc cag aag ctg cac gag ctg caa gag aag ctg agc cca ctg<br>Gly Ala Arg Gln Lys Leu His Glu Leu Gln Glu Lys Leu Ser Pro Leu<br>230                235                  240              245 | | 834 |
| ggc gag gag atg cgc gac cgc gcg cgc gcc cat gtg gac gcg ctg cgc<br>Gly Glu Glu Met Arg Asp Arg Ala Arg Ala His Val Asp Ala Leu Arg<br>             250                  255                260 | | 882 |
| acg cat ctg gcc ccc tac agc gac gag ctg cgc cag cgc ttg gcc gcg<br>Thr His Leu Ala Pro Tyr Ser Asp Glu Leu Arg Gln Arg Leu Ala Ala<br>             265                  270                275 | | 930 |
| cgc ctt gag gct ctc aag gag aac ggc ggc gcc aga ctg gcc gag tac<br>Arg Leu Glu Ala Leu Lys Glu Asn Gly Gly Ala Arg Leu Ala Glu Tyr<br>         280                    285                290 | | 978 |
| cac gcc aag gcc acc gag cat ctg agc acg ctc agc gag aag gcc aag<br>His Ala Lys Ala Thr Glu His Leu Ser Thr Leu Ser Glu Lys Ala Lys<br>       295                  300                305 | | 1026 |
| ccc gcg ctc gag gac ctc cgc caa ggc ctg ctg ccc gtg ctg gag agc<br>Pro Ala Leu Glu Asp Leu Arg Gln Gly Leu Leu Pro Val Leu Glu Ser<br>310                315                  320              325 | | 1074 |
| ttc aag gtc agc ttc ctg agc gct ctc gag gag tac act aag aag ctc<br>Phe Lys Val Ser Phe Leu Ser Ala Leu Glu Glu Tyr Thr Lys Lys Leu<br>             330                  335                340 | | 1122 |
| aac acc cag taataagctt gaattccgat ccggctgcta acaaagcccg<br>Asn Thr Gln | | 1171 |

-continued

```
aaaggaagct gagttggctg cctgccaccg ctgagctgag caataactag cataacccct    1231
ctgccaccgc tgtggggcct ctaaacgggt cttgaggggt tttttgctga aaggaggaac    1291
tatatccgat                                                           1301
```

<210> SEQ ID NO 68
<211> LENGTH: 344
<212> TYPE: PRT
<213> ORGANISM: Artificial Sequence
<220> FEATURE:
<223> OTHER INFORMATION: pT7H6 Hp-alpha-Apo A1 - AmpR plasmid

<400> SEQUENCE: 68

```
Met Gly Ser His His His His His His Gly Ser Ile Gln Gly Arg Gly
1               5                   10                  15

Val Asp Ser Gly Asn Asp Val Thr Asp Ile Ala Asp Asp Gly Cys Pro
            20                  25                  30

Lys Pro Pro Glu Ile Ala His Gly Tyr Val Glu His Ser Val Arg Tyr
        35                  40                  45

Gln Cys Lys Asn Tyr Tyr Lys Leu Arg Thr Glu Gly Asp Gly Val Tyr
    50                  55                  60

Thr Leu Asn Asn Glu Lys Gln Trp Ile Asn Lys Ala Val Gly Asp Lys
65                  70                  75                  80

Leu Pro Glu Cys Glu Ala Val Ala Gly Lys Pro Lys Asn Pro Ala Asn
                85                  90                  95

Pro Val Gln Arg Ser Asp Glu Pro Pro Gln Ser Pro Trp Asp Arg Val
            100                 105                 110

Lys Asp Leu Ala Thr Val Tyr Val Asp Val Leu Lys Asp Ser Gly Arg
        115                 120                 125

Asp Tyr Val Ser Gln Phe Glu Gly Ser Ala Leu Gly Lys Gln Leu Asn
    130                 135                 140

Leu Lys Leu Leu Asp Asn Trp Asp Ser Val Thr Ser Thr Phe Ser Lys
145                 150                 155                 160

Leu Arg Glu Gln Leu Gly Pro Val Thr Gln Glu Phe Trp Asp Asn Leu
                165                 170                 175

Glu Lys Glu Thr Glu Gly Leu Arg Gln Glu Met Ser Lys Asp Leu Glu
            180                 185                 190

Glu Val Lys Ala Lys Val Gln Pro Tyr Leu Asp Asp Phe Gln Lys Lys
        195                 200                 205

Trp Gln Glu Glu Met Glu Leu Tyr Arg Gln Lys Val Glu Pro Leu Arg
    210                 215                 220

Ala Glu Leu Gln Glu Gly Ala Arg Gln Lys Leu His Glu Leu Gln Glu
225                 230                 235                 240

Lys Leu Ser Pro Leu Gly Glu Glu Met Arg Asp Arg Ala Arg Ala His
                245                 250                 255

Val Asp Ala Leu Arg Thr His Leu Ala Pro Tyr Ser Asp Glu Leu Arg
            260                 265                 270

Gln Arg Leu Ala Ala Arg Leu Glu Ala Leu Lys Glu Asn Gly Gly Ala
        275                 280                 285

Arg Leu Ala Glu Tyr His Ala Lys Ala Thr Glu His Leu Ser Thr Leu
    290                 295                 300

Ser Glu Lys Ala Lys Pro Ala Leu Glu Asp Leu Arg Gln Gly Leu Leu
305                 310                 315                 320
```

```
Pro Val Leu Glu Ser Phe Lys Val Ser Phe Leu Ser Ala Leu Glu Glu
            325                 330                 335

Tyr Thr Lys Lys Leu Asn Thr Gln
            340

<210> SEQ ID NO 69
<211> LENGTH: 7
<212> TYPE: PRT
<213> ORGANISM: Artificial Sequence
<220> FEATURE:
<223> OTHER INFORMATION: tetranectin (53-59)  based linker

<400> SEQUENCE: 69

Gly Thr Lys Val His Met Lys
1               5

<210> SEQ ID NO 70
<211> LENGTH: 13
<212> TYPE: PRT
<213> ORGANISM: Artificial Sequence
<220> FEATURE:
<223> OTHER INFORMATION: fibronectin (2037-2049) based linker

<400> SEQUENCE: 70

Pro Gly Thr Ser Gly Gln Gln Pro Ser Val Gly Gln Gln
1               5                   10

<210> SEQ ID NO 71
<211> LENGTH: 10
<212> TYPE: PRT
<213> ORGANISM: Artificial Sequence
<220> FEATURE:
<223> OTHER INFORMATION: murine IgG3 upper hinge region-based linker

<400> SEQUENCE: 71

Pro Lys Pro Ser Thr Pro Pro Gly Ser Ser
1               5                   10

<210> SEQ ID NO 72
<211> LENGTH: 14
<212> TYPE: PRT
<213> ORGANISM: Artificial Sequence
<220> FEATURE:
<223> OTHER INFORMATION: flexible linker (Muller, 2000)

<400> SEQUENCE: 72

Ser Gly Gly Thr Ser Gly Ser Thr Ser Gly Thr Gly Ser Thr
1               5                   10

<210> SEQ ID NO 73
<211> LENGTH: 15
<212> TYPE: PRT
<213> ORGANISM: Artificial Sequence
<220> FEATURE:
<223> OTHER INFORMATION: flexible linker (Muller, 2000)

<400> SEQUENCE: 73

Ala Gly Ser Ser Thr Gly Ser Ser Thr Gly Pro Gly Ser Thr Thr
1               5                   10                  15

<210> SEQ ID NO 74
<211> LENGTH: 7
<212> TYPE: PRT
<213> ORGANISM: Artificial Sequence
<220> FEATURE:
<223> OTHER INFORMATION: flexible linker (Muller, 2000)
```

```
<400> SEQUENCE: 74

Gly Gly Ser Gly Gly Ala Pro
1               5

<210> SEQ ID NO 75
<211> LENGTH: 45
<212> TYPE: DNA
<213> ORGANISM: Artificial Sequence
<220> FEATURE:
<223> OTHER INFORMATION: Ubi-A-I primer #1

<400> SEQUENCE: 75
cacggatcca tcgagggtag gggtggagat gaaccccccc agagc            45

<210> SEQ ID NO 76
<211> LENGTH: 35
<212> TYPE: DNA
<213> ORGANISM: Artificial Sequence
<220> FEATURE:
<223> OTHER INFORMATION: Ubi-A-I primer #2

<400> SEQUENCE: 76
tccaagctta ttactgggtg ttgagcttct tagtg                       35

<210> SEQ ID NO 77
<211> LENGTH: 30
<212> TYPE: DNA
<213> ORGANISM: Artificial Sequence
<220> FEATURE:
<223> OTHER INFORMATION: Trip-A-A-I primer #1

<400> SEQUENCE: 77
aagggatccg atgaaccccc ccagagcccc                             30

<210> SEQ ID NO 78
<211> LENGTH: 35
<212> TYPE: DNA
<213> ORGANISM: Artificial Sequence
<220> FEATURE:
<223> OTHER INFORMATION: Trip-A-A-I primer #2

<400> SEQUENCE: 78
tccaagctta ttactgggtg ttgagcttct tagtg                       35

<210> SEQ ID NO 79
<211> LENGTH: 31
<212> TYPE: DNA
<213> ORGANISM: Artificial Sequence
<220> FEATURE:
<223> OTHER INFORMATION: Trip-A-I-del43 primer #1

<400> SEQUENCE: 79
aggggatccc taaagctcct tgacaactgg g                           31

<210> SEQ ID NO 80
<211> LENGTH: 35
<212> TYPE: DNA
<213> ORGANISM: Artificial Sequence
<220> FEATURE:
<223> OTHER INFORMATION: Trip-A-I-del43 primer #2

<400> SEQUENCE: 80
tccaagctta ttactgggtg ttgagcttct tagtg                       35
```

```
<210> SEQ ID NO 81
<211> LENGTH: 43
<212> TYPE: DNA
<213> ORGANISM: Artificial Sequence
<220> FEATURE:
<223> OTHER INFORMATION: Ubi-Cys-A-I primer #1

<400> SEQUENCE: 81
ggtggatcca tcgagggtag gggtggatgt gatgaacccc ccc            43

<210> SEQ ID NO 82
<211> LENGTH: 35
<212> TYPE: DNA
<213> ORGANISM: Artificial Sequence
<220> FEATURE:
<223> OTHER INFORMATION: Ubi-Cys-A-I primer #2

<400> SEQUENCE: 82
tccaagctta ttactgggtg ttgagcttct tagtg                     35

<210> SEQ ID NO 83
<211> LENGTH: 39
<212> TYPE: DNA
<213> ORGANISM: Artificial Sequence
<220> FEATURE:
<223> OTHER INFORMATION: pT7H6Fx-Trip-A-FN(-2)-AI primer

<400> SEQUENCE: 83
cgcggatcct cgggtcagga tgaaccccccc cagagcccc                39

<210> SEQ ID NO 84
<211> LENGTH: 45
<212> TYPE: DNA
<213> ORGANISM: Artificial Sequence
<220> FEATURE:
<223> OTHER INFORMATION: pT7H6Fx-Trip-A-TN-AI-Bam-S primer

<400> SEQUENCE: 84
cgcggatcca aggtgcacat gaaggatgaa ccccccaga gcccc           45

<210> SEQ ID NO 85
<211> LENGTH: 34
<212> TYPE: DNA
<213> ORGANISM: Artificial Sequence
<220> FEATURE:
<223> OTHER INFORMATION: pT7H6Fx-Trip-FN-AI primer #1

<400> SEQUENCE: 85
acggtctccc tgaagggaac ctcgggtcag gatg                      34

<210> SEQ ID NO 86
<211> LENGTH: 37
<212> TYPE: DNA
<213> ORGANISM: Artificial Sequence
<220> FEATURE:
<223> OTHER INFORMATION: pT-H6Fx-Trip-TN-AI primer

<400> SEQUENCE: 86
acggtctccc tgaagggaac caaggtgcac atgaagg                   37

<210> SEQ ID NO 87
<211> LENGTH: 33
<212> TYPE: DNA
<213> ORGANISM: Artificial Sequence
<220> FEATURE:
<223> OTHER INFORMATION: primer #1 to mutate lysine 9 from Trip-A
```

```
-continued

<400> SEQUENCE: 87
ccaacccaga agcccaaggc gaatgtaaat gcc                              33

<210> SEQ ID NO 88
<211> LENGTH: 33
<212> TYPE: DNA
<213> ORGANISM: Artificial Sequence
<220> FEATURE:
<223> OTHER INFORMATION: primer #2 to mutate lysine 9 from Trip-A

<400> SEQUENCE: 88
gtgttcacaa catctgcctt ggcatttaca atc                              33

<210> SEQ ID NO 89
<211> LENGTH: 33
<212> TYPE: DNA
<213> ORGANISM: Artificial Sequence
<220> FEATURE:
<223> OTHER INFORMATION: primer #1 to mutate lysine 15 from Trip-A

<400> SEQUENCE: 89
ggcatttaca atcgccttgg gcttctgggt tgg                              33

<210> SEQ ID NO 90
<211> LENGTH: 48
<212> TYPE: DNA
<213> ORGANISM: Artificial Sequence
<220> FEATURE:
<223> OTHER INFORMATION: HP-alpha-A-I cDNA fetal liver library
      "nonsense" primer

<400> SEQUENCE: 90
cacaagcttt ccgctagatc tctgcactgg gttagccgga ttcttggg              48

<210> SEQ ID NO 91
<211> LENGTH: 49
<212> TYPE: DNA
<213> ORGANISM: Artificial Sequence
<220> FEATURE:
<223> OTHER INFORMATION: HP-alpha-A-I fetal liver cDNA library "sense"
      primer

<400> SEQUENCE: 91
ggtggatcca tcgagggtag gggtgtggac tcaggcaatg atgtcacgg             49
```